(12) United States Patent
Shimojo et al.

(10) Patent No.: US 11,866,705 B2
(45) Date of Patent: Jan. 9, 2024

(54) SMALL CELL LUNG CANCER THERAPEUTIC AGENT CONTAINING OLIGONUCLEOTIDE

(71) Applicants: Osaka University, Osaka (JP); National Institutes of Biomedical Innovation, Health and Nutrition, Osaka (JP); Luxna Biotech Co., Ltd., Osaka (JP)

(72) Inventors: Masahito Shimojo, Osaka (JP); Satoshi Obika, Osaka (JP); Yuya Kasahara, Osaka (JP); Takao Suzuki, Osaka (JP); Masaki Yamagami, Osaka (JP); Tadashi Umemoto, Osaka (JP)

(73) Assignees: Osaka Univerity, Osaka (JP); National Institutes of Biomedical Innovation, Health and Nutrition, Osaka (JP); Luxna Biotech Co., Ltd., Osaka (JP)

(*) Notice: Subject to any disclaimer, the term of this patent is extended or adjusted under 35 U.S.C. 154(b) by 177 days.

(21) Appl. No.: 17/261,653

(22) PCT Filed: Jul. 31, 2019

(86) PCT No.: PCT/JP2019/030090
§ 371 (c)(1),
(2) Date: Jan. 20, 2021

(87) PCT Pub. No.: WO2020/027227
PCT Pub. Date: Feb. 6, 2020

(65) Prior Publication Data
US 2021/0277398 A1   Sep. 9, 2021

(30) Foreign Application Priority Data
Jul. 31, 2018  (JP) .................. 2018-144016

(51) Int. Cl.
*C12N 15/113*   (2010.01)

(52) U.S. Cl.
CPC ........ *C12N 15/113* (2013.01); *C12N 2310/11* (2013.01); *C12N 2310/3231* (2013.01)

(58) Field of Classification Search
CPC ............. C12N 15/113; C12N 2310/11; C12N 2310/3231; C12N 2310/341;
(Continued)

(56) References Cited

U.S. PATENT DOCUMENTS

| | | | |
|---|---|---|---|
| 7,250,496 B2 * | 7/2007 | Bentwich | ............... G16B 15/10 435/320.1 |
| 7,374,927 B2 * | 5/2008 | Palma | .................. C12Q 1/6883 536/23.1 |

(Continued)

FOREIGN PATENT DOCUMENTS

| | | |
|---|---|---|
| JP | 2008500039 A | 1/2008 |
| WO | 2015012175 A1 | 1/2015 |
| WO | WO-2015012175 A1 * | 1/2015 ......... A61K 31/7088 |

OTHER PUBLICATIONS

Henry et al. 2000 (Chemically Modified Oligonucleotides Exhibit Decreased Immune Stimulation in Mice. The Journal of Pharmacology and Experimental Therapeutics 292:468-479) (Year: 2000).*

(Continued)

*Primary Examiner* — Ram R Shukla
*Assistant Examiner* — Ruth Sophia Arieti
(74) *Attorney, Agent, or Firm* — Renner, Otto, Boisselle & Sklar, LLP

(57) ABSTRACT

Disclosed is an oligonucleotide or a pharmacologically acceptable salt thereof, wherein the oligonucleotide comprises at least one defined nucleoside structure, can bind to a human nSR100 gene and has human nSR100 expression inhibiting activity. The oligonucleotide has a length of 12 to 20 mer, and is complementary to a defined target region. Further, disclosed is an nSR100 gene expression inhibitor and a cancer therapeutic agent containing the oligonucle- (Continued)

otide or the pharmacologically acceptable salt thereof. The cancer therapeutic agent is used for treatment of small cell lung cancer, prostate cancer, or breast cancer.

4 Claims, 19 Drawing Sheets

Specification includes a Sequence Listing.

(58) Field of Classification Search
CPC .... C12N 2310/346; A61P 13/08; A61P 15/00; A61P 35/00; A61P 43/00; A61P 11/00
See application file for complete search history.

(56) References Cited

U.S. PATENT DOCUMENTS

| | | | |
|---|---|---|---|
| 8,541,562 B2* | 9/2013 | Obika | C07H 19/173 536/28.1 |
| 9,611,479 B2* | 4/2017 | Obika | C12N 15/113 |
| 2005/0244851 A1 | 11/2005 | Blume et al. | |
| 2005/0272080 A1 | 12/2005 | Palma et al. | |
| 2007/0050146 A1 | 3/2007 | Bentwich et al. | |
| 2012/0208991 A1 | 8/2012 | Obika et al. | |
| 2015/0266917 A1 | 9/2015 | Obika et al. | |
| 2017/0044528 A1 | 2/2017 | Obika et al. | |
| 2018/0273577 A1 | 9/2018 | Revenko et al. | |

OTHER PUBLICATIONS

Cheng et al. 2017 (Lipid Nanoparticles Loaded with an Antisense Oligonucleotide Gapmer Against Bcl-2 for Treatment of Lung Cancer. Pharm. Res. 34:310-320) (Year: 2017).*

PCT/JP2019/030090; PCT International Search Report of the International Searching Authority dated Oct. 25, 2019 and its English translation.

M. Kuwahara et al., Nucleic Acids Res., 2008, vol. 36, No. 13, pp. 4257-4265.

Tetrahedron Letters, 1981, vol. 22. pp. 1859-1862.

* cited by examiner (A)

(B)

A.

(a)

(b)

B.

(a)

(b)

SEQUENCE LISTING

```
<160> NUMBER OF SEQ ID NOS: 219

<210> SEQ ID NO 1
<211> LENGTH: 8494
<212> TYPE: DNA
<213> ORGANISM: Homo sapiens
<220> FEATURE:
<221> NAME/KEY: misc_feature
<223> OTHER INFORMATION: nSR100

<400> SEQUENCE: 1
gtcacattgt gcgagagaca aaacccgggc gcgccggagc tcacacgcgc acgcacacac      60
atccgacccc gtcgcctctt ctctcctggt gctgcccaga aagccagccc tcccttccct     120
tcttggggcg cagaggctca gccagctcag agcgcagcct ggagccgacc cagaagggcg     180
```

```
aagaaagccc agcggacgag cctcctttct ctgctgcctg cccgggctgg ggcgtcccat    240 ccccgccct  gaactccgat ctctcccacc ccacccctct ctgggtttca cccggacaga    300
gccgggagct gggtgtcgcc cccgtttgga atccacgttt cagcactttg gacagcgccc    360
cggacgcccc ggcccctttg ggttggcgat ggcgagcgtt cagcaaggcg agaagcagct    420
ttttgagaag ttctggcgag gaaccttcaa agcggtggcc accccccgtc ccgagagcat    480
cattgtcgcc agtatcacgg cccgcaagcc gctgccaagg acagagcccc agaataaccc    540
cgttgtccca gctcaggatg gaccctcaga aaagctgggt cagcatctgg ccaccgagcc    600
cttgggcacc aacagttggg agagagacaa gacctgtcgg gaactgggtg ccaccagagg    660
acacagtgcc tctcatgaca aagacttgac accaccacct tcctccaggg gaaagaagaa    720
aaagaagaaa tccactcgga gaagagaag  gaggtcctca tcctatagcc catcgcctgt    780
caagaaaaag aagaagaaaa gttccaagaa acacaagcga cgcaggtcat tctccaagaa    840
gagaaggcac agctcctcta gcccaaaaag caaaagaaga gatgagaaga ggcacaagaa    900
acaatctcga agccggcccc gaaagtctca ccgccaccgc catcaccgct gcccctcgcg    960
gtcccagagc tcggagtccc gcccctcaag ctgtgagagc aggcaccgcg gccggtcccc   1020
tgaggaaggg cagaagtccc gccgaaggca ctcccgccgc tgctccaaga ccctctgcaa   1080
ggacagccct gaggcccagt ccagtcgccc gccagtcaa  cccctccaga tgcttggcta   1140
cctgtcagcc aggggtgtaa tcactgggtc ggggtctgct gctgacctct ttaccaaaac   1200
agccagcccg ctcaccacct cgcgaggacg ttcccaggag tacgactcag gaaatgacac   1260
gtcctcgcca ccctccacgc aaaccagctc agccaggtct cggggccagg agaaggggag   1320
ccccagtggg ggcttgagca agagccggga gctcaacagt ggcaacacct ctgattcagg   1380
gaactccttc accactcct  cacccagaa  caagggggcc atgttggaga atctctcccc   1440
caccagcagg ggcagagagt caaggggatt tcagtcaccg tgtctggaat gtgccgaagt   1500
gaagaagtcc agtttggtcc catccacagc ccggagctca cccatgaaag ggtgttcccg   1560
cagctcctcc tatgccagca cccgatcctc cagtcactcg tcccgatccc caaatcccag   1620
ggcttccccc aggtacaccc aaagccgatc cacctcttct gaaaaaaggt cctactcccg   1680
ctctcccagc tattcctcca agtctggcaa gaggagcccg cccagcagaa gctctaggtc   1740
ccgccgcagc cctagctact cccgctacag ccccagcagg gagcgggatc ccaaatacag   1800
tgagaaggac tcgcagcagc gggagcgcga gcgagcgcgt cggagacgtc ggtcctactc   1860
gcctatgaga aagcgccgga gagactcccc gagccacctg gaggcccgga ggataaccag   1920
tgcccggaaa cgccccatcc cctactatcg gcccagcccc tcctcatccg gcagcctcag   1980
cagcacctcc tcctggtaca gcagcagcag tagccgctcg gccagccgca gctactcccg   2040
gagccggagt cggagccgga gccggagacg gagccggacc cgcacgagca gcagctctag   2100
ctcccgcagc cctagtccgg gctcccgcag ccggagccgg agcaggagcc ggagccggag   2160
ccggagcagg agccagagcc ggagctacag ctcagcagac agctactcca gcacgaggcg   2220
ctaagtgccc ctgagccagc tgccgtgggg ggcccttcg  cgctgccagc ctcccccaac   2280 cacctgcct  cccgccttc  ttggtgacaa atagtgaggg ctcctatacc ttgtccttcc   2340
tgcttgccta ggggaagagg agaagagggt aaggggctt  cactctctag atcagcctgc   2400
taggagcctc taccagcatc atcctggggc ccagctcagg cctgggcata tggaaagaac   2460
catcatcttg tggcacaaaa aaagaagaaa gaaaagaaaa cttcaaggtt ttgtgagaag   2520
caatgggtct gtgactcaaa aattgagccc tggccaggaa aatgtggaga cagttcttct   2580
```

```
cctccactgc tcacaggagg cccgtggtaa ttctccccac ctcccggat gccccactag    2640 tccaacttca tggctgcacg tggatggacc cccatgtctg agaggggtga aagaggagac    2700
caatggcagt tcaggttcaa gataacgggg tcaggccttt aacttcctca aacaggccca    2760
agcaaaggct ggaagacatt tgggtcctag aagaagggga atccttgaat accagatggg    2820
gacgtttgac ttggtgggag gtgtcaggag ataggagttg gttaagatga tagatagaaa    2880
aacgaagggg ttcagctgct gctcccaata cctcagcatg gtaaggggac agagcccagc    2940
agatcccagc tgtgaagagg ccactgcatg gctgacacaa aacacctctt ggccattcac    3000
aggggccctg caacctcacg agaaaggaga tagtggaaga gtcaggacag gttggtctcc    3060
agccccactt cccaaatatg cctcagcccc actagctggc accaacttaa ttccacggga    3120
ccatctgctg aacattcccc agtgccatgg ccagttgcca ggcccagcg ccagccagtc    3180 tggccttacc ctccggttgg cgcctgccag cccctcccc tctgcccagg ctgccacgcc    3240
ctggatgcca cccagtgcag cctggcacct acccacccac ccttcagctt aagccactcc    3300
ccttgcctct caggaatttt gccaggatgg ggcacagcag ctcaggtttg ggggaaaaga    3360
cccgaatcca gagtgcaggg gagaggggct tggatatgcc atgtcttggg ctcctgctgg    3420
cttctgaggt ttcttgtcag cttgggaaag acccacctttt attttttgccc tcaccccaag    3480 tccccctgg ctggggctgg gcagagaggg taagctgatc tccgatccac aaataccacc    3540
agctgcttca tccacagaag gcgctaagaa cggggaggtg aggaataaga tccttaaaat    3600
aaactcttgg gcatcccct caccagctga ctggctttcc ggaggcttgt gggtgagttt    3660
caagtttgtg gtggcaacag cagcaggaca gggcacggag ggagcgaggg agagaggacc    3720
ggtcccagct tttggatatt ttgggttatg gggaagcaag ggccaaacat tctttatccc    3780
tcccacccca gggaaaacat ttggaaaata gtccttttttc ttggaagcag tgacgtctcc    3840
ctacccaatc tttcccatcc tatcaaccca tggggctaga gactgccatg caaccaccac    3900
cacgacagcc cttcctccat cagaagacag gagtgagggc cccgggcagc agtggacgac    3960
ccagcctccc cataccgggc ctctggccca gacctaagcc ctgcccacaa agactaatgg    4020
atgccagtgc tgtcactgca gaaggccaga tggcaggtgc ctgggacagg ggcaggtgcc    4080
ccggggaggg caagtacagc cactgtaaat aaccctcgtc cctgcccagg aacccagact    4140
ggacttcagt ctccctccat ggagacaaag gcttcccaga gccaccaaaa accttcttag    4200
caggacagct gtgagaggca tcagaacctc acgttcggac tgccttcatc aagacaactc    4260
tagggaccca ttttgcctgg ggctcctagc aaaccttttt atttatttta tttatttatc    4320
tatttattta tttgatgact gtctctcttt ctcgccatta gcagtattga attatttatt    4380
tatacagagg ttttgtgtgt gtgtgtgtgt gtgtgtgtgt gtgtgtgtgt gtgtgtgtgt    4440
gtgttggggg gatctcctaa attatttctg tgcatctcct ttttttttct gctgtttttt    4500
atggatggga tttgagaggc caaaggtgag tgggctattg gccttctccc tgaaggctct    4560
aagcctggaa caccctgggg ttggcccaga aggaggcaca tcagtcccaa aattcatcac    4620
ttaacccagc gtccaggagg gtcaggcctg taccccagcc tcctgtcccc caggaacctc    4680 acagggtat caaaaagatg taaacagccc agaggcttat gagctacagt gatgaattga    4740
cacagtggag ttgcaactta ggtgggggtt ggagtcgaaa gttggcaaat ggggccaagg    4800
ctgcacaaag tcgaaatccc ttgtgaatgt cccttaggga ggcaccagat tggagacaga    4860
tgtgctatct cctaacagag tgatgaggct tcagttgagt acttgctgaa gtagttgcct    4920
```

-continued

```
tgtattttga gggccatggt ggatgaaaat gatgtctggt ttagtactgg aattgcactt      4980
ggggttgaca aggtgctcac accatgagaa tggaggcagg aattgagctg actgagggaa      5040
gatgcacctt gatctcaccc tcactccaag gcacatagca ggatcactcc ctagcttctc      5100
tgagcacacc tagttggttt catgtatgtt acacatgctt ccactccaca gtacctaatt      5160
tctctctgtc ccctgagatc tgaaggctac cttgggaaga ggcatcagcc atcttgcttg      5220
agaaccacca agccaaaagc aaaagctttt atctatgatc tcttgctgtt tcatcagggg      5280
aaagcacaaa gctatttctg aaattaggaa aaaaaaaaa aaggtggaag gagcagccag      5340
atgttccaca ggaccccacc aagaaggtca tttccaaacc catcctggaa gggcccagga      5400
tccaaaggtc atcagtcctg cttatctgac caactggcag tgtcttctgg ctgctggccg      5460
gagacagctc ttgcccttte caaagtcact gtccactgcc ttgcaattgc cagcttgtct      5520
ggtccagctt tgggtttggt gagactttg caacatccct ggttgtttcc ctggcaatgt      5580
gactatccag ccctaaccca aagcaaggga gtgccccttt cctgggtgaa gtttacaaga      5640
aggctgctta aatgcctgct tcggggaaat ctctgcctct ctctctctct gtctctctct      5700
ctgtctctct ctctgtctct ctctctctct ctctctctct ctctctctca gtgtatttct      5760
ctactttctt ttacatttcc tttttttcta tccaaaaaca atgtgcttgt tgaggcactg      5820
gtaaccctga ttaaccagaa cctcccattc ccagtatcgc tgttcctacg cccatttcac      5880
cctcattacc ttctgcttcc aaggaatatg acagatcacc aggatgctgc tcgtcgtgag      5940
gatttatctc aaaaccaac atccaaaatg ggagggagat gtggcttgag gtcaagcgcc      6000
atgcatccca agcctttgac cttcccgcta tggaagtgca ctggatgaca gaaactgaat      6060
acattgctcc ctttccctag ggcaaagttc gacctctgtt aagtggaggg atttgtgaga      6120
taaaaattca aaatgttggc ctgaggcctg agagtgtcac caaagacaga gggagcttca      6180
ctgagactca gagggaaaag gaaaagagcc tcaaacattt ttaggaggtt gtccatcatg      6240
aaagtaaaaa cgaaaagcaa gatttgatct cccttcagtt aattaggcaa ggctaagtaa      6300
ctcaaagccc cctattagta acattctggt tcactgaggt ttgatcatat tcctatctgc      6360
attccttccc ttctttgaag gacagctgat ctttcagaag cagaataaaa ttaagatgtt      6420
agaacaaagg tctcagtctc agagaaccgc atcacttcat ttgctcagac ccatcctctt      6480
ttgcaaaagg gtctgcttgg agaggccaaa attcagggtg ctctcaaagg caaagaaagc      6540
acattgtttt ccttctccag tccaactttc atctttttctt ctgctgtttt cttttcccct      6600 cttcttttte acaaatgttc aaaatggtct catgcgcatg tgtcttgccc cactttcccc      6660
tttagctgaa cagaaaattt tgtctcagta aaacgaagtc aaaaaacagg attcctccaa      6720
acatgcctcc tcccgcactg gccagccgag tccagctgag aaacttatgc tagattcaat      6780
gtcattgagc aatgctttat tgaagtctcg ttcttctcac ttctgcacca gtgagccaat      6840
gatactgaca gaaatgtcat ctctcttcta tctgtggttg ctgttttgg agtaaaagtt      6900 tctgtgtgtg tttttttagt tcttttgatg gctgttgttt tgcattgtaa ataccatgat      6960 gggggaccc catcagaaca tggcttattt aataatttat ttcgtattta ttgagtaata      7020
ttgggaaaag agaaggacca cctctttccc tgaattgcta ttgagaattg gtccatctcc      7080
cagctccagg tgctgctgtc tgcagcaagg gcattactgc ccaggtaagg agtgctagaa      7140
tcaccaagca aattgaaatt ggcagaaatg gaggcttcag tcacacaaat tagactcaaa      7200
tggaactaaa acactggtta tctccaggaa aacctcattt agatgaaat taatggaaga      7260 ataaaatgcc tacacatgaa ccaacttcta ttaaaaagtc acaactcctt gaaaaaaaaa      7320
```

```
ataaagaaaa attgtaaact cttttttttt tctggccaag gaaagctatg cctcatcttc    7380
taacgagcca agccaaaaag actgcaatgg tattcctatg tgtttctttg gcctgtgtat    7440
cagtctgaat gaaatggaat gggtctctag cctcagtctt gtcatctgta aaatggggct    7500
tgtcctatat attatctgca agacgtggga aatgggggct caagccctga tgctatggac    7560
tccatactgt tggatatatt gtctcttgtg tcttctgctg actgcagatt aaagggtgtc    7620
aaccaaggaa ggaaacaaaa aagtagggcc tggacttcat ttgcagaatg aggtcatagt    7680
cgttgagtcc cacagtcata tatgggagac ctcaagttgc tgtcaccttg ataactcttg    7740
tatcctgggt taaagccctc tgtatttagt ttgaacttct ctctaagccc cgtggtccaa    7800
agtcatcacg ggagagacca agatgggctt accttgccct gctctggatt taaccattgt    7860
tcattgtcag gctatatttt tgtacaatca ttcaaataac ccagtgacat aggtcatatt    7920 gccactttc agaggagaaa actgaggctc aggagggga gttgacatgc ccaagctccc    7980
ttgagctcag atcagcttga ctcaatgtcc aacattccct tggtagcttt ttctccgggg    8040
tcctgtgcta taagaacttc tctctgcact gtatttttt ttctcccaat tcttagctat    8100
ttcctcaagc aatgattggc caaggaccta gcataatcca ccacattggc caaggggacg    8160
tggtgcaccc caaggccatt tctctgcatt ggaggctgcg aatctcctct ggaaaattcc    8220
caacccgagg acccaccatg agcccagctc agcctgacca gacagcctct gcctggagca    8280
ttcacatcag atggaaagaa gctgctgtgt cctccagcat cctgggaccc tgtcctctgc    8340
ccagtgacac agcagccatg gctagcttga tttctggtct ccaaagctaa gcataacctt    8400
cccggggttt ctggtttttc agcctgtacg aaacatgtct ctgttctaat taaagttccc    8460
atggtatggt gttctcaaaa aaaaaaaaaa aaaa                                8494

<210> SEQ ID NO 2
<211> LENGTH: 15
<212> TYPE: DNA
<213> ORGANISM: Artificial Sequence
<220> FEATURE:
<223> OTHER INFORMATION: #1 base sequence

<400> SEQUENCE: 2 ttcttttct tcttt                                                     15

<210> SEQ ID NO 3
<211> LENGTH: 15
<212> TYPE: DNA
<213> ORGANISM: Artificial Sequence
<220> FEATURE:
<223> OTHER INFORMATION: #2 base sequence

<400> SEQUENCE: 3
atttcttctt tttct                                                    15

<210> SEQ ID NO 4
<211> LENGTH: 15
<212> TYPE: DNA
<213> ORGANISM: Artificial Sequence
<220> FEATURE:
<223> OTHER INFORMATION: #3 base sequence

<400> SEQUENCE: 4
gtggatttct tcttt                                                    15

<210> SEQ ID NO 5
```

```
<211> LENGTH: 15
<212> TYPE: DNA
<213> ORGANISM: Artificial Sequence
<220> FEATURE:
<223> OTHER INFORMATION: #4 base sequence

<400> SEQUENCE: 5
tcttcttttt cttga                                                    15

<210> SEQ ID NO 6
<211> LENGTH: 15
<212> TYPE: DNA
<213> ORGANISM: Artificial Sequence
<220> FEATURE:
<223> OTHER INFORMATION: #5 base sequence

<400> SEQUENCE: 6
tcttcttctt tttct                                                    15

<210> SEQ ID NO 7
<211> LENGTH: 15
<212> TYPE: DNA
<213> ORGANISM: Artificial Sequence
<220> FEATURE:
<223> OTHER INFORMATION: #6 base sequence

<400> SEQUENCE: 7
ttttcttctt ctttt                                                    15

<210> SEQ ID NO 8
<211> LENGTH: 15
<212> TYPE: DNA
<213> ORGANISM: Artificial Sequence
<220> FEATURE:
<223> OTHER INFORMATION: #21 (7174-(15)) base sequence

<400> SEQUENCE: 8
ttgtgtgact gaagc                                                    15

<210> SEQ ID NO 9
<211> LENGTH: 15
<212> TYPE: DNA
<213> ORGANISM: Artificial Sequence
<220> FEATURE:
<223> OTHER INFORMATION: #22 base sequence

<400> SEQUENCE: 9
aatttgtgtg actga                                                    15

<210> SEQ ID NO 10
<211> LENGTH: 17
<212> TYPE: DNA
<213> ORGANISM: Artificial Sequence
<220> FEATURE:
<223> OTHER INFORMATION: 7172-(17) base sequence

<400> SEQUENCE: 10
ttgtgtgact gaagcct                                                  17

<210> SEQ ID NO 11
<211> LENGTH: 19
<212> TYPE: DNA
<213> ORGANISM: Artificial Sequence
<220> FEATURE:
<223> OTHER INFORMATION: 7170-(19) base sequence

<400> SEQUENCE: 11
```

```
ttgtgtgact gaagcctcc                                                  19
```

<210> SEQ ID NO 12
<211> LENGTH: 15
<212> TYPE: DNA
<213> ORGANISM: Artificial Sequence
<220> FEATURE:
<223> OTHER INFORMATION: 7172-(15) base sequence

<400> SEQUENCE: 12

```
gtgtgactga agcct                                                      15
```

<210> SEQ ID NO 13
<211> LENGTH: 17
<212> TYPE: DNA
<213> ORGANISM: Artificial Sequence
<220> FEATURE:
<223> OTHER INFORMATION: 7170-(17) base sequence

<400> SEQUENCE: 13

```
gtgtgactga agcctcc                                                    17
```

<210> SEQ ID NO 14
<211> LENGTH: 19
<212> TYPE: DNA
<213> ORGANISM: Artificial Sequence
<220> FEATURE:
<223> OTHER INFORMATION: 7168-(19) base sequence

<400> SEQUENCE: 14

```
gtgtgactga agcctccat                                                  19
```

<210> SEQ ID NO 15
<211> LENGTH: 15
<212> TYPE: DNA
<213> ORGANISM: Artificial Sequence
<220> FEATURE:
<223> OTHER INFORMATION: 7170-(15) base sequence

<400> SEQUENCE: 15

```
gtgactgaag cctcc                                                      15
```

<210> SEQ ID NO 16
<211> LENGTH: 17
<212> TYPE: DNA
<213> ORGANISM: Artificial Sequence
<220> FEATURE:
<223> OTHER INFORMATION: 7168-(17) base sequence

<400> SEQUENCE: 16

```
gtgactgaag cctccat                                                    17
```

<210> SEQ ID NO 17
<211> LENGTH: 19
<212> TYPE: DNA
<213> ORGANISM: Artificial Sequence
<220> FEATURE:
<223> OTHER INFORMATION: 7166-(19) base sequence

<400> SEQUENCE: 17

```
gtgactgaag cctccattt                                                  19
```

<210> SEQ ID NO 18
<211> LENGTH: 15
<212> TYPE: DNA

```
<213> ORGANISM: Artificial Sequence
<220> FEATURE:
<223> OTHER INFORMATION: 7176-(15) base sequence

<400> SEQUENCE: 18
atttgtgtga ctgaa                                                    15

<210> SEQ ID NO 19
<211> LENGTH: 17
<212> TYPE: DNA
<213> ORGANISM: Artificial Sequence
<220> FEATURE:
<223> OTHER INFORMATION: 7174-(17) base sequence

<400> SEQUENCE: 19
atttgtgtga ctgaagc                                                  17

<210> SEQ ID NO 20
<211> LENGTH: 19
<212> TYPE: DNA
<213> ORGANISM: Artificial Sequence
<220> FEATURE:
<223> OTHER INFORMATION: 7172-(19) base sequence

<400> SEQUENCE: 20
atttgtgtga ctgaagcct                                                19

<210> SEQ ID NO 21
<211> LENGTH: 15
<212> TYPE: DNA
<213> ORGANISM: Artificial Sequence
<220> FEATURE:
<223> OTHER INFORMATION: 7178-(15) base sequence

<400> SEQUENCE: 21
taatttgtgt gactg                                                    15

<210> SEQ ID NO 22
<211> LENGTH: 15
<212> TYPE: DNA
<213> ORGANISM: Artificial Sequence
<220> FEATURE:
<223> OTHER INFORMATION: 604-(15) base sequence

<400> SEQUENCE: 22
caactgttgg tgccc                                                    15

<210> SEQ ID NO 23
<211> LENGTH: 15
<212> TYPE: DNA
<213> ORGANISM: Artificial Sequence
<220> FEATURE:
<223> OTHER INFORMATION: 680-(15) base sequence

<400> SEQUENCE: 23
tggtgtcaag tcttt                                                    15

<210> SEQ ID NO 24
<211> LENGTH: 15
<212> TYPE: DNA
<213> ORGANISM: Artificial Sequence
<220> FEATURE:
<223> OTHER INFORMATION: 1064-(15) base sequence

<400> SEQUENCE: 24
gcagagggtc ttgga                                                    15
```

<210> SEQ ID NO 25
<211> LENGTH: 15
<212> TYPE: DNA
<213> ORGANISM: Artificial Sequence
<220> FEATURE:
<223> OTHER INFORMATION: 1566-(15) base sequence

<400> SEQUENCE: 25
tgctggcata ggagg                                                      15

<210> SEQ ID NO 26
<211> LENGTH: 15
<212> TYPE: DNA
<213> ORGANISM: Artificial Sequence
<220> FEATURE:
<223> OTHER INFORMATION: 1582-(15) base sequence

<400> SEQUENCE: 26
tgactggagg atcgg                                                      15

<210> SEQ ID NO 27
<211> LENGTH: 15
<212> TYPE: DNA
<213> ORGANISM: Artificial Sequence
<220> FEATURE:
<223> OTHER INFORMATION: 1584-(15) base sequence

<400> SEQUENCE: 27
agtgactgga ggatc                                                      15

<210> SEQ ID NO 28
<211> LENGTH: 15
<212> TYPE: DNA
<213> ORGANISM: Artificial Sequence
<220> FEATURE:
<223> OTHER INFORMATION: 1633-(15) base sequence

<400> SEQUENCE: 28
cggctttggg tgtac                                                      15

<210> SEQ ID NO 29
<211> LENGTH: 15
<212> TYPE: DNA
<213> ORGANISM: Artificial Sequence
<220> FEATURE:
<223> OTHER INFORMATION: 1645-(15) base sequence

<400> SEQUENCE: 29
gaagaggtgg atcgg                                                      15

<210> SEQ ID NO 30
<211> LENGTH: 15
<212> TYPE: DNA
<213> ORGANISM: Artificial Sequence
<220> FEATURE:
<223> OTHER INFORMATION: 1689-(15) base sequence

<400> SEQUENCE: 30
acttggagga atagc                                                      15

<210> SEQ ID NO 31
<211> LENGTH: 15
<212> TYPE: DNA
<213> ORGANISM: Artificial Sequence
<220> FEATURE:

```
<223> OTHER INFORMATION: 1690-(15) base sequence

<400> SEQUENCE: 31
gacttggagg aatag                                                    15

<210> SEQ ID NO 32
<211> LENGTH: 15
<212> TYPE: DNA
<213> ORGANISM: Artificial Sequence
<220> FEATURE:
<223> OTHER INFORMATION: 1697-(15) base sequence

<400> SEQUENCE: 32
cttgccagac ttgga                                                    15

<210> SEQ ID NO 33
<211> LENGTH: 15
<212> TYPE: DNA
<213> ORGANISM: Artificial Sequence
<220> FEATURE:
<223> OTHER INFORMATION: 1858-(15) base sequence

<400> SEQUENCE: 33
tttctcatag gcgag                                                    15

<210> SEQ ID NO 34
<211> LENGTH: 15
<212> TYPE: DNA
<213> ORGANISM: Artificial Sequence
<220> FEATURE:
<223> OTHER INFORMATION: 1863-(15) base sequence

<400> SEQUENCE: 34
ggcgctttct catag                                                    15

<210> SEQ ID NO 35
<211> LENGTH: 15
<212> TYPE: DNA
<213> ORGANISM: Artificial Sequence
<220> FEATURE:
<223> OTHER INFORMATION: 2906-(15) base sequence

<400> SEQUENCE: 35
catgctgagg tattg                                                    15

<210> SEQ ID NO 36
<211> LENGTH: 15
<212> TYPE: DNA
<213> ORGANISM: Artificial Sequence
<220> FEATURE:
<223> OTHER INFORMATION: 3841-(15) base sequence

<400> SEQUENCE: 36
ggaaagattg ggtag                                                    15

<210> SEQ ID NO 37
<211> LENGTH: 15
<212> TYPE: DNA
<213> ORGANISM: Artificial Sequence
<220> FEATURE:
<223> OTHER INFORMATION: 3854-(15) base sequence

<400> SEQUENCE: 37
ggttgatagg atggg                                                    15
```

-continued

```
<210> SEQ ID NO 38
<211> LENGTH: 15
<212> TYPE: DNA
<213> ORGANISM: Artificial Sequence
<220> FEATURE:
<223> OTHER INFORMATION: 4810-(15) base sequence

<400> SEQUENCE: 38
acaagggatt tcgac                                                    15

<210> SEQ ID NO 39
<211> LENGTH: 15
<212> TYPE: DNA
<213> ORGANISM: Artificial Sequence
<220> FEATURE:
<223> OTHER INFORMATION: 5907-(15) base sequence

<400> SEQUENCE: 39
tggtgatctg tcata                                                    15

<210> SEQ ID NO 40
<211> LENGTH: 15
<212> TYPE: DNA
<213> ORGANISM: Artificial Sequence
<220> FEATURE:
<223> OTHER INFORMATION: 5908-(15) base sequence

<400> SEQUENCE: 40
ctggtgatct gtcat                                                    15

<210> SEQ ID NO 41
<211> LENGTH: 15
<212> TYPE: DNA
<213> ORGANISM: Artificial Sequence
<220> FEATURE:
<223> OTHER INFORMATION: 5950-(15) base sequence

<400> SEQUENCE: 41
ggatgttggt ttttg                                                    15

<210> SEQ ID NO 42
<211> LENGTH: 15
<212> TYPE: DNA
<213> ORGANISM: Artificial Sequence
<220> FEATURE:
<223> OTHER INFORMATION: 6015-(15) base sequence

<400> SEQUENCE: 42
agcgggaagg tcaaa                                                    15

<210> SEQ ID NO 43
<211> LENGTH: 15
<212> TYPE: DNA
<213> ORGANISM: Artificial Sequence
<220> FEATURE:
<223> OTHER INFORMATION: 6239-(15) base sequence

<400> SEQUENCE: 43 tcgttttac tttca                                                     15

<210> SEQ ID NO 44
<211> LENGTH: 15
<212> TYPE: DNA
<213> ORGANISM: Artificial Sequence
<220> FEATURE:
<223> OTHER INFORMATION: 6240-(15) base sequence
```

<400> SEQUENCE: 44 ttcgtttttta ctttc                                                       15

<210> SEQ ID NO 45
<211> LENGTH: 15
<212> TYPE: DNA
<213> ORGANISM: Artificial Sequence
<220> FEATURE:
<223> OTHER INFORMATION: 6302-(15) base sequence

<400> SEQUENCE: 45 aataggggggc tttga                                                       15

<210> SEQ ID NO 46
<211> LENGTH: 15
<212> TYPE: DNA
<213> ORGANISM: Artificial Sequence
<220> FEATURE:
<223> OTHER INFORMATION: 6448-(15) base sequence

<400> SEQUENCE: 46
aaatgaagtg atgcg                                                        15

<210> SEQ ID NO 47
<211> LENGTH: 15
<212> TYPE: DNA
<213> ORGANISM: Artificial Sequence
<220> FEATURE:
<223> OTHER INFORMATION: 6755-(15) base sequence

<400> SEQUENCE: 47
cataagtttc tcagc                                                        15

<210> SEQ ID NO 48
<211> LENGTH: 15
<212> TYPE: DNA
<213> ORGANISM: Artificial Sequence
<220> FEATURE:
<223> OTHER INFORMATION: 6870-(15) base sequence

<400> SEQUENCE: 48
acagcaacca cagat                                                        15

<210> SEQ ID NO 49
<211> LENGTH: 15
<212> TYPE: DNA
<213> ORGANISM: Artificial Sequence
<220> FEATURE:
<223> OTHER INFORMATION: 7057-(15) base sequence

<400> SEQUENCE: 49
ccaattctca atagc                                                        15

<210> SEQ ID NO 50
<211> LENGTH: 15
<212> TYPE: DNA
<213> ORGANISM: Artificial Sequence
<220> FEATURE:
<223> OTHER INFORMATION: 7060-(15) base sequence

<400> SEQUENCE: 50
ggaccaattc tcaat                                                        15

<210> SEQ ID NO 51
<211> LENGTH: 15

```
<212> TYPE: DNA
<213> ORGANISM: Artificial Sequence
<220> FEATURE:
<223> OTHER INFORMATION: 7130-(15) base sequence

<400> SEQUENCE: 51
gtgattctag cactc                                                    15

<210> SEQ ID NO 52
<211> LENGTH: 15
<212> TYPE: DNA
<213> ORGANISM: Artificial Sequence
<220> FEATURE:
<223> OTHER INFORMATION: 7131-(15) base sequence

<400> SEQUENCE: 52
ggtgattcta gcact                                                    15

<210> SEQ ID NO 53
<211> LENGTH: 15
<212> TYPE: DNA
<213> ORGANISM: Artificial Sequence
<220> FEATURE:
<223> OTHER INFORMATION: 7133-(15) base sequence

<400> SEQUENCE: 53
ttggtgattc tagca                                                    15

<210> SEQ ID NO 54
<211> LENGTH: 15
<212> TYPE: DNA
<213> ORGANISM: Artificial Sequence
<220> FEATURE:
<223> OTHER INFORMATION: 7134-(15) base sequence

<400> SEQUENCE: 54
cttggtgatt ctagc                                                    15

<210> SEQ ID NO 55
<211> LENGTH: 15
<212> TYPE: DNA
<213> ORGANISM: Artificial Sequence
<220> FEATURE:
<223> OTHER INFORMATION: 7135-(15) base sequence

<400> SEQUENCE: 55
gcttggtgat tctag                                                    15

<210> SEQ ID NO 56
<211> LENGTH: 15
<212> TYPE: DNA
<213> ORGANISM: Artificial Sequence
<220> FEATURE:
<223> OTHER INFORMATION: 7136-(15) base sequence

<400> SEQUENCE: 56
tgcttggtga ttcta                                                    15

<210> SEQ ID NO 57
<211> LENGTH: 15
<212> TYPE: DNA
<213> ORGANISM: Artificial Sequence
<220> FEATURE:
<223> OTHER INFORMATION: 7203-(15) base sequence

<400> SEQUENCE: 57
```

```
ccagtgtttt agttc                                                15

<210> SEQ ID NO 58
<211> LENGTH: 15
<212> TYPE: DNA
<213> ORGANISM: Artificial Sequence
<220> FEATURE:
<223> OTHER INFORMATION: 7365-(15) base sequence

<400> SEQUENCE: 58
aagatgaggc atagc                                                15

<210> SEQ ID NO 59
<211> LENGTH: 15
<212> TYPE: DNA
<213> ORGANISM: Artificial Sequence
<220> FEATURE:
<223> OTHER INFORMATION: 7373-(15) base sequence

<400> SEQUENCE: 59
ctcgttagaa gatga                                                15

<210> SEQ ID NO 60
<211> LENGTH: 15
<212> TYPE: DNA
<213> ORGANISM: Artificial Sequence
<220> FEATURE:
<223> OTHER INFORMATION: 7688-(15) base sequence

<400> SEQUENCE: 60
tatatgactg tggga                                                15

<210> SEQ ID NO 61
<211> LENGTH: 15
<212> TYPE: DNA
<213> ORGANISM: Artificial Sequence
<220> FEATURE:
<223> OTHER INFORMATION: 7733-(15) base sequence

<400> SEQUENCE: 61
caggatacaa gagtt                                                15

<210> SEQ ID NO 62
<211> LENGTH: 15
<212> TYPE: DNA
<213> ORGANISM: Artificial Sequence
<220> FEATURE:
<223> OTHER INFORMATION: 7734-(15) base sequence

<400> SEQUENCE: 62
ccaggataca agagt                                                15

<210> SEQ ID NO 63
<211> LENGTH: 15
<212> TYPE: DNA
<213> ORGANISM: Artificial Sequence
<220> FEATURE:
<223> OTHER INFORMATION: 7769-(15) base sequence

<400> SEQUENCE: 63
gagagaagtt caaac                                                15

<210> SEQ ID NO 64
<211> LENGTH: 15
<212> TYPE: DNA
<213> ORGANISM: Artificial Sequence
```

```
<220> FEATURE:
<223> OTHER INFORMATION: 7792-(15) base sequence

<400> SEQUENCE: 64
atgactttgg accac                                                      15

<210> SEQ ID NO 65
<211> LENGTH: 15
<212> TYPE: DNA
<213> ORGANISM: Artificial Sequence
<220> FEATURE:
<223> OTHER INFORMATION: 7794-(15) base sequence

<400> SEQUENCE: 65
tgatgacttt ggacc                                                      15

<210> SEQ ID NO 66
<211> LENGTH: 15
<212> TYPE: DNA
<213> ORGANISM: Artificial Sequence
<220> FEATURE:
<223> OTHER INFORMATION: 7827-(15) base sequence

<400> SEQUENCE: 66
cagggcaagg taagc                                                      15

<210> SEQ ID NO 67
<211> LENGTH: 15
<212> TYPE: DNA
<213> ORGANISM: Artificial Sequence
<220> FEATURE:
<223> OTHER INFORMATION: 7829-(15) base sequence

<400> SEQUENCE: 67
agcagggcaa ggtaa                                                      15

<210> SEQ ID NO 68
<211> LENGTH: 15
<212> TYPE: DNA
<213> ORGANISM: Artificial Sequence
<220> FEATURE:
<223> OTHER INFORMATION: 7859-(15) base sequence

<400> SEQUENCE: 68
tgggcatgtc aactc                                                      15

<210> SEQ ID NO 69
<211> LENGTH: 15
<212> TYPE: DNA
<213> ORGANISM: Artificial Sequence
<220> FEATURE:
<223> OTHER INFORMATION: 7860-(15) base sequence

<400> SEQUENCE: 69
ttgggcatgt caact                                                      15

<210> SEQ ID NO 70
<211> LENGTH: 15
<212> TYPE: DNA
<213> ORGANISM: Artificial Sequence
<220> FEATURE:
<223> OTHER INFORMATION: 8001-(15) base sequence

<400> SEQUENCE: 70
atgttggaca ttgag                                                      15
```

```
<210> SEQ ID NO 71
<211> LENGTH: 15
<212> TYPE: DNA
<213> ORGANISM: Artificial Sequence
<220> FEATURE:
<223> OTHER INFORMATION: 8165-(15) base sequence

<400> SEQUENCE: 71
atggccttgg ggtgc                                                       15

<210> SEQ ID NO 72
<211> LENGTH: 16
<212> TYPE: RNA
<213> ORGANISM: Homo sapiens
<220> FEATURE:
<221> NAME/KEY: misc_feature
<222> LOCATION: (1)..(16)
<223> OTHER INFORMATION: miR-4279

<400> SEQUENCE: 72
cucuccuccc ggcuuc                                                      16

<210> SEQ ID NO 73
<211> LENGTH: 18
<212> TYPE: RNA
<213> ORGANISM: Homo sapiens
<220> FEATURE:
<221> NAME/KEY: misc_feature
<222> LOCATION: (1)..(18)
<223> OTHER INFORMATION: miR-4419b

<400> SEQUENCE: 73
gaggcugaag gaagaugg                                                    18

<210> SEQ ID NO 74
<211> LENGTH: 17
<212> TYPE: RNA
<213> ORGANISM: Homo sapiens
<220> FEATURE:
<221> NAME/KEY: misc_feature
<222> LOCATION: (1)..(17)
<223> OTHER INFORMATION: miR-4516

<400> SEQUENCE: 74
gggagaaggg ucggggc                                                     17

<210> SEQ ID NO 75
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: miR-4635

<400> SEQUENCE: 75
ucuugaaguc agaacccgca a                                                21

<210> SEQ ID NO 76
<211> LENGTH: 15
<212> TYPE: DNA
<213> ORGANISM: Artificial Sequence
<220> FEATURE:
<223> OTHER INFORMATION: hnSR100L#1/hnSR100-712-LNA(15)
<220> FEATURE:
<221> NAME/KEY: modified_base
<222> LOCATION: (1)..(3)
<223> OTHER INFORMATION: 2',4'-BNA/LNA
```

```
<220> FEATURE:
<221> NAME/KEY: modified_base
<222> LOCATION: (3)..(3)
<223> OTHER INFORMATION: 5mC
<220> FEATURE:
<221> NAME/KEY: modified_base
<222> LOCATION: (13)..(14)
<223> OTHER INFORMATION: 2',4'-BNA/LNA

<400> SEQUENCE: 76 ttcttttct tcttt                                                    15

<210> SEQ ID NO 77
<211> LENGTH: 15
<212> TYPE: DNA
<213> ORGANISM: Artificial Sequence
<220> FEATURE:
<223> OTHER INFORMATION: hnSR100L#2/hnSR100-717-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA
<220> FEATURE:
<221> NAME/KEY: modified_base
<222> LOCATION: (14)..(14)
<223> OTHER INFORMATION: 5mC

<400> SEQUENCE: 77
atttcttctt tttct                                                   15

<210> SEQ ID NO 78
<211> LENGTH: 15
<212> TYPE: DNA
<213> ORGANISM: Artificial Sequence
<220> FEATURE:
<223> OTHER INFORMATION: hnSR100L#3/hnSR100-721-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 78
gtggatttct tcttt                                                   15

<210> SEQ ID NO 79
<211> LENGTH: 15
<212> TYPE: DNA
<213> ORGANISM: Artificial Sequence
<220> FEATURE:
<223> OTHER INFORMATION: hnSR100L#4/hnSR100-780-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (2)..(2)
<223> OTHER INFORMATION: 5mC
<220> FEATURE:
<221> NAME/KEY: modified_base
<222> LOCATION: (13)..(14)
<223> OTHER INFORMATION: 2',4'-BNA/LNA

<400> SEQUENCE: 79
```
tcttcttttt cttga                                                                15

<210> SEQ ID NO 80
<211> LENGTH: 15
<212> TYPE: DNA
<213> ORGANISM: Artificial Sequence
<220> FEATURE:
<223> OTHER INFORMATION: hnSR100L#5/hnSR100-783-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (2)..(2)
<223> OTHER INFORMATION: 5mC
<220> FEATURE:
<221> NAME/KEY: modified_base
<222> LOCATION: (13)..(14)
<223> OTHER INFORMATION: 2',4'-BNA/LNA
<220> FEATURE:
<221> NAME/KEY: modified_base
<222> LOCATION: (14)..(14)
<223> OTHER INFORMATION: 5mC

<400> SEQUENCE: 80
tcttcttctt tttct                                                                15

<210> SEQ ID NO 81
<211> LENGTH: 15
<212> TYPE: DNA
<213> ORGANISM: Artificial Sequence
<220> FEATURE:
<223> OTHER INFORMATION: hnSR100L#6/hnSR100-786-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 81
ttttcttctt ctttt                                                                15

<210> SEQ ID NO 82
<211> LENGTH: 15
<212> TYPE: DNA
<213> ORGANISM: Artificial Sequence
<220> FEATURE:
<223> OTHER INFORMATION: hnSR100L#7/hnSR100-1185-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 82
ttttggtaaa gaggt                                                                15

<210> SEQ ID NO 83
<211> LENGTH: 15
<212> TYPE: DNA
<213> ORGANISM: Artificial Sequence
<220> FEATURE:
<223> OTHER INFORMATION: hnSR100L#8/hnSR100-1389-LNA(15)
<220> FEATURE:
<221> NAME/KEY: modified_base

```
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 83
gtgaggaggt ggtga                                                    15

<210> SEQ ID NO 84
<211> LENGTH: 15
<212> TYPE: DNA
<213> ORGANISM: Artificial Sequence
<220> FEATURE:
<223> OTHER INFORMATION: hnSR100L#9/hnSR100-1518-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 84
gggctgtgga tggga                                                    15

<210> SEQ ID NO 85
<211> LENGTH: 15
<212> TYPE: DNA
<213> ORGANISM: Artificial Sequence
<220> FEATURE:
<223> OTHER INFORMATION: hnSR100L#10/hnSR100-1660-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA
<220> FEATURE:
<221> NAME/KEY: modified_base
<222> LOCATION: (14)..(14)
<223> OTHER INFORMATION: 5mC

<400> SEQUENCE: 85
taggaccttt tttca                                                    15

<210> SEQ ID NO 86
<211> LENGTH: 15
<212> TYPE: DNA
<213> ORGANISM: Artificial Sequence
<220> FEATURE:
<223> OTHER INFORMATION: hnSR100L#11/hnSR100-1663-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 86
gagtaggacc ttttt                                                    15

<210> SEQ ID NO 87
<211> LENGTH: 15
<212> TYPE: DNA
```

```
<213> ORGANISM: Artificial Sequence
<220> FEATURE:
<223> OTHER INFORMATION: hnSR100L#12/hnSR100-3590-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 87
gtttatttta aggat                                                15

<210> SEQ ID NO 88
<211> LENGTH: 15
<212> TYPE: DNA
<213> ORGANISM: Artificial Sequence
<220> FEATURE:
<223> OTHER INFORMATION: hnSR100L#13/hnSR100-3593-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 88
agagtttatt ttaag                                                15

<210> SEQ ID NO 89
<211> LENGTH: 15
<212> TYPE: DNA
<213> ORGANISM: Artificial Sequence
<220> FEATURE:
<223> OTHER INFORMATION: hnSR100L#14/hnSR100-3844-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 89
atgggaaaga ttggg                                                15

<210> SEQ ID NO 90
<211> LENGTH: 15
<212> TYPE: DNA
<213> ORGANISM: Artificial Sequence
<220> FEATURE:
<223> OTHER INFORMATION: hnSR100L#15/hnSR100-3847-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 90
aggatgggaa agatt                                                15

<210> SEQ ID NO 91
<211> LENGTH: 15
```

```
<212> TYPE: DNA
<213> ORGANISM: Artificial Sequence
<220> FEATURE:
<223> OTHER INFORMATION: hnSR100L#16/hnSR100-4291-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 91
taaataaaaa ggttt                                                    15

<210> SEQ ID NO 92
<211> LENGTH: 15
<212> TYPE: DNA
<213> ORGANISM: Artificial Sequence
<220> FEATURE:
<223> OTHER INFORMATION: hnSR100L#17/hnSR100-4294-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 92
aaataaataa aaagg                                                    15

<210> SEQ ID NO 93
<211> LENGTH: 15
<212> TYPE: DNA
<213> ORGANISM: Artificial Sequence
<220> FEATURE:
<223> OTHER INFORMATION: hnSR100L#18/hnSR100-4297-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 93
ataaaataaa taaaa                                                    15

<210> SEQ ID NO 94
<211> LENGTH: 15
<212> TYPE: DNA
<213> ORGANISM: Artificial Sequence
<220> FEATURE:
<223> OTHER INFORMATION: hnSR100L#19/hnSR100-4367-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA
<220> FEATURE:
<221> NAME/KEY: modified_base
<222> LOCATION: (13)..(13)
<223> OTHER INFORMATION: 5mC

<400> SEQUENCE: 94
```
aaataaataa ttcaa                                              15

<210> SEQ ID NO 95
<211> LENGTH: 15
<212> TYPE: DNA
<213> ORGANISM: Artificial Sequence
<220> FEATURE:
<223> OTHER INFORMATION: hnSR100L#20/hnSR100-4370-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 95
tataaataaa taatt                                              15

<210> SEQ ID NO 96
<211> LENGTH: 15
<212> TYPE: DNA
<213> ORGANISM: Artificial Sequence
<220> FEATURE:
<223> OTHER INFORMATION: hnSR100L#21/hnSR100-7174-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 96
ttgtgtgact gaagc                                              15

<210> SEQ ID NO 97
<211> LENGTH: 15
<212> TYPE: DNA
<213> ORGANISM: Artificial Sequence
<220> FEATURE:
<223> OTHER INFORMATION: hnSR100L#22/hnSR100-7177-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 97
aatttgtgtg actga                                              15

<210> SEQ ID NO 98
<211> LENGTH: 15
<212> TYPE: DNA
<213> ORGANISM: Homo sapiens

<400> SEQUENCE: 98
gcttcagtca cacaa                                              15

<210> SEQ ID NO 99
<211> LENGTH: 15
<212> TYPE: RNA
<213> ORGANISM: Homo sapiens

<400> SEQUENCE: 99

-continued gcuucaguca cacaa                                                    15

<210> SEQ ID NO 100
<211> LENGTH: 15
<212> TYPE: DNA
<213> ORGANISM: Artificial Sequence
<220> FEATURE:
<223> OTHER INFORMATION: NEG#26LNA
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 100
tgaacaaaat aatac                                                    15

<210> SEQ ID NO 101
<211> LENGTH: 21
<212> TYPE: DNA
<213> ORGANISM: Artificial Sequence
<220> FEATURE:
<223> OTHER INFORMATION: Primer for hnSR100: Set1-Fw

<400> SEQUENCE: 101
tgacaaagac ttgacaccac c                                             21

<210> SEQ ID NO 102
<211> LENGTH: 19
<212> TYPE: DNA
<213> ORGANISM: Artificial Sequence
<220> FEATURE:
<223> OTHER INFORMATION: Primer for hnSR100: Set1-Rv

<400> SEQUENCE: 102
acctgcgtcg cttgtgttt                                                19

<210> SEQ ID NO 103
<211> LENGTH: 20
<212> TYPE: DNA
<213> ORGANISM: Artificial Sequence
<220> FEATURE:
<223> OTHER INFORMATION: Primer for hnSR100: Set2-Fw

<400> SEQUENCE: 103
ctcctcaccc cagaacaagg                                               20

<210> SEQ ID NO 104
<211> LENGTH: 20
<212> TYPE: DNA
<213> ORGANISM: Artificial Sequence
<220> FEATURE:
<223> OTHER INFORMATION: Primer for hnSR100: Set2-Rv

<400> SEQUENCE: 104
ggatgggacc aaactggact                                               20

<210> SEQ ID NO 105
<211> LENGTH: 20
<212> TYPE: DNA
<213> ORGANISM: Artificial Sequence
<220> FEATURE:
<223> OTHER INFORMATION: Primer for Gapdh: Set1-Fw

```
<400> SEQUENCE: 105
gagtcaacgg atttggtcgt                                              20

<210> SEQ ID NO 106
<211> LENGTH: 20
<212> TYPE: DNA
<213> ORGANISM: Artificial Sequence
<220> FEATURE:
<223> OTHER INFORMATION: Primer for Gapdh: Set1-Rv

<400> SEQUENCE: 106
gacaagcttc ccgttctcag                                              20

<210> SEQ ID NO 107
<211> LENGTH: 20
<212> TYPE: DNA
<213> ORGANISM: Artificial Sequence
<220> FEATURE:
<223> OTHER INFORMATION: actin-set1-Fw

<400> SEQUENCE: 107
ggccgtcttc ccctccatcg                                              20

<210> SEQ ID NO 108
<211> LENGTH: 22
<212> TYPE: DNA
<213> ORGANISM: Artificial Sequence
<220> FEATURE:
<223> OTHER INFORMATION: actin-set1-Rv

<400> SEQUENCE: 108
ccagttggtg acgatgccgt gc                                           22

<210> SEQ ID NO 109
<211> LENGTH: 17
<212> TYPE: DNA
<213> ORGANISM: Artificial Sequence
<220> FEATURE:
<223> OTHER INFORMATION: hnSR100-784-LNA(17)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (15)..(16)
<223> OTHER INFORMATION: 2',4'-BNA/LNA

<400> SEQUENCE: 109
ttttcttctt ctttttc                                                 17

<210> SEQ ID NO 110
<211> LENGTH: 19
<212> TYPE: DNA
<213> ORGANISM: Artificial Sequence
<220> FEATURE:
<223> OTHER INFORMATION: hnSR100-782-LNA(19)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (17)..(18)
<223> OTHER INFORMATION: 2',4'-BNA/LNA
<220> FEATURE:
<221> NAME/KEY: modified_base
<222> LOCATION: (17)..(17)
<223> OTHER INFORMATION: 5mC
```

<400> SEQUENCE: 110
ttttcttctt cttttcttt                                        19

<210> SEQ ID NO 111
<211> LENGTH: 15
<212> TYPE: DNA
<213> ORGANISM: Artificial Sequence
<220> FEATURE:
<223> OTHER INFORMATION: hnSR100-784-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (3)..(3)
<223> OTHER INFORMATION: 5mC
<220> FEATURE:
<221> NAME/KEY: modified_base
<222> LOCATION: (13)..(14)
<223> OTHER INFORMATION: 2',4'-BNA/LNA

<400> SEQUENCE: 111
ttcttcttct ttttc                                            15

<210> SEQ ID NO 112
<211> LENGTH: 17
<212> TYPE: DNA
<213> ORGANISM: Artificial Sequence
<220> FEATURE:
<223> OTHER INFORMATION: hnSR100-782-LNA(17)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (3)..(3)
<223> OTHER INFORMATION: 5mC
<220> FEATURE:
<221> NAME/KEY: modified_base
<222> LOCATION: (15)..(16)
<223> OTHER INFORMATION: 2',4'-BNA/LNA
<220> FEATURE:
<221> NAME/KEY: modified_base
<222> LOCATION: (15)..(15)
<223> OTHER INFORMATION: 5mC

<400> SEQUENCE: 112
ttcttcttct ttttctt                                          17

<210> SEQ ID NO 113
<211> LENGTH: 19
<212> TYPE: DNA
<213> ORGANISM: Artificial Sequence
<220> FEATURE:
<223> OTHER INFORMATION: hnSR100-780-LNA(19)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (3)..(3)
<223> OTHER INFORMATION: 5mC
<220> FEATURE:
<221> NAME/KEY: modified_base
<222> LOCATION: (17)..(18)
<223> OTHER INFORMATION: 2',4'-BNA/LNA

<400> SEQUENCE: 113
ttcttcttct ttttcttga                                        19

<210> SEQ ID NO 114
<211> LENGTH: 15
<212> TYPE: DNA
<213> ORGANISM: Artificial Sequence
<220> FEATURE:
<223> OTHER INFORMATION: hnSR100-782-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (1)..(1)
<223> OTHER INFORMATION: 5mC
<220> FEATURE:
<221> NAME/KEY: modified_base
<222> LOCATION: (13)..(14)
<223> OTHER INFORMATION: 2',4'-BNA/LNA
<220> FEATURE:
<221> NAME/KEY: modified_base
<222> LOCATION: (13)..(13)
<223> OTHER INFORMATION: 5mC

<400> SEQUENCE: 114
cttcttcttt ttctt                                            15

<210> SEQ ID NO 115
<211> LENGTH: 17
<212> TYPE: DNA
<213> ORGANISM: Artificial Sequence
<220> FEATURE:
<223> OTHER INFORMATION: hnSR100-780-LNA(17)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (1)..(1)
<223> OTHER INFORMATION: 5mC
<220> FEATURE:
<221> NAME/KEY: modified_base
<222> LOCATION: (15)..(16)
<223> OTHER INFORMATION: 2',4'-BNA/LNA

<400> SEQUENCE: 115
cttcttcttt ttcttga                                          17

<210> SEQ ID NO 116
<211> LENGTH: 19
<212> TYPE: DNA
<213> ORGANISM: Artificial Sequence
<220> FEATURE:
<223> OTHER INFORMATION: hnSR100-778-LNA(19)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (1)..(1)
<223> OTHER INFORMATION: 5mC
<220> FEATURE:
<221> NAME/KEY: modified_base
<222> LOCATION: (17)..(18)
<223> OTHER INFORMATION: 2',4'-BNA/LNA
<220> FEATURE:
<221> NAME/KEY: modified_base
<222> LOCATION: (18)..(18)
<223> OTHER INFORMATION: 5mC

<400> SEQUENCE: 116
cttcttcttt ttcttgaca                                              19

<210> SEQ ID NO 117
<211> LENGTH: 15
<212> TYPE: DNA
<213> ORGANISM: Artificial Sequence
<220> FEATURE:
<223> OTHER INFORMATION: hnSR100-788-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (2)..(2)
<223> OTHER INFORMATION: 5mC
<220> FEATURE:
<221> NAME/KEY: modified_base
<222> LOCATION: (13)..(14)
<223> OTHER INFORMATION: 2',4'-BNA/LNA
<220> FEATURE:
<221> NAME/KEY: modified_base
<222> LOCATION: (13)..(13)
<223> OTHER INFORMATION: 5mC

<400> SEQUENCE: 117
acttttcttc ttctt                                                  15

<210> SEQ ID NO 118
<211> LENGTH: 17
<212> TYPE: DNA
<213> ORGANISM: Artificial Sequence
<220> FEATURE:
<223> OTHER INFORMATION: hnSR100-786-LNA(17)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (2)..(2)
<223> OTHER INFORMATION: 5mC
<220> FEATURE:
<221> NAME/KEY: modified_base
<222> LOCATION: (15)..(16)
<223> OTHER INFORMATION: 2',4'-BNA/LNA

<400> SEQUENCE: 118
acttttcttc ttctttt                                                17

<210> SEQ ID NO 119
<211> LENGTH: 19
<212> TYPE: DNA
<213> ORGANISM: Artificial Sequence
<220> FEATURE:
<223> OTHER INFORMATION: hnSR100-784-LNA(19)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (2)..(2)
<223> OTHER INFORMATION: 5mC
<220> FEATURE:
<221> NAME/KEY: modified_base
<222> LOCATION: (17)..(18)
<223> OTHER INFORMATION: 2',4'-BNA/LNA

<400> SEQUENCE: 119
acttttcttc ttctttttc                                              19

```
<210> SEQ ID NO 120
<211> LENGTH: 15
<212> TYPE: DNA
<213> ORGANISM: Artificial Sequence
<220> FEATURE:
<223> OTHER INFORMATION: hnSR100-790-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 120
gaacttttct tcttc                                                    15

<210> SEQ ID NO 121
<211> LENGTH: 17
<212> TYPE: DNA
<213> ORGANISM: Artificial Sequence
<220> FEATURE:
<223> OTHER INFORMATION: hnSR100-788-LNA(17)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (15)..(16)
<223> OTHER INFORMATION: 2',4'-BNA/LNA
<220> FEATURE:
<221> NAME/KEY: modified_base
<222> LOCATION: (15)..(15)
<223> OTHER INFORMATION: 5mC

<400> SEQUENCE: 121
gaacttttct tcttctt                                                  17

<210> SEQ ID NO 122
<211> LENGTH: 19
<212> TYPE: DNA
<213> ORGANISM: Artificial Sequence
<220> FEATURE:
<223> OTHER INFORMATION: hnSR100-786-LNA(19)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (17)..(18)
<223> OTHER INFORMATION: 2',4'-BNA/LNA

<400> SEQUENCE: 122
gaacttttct tcttctttt                                                19

<210> SEQ ID NO 123
<211> LENGTH: 17
<212> TYPE: DNA
<213> ORGANISM: Artificial Sequence
<220> FEATURE:
<223> OTHER INFORMATION: hnSR100-7172-LNA(17)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (15)..(16)
<223> OTHER INFORMATION: 2',4'-BNA/LNA
```

```
<220> FEATURE:
<221> NAME/KEY: modified_base
<222> LOCATION: (15)..(16)
<223> OTHER INFORMATION: 5mC

<400> SEQUENCE: 123
ttgtgtgact gaagcct                                                      17

<210> SEQ ID NO 124
<211> LENGTH: 19
<212> TYPE: DNA
<213> ORGANISM: Artificial Sequence
<220> FEATURE:
<223> OTHER INFORMATION: hnSR100-7170-LNA(19)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (17)..(18)
<223> OTHER INFORMATION: 2',4'-BNA/LNA
<220> FEATURE:
<221> NAME/KEY: modified_base
<222> LOCATION: (18)..(18)
<223> OTHER INFORMATION: 5mC

<400> SEQUENCE: 124
ttgtgtgact gaagcctcc                                                    19

<210> SEQ ID NO 125
<211> LENGTH: 15
<212> TYPE: DNA
<213> ORGANISM: Artificial Sequence
<220> FEATURE:
<223> OTHER INFORMATION: hnSR100-7172-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA
<220> FEATURE:
<221> NAME/KEY: modified_base
<222> LOCATION: (13)..(14)
<223> OTHER INFORMATION: 5mC

<400> SEQUENCE: 125
gtgtgactga agcct                                                        15

<210> SEQ ID NO 126
<211> LENGTH: 17
<212> TYPE: DNA
<213> ORGANISM: Artificial Sequence
<220> FEATURE:
<223> OTHER INFORMATION: hnSR100-7170-LNA(17)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (15)..(16)
<223> OTHER INFORMATION: 2',4'-BNA/LNA
<220> FEATURE:
<221> NAME/KEY: modified_base
<222> LOCATION: (16)..(16)
<223> OTHER INFORMATION: 5mC

<400> SEQUENCE: 126
```
gtgtgactga agcctcc                                                                                    17

<210> SEQ ID NO 127
<211> LENGTH: 19
<212> TYPE: DNA
<213> ORGANISM: Artificial Sequence
<220> FEATURE:
<223> OTHER INFORMATION: hnSR100-7168-LNA(19)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (17)..(18)
<223> OTHER INFORMATION: 2',4'-BNA/LNA
<220> FEATURE:
<221> NAME/KEY: modified_base
<222> LOCATION: (17)..(17)
<223> OTHER INFORMATION: 5mC

<400> SEQUENCE: 127
gtgtgactga agcctccat                                                                                  19

<210> SEQ ID NO 128
<211> LENGTH: 15
<212> TYPE: DNA
<213> ORGANISM: Artificial Sequence
<220> FEATURE:
<223> OTHER INFORMATION: hnSR100-7170-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA
<220> FEATURE:
<221> NAME/KEY: modified_base
<222> LOCATION: (14)..(14)
<223> OTHER INFORMATION: 5mC

<400> SEQUENCE: 128
gtgactgaag cctcc                                                                                      15

<210> SEQ ID NO 129
<211> LENGTH: 17
<212> TYPE: DNA
<213> ORGANISM: Artificial Sequence
<220> FEATURE:
<223> OTHER INFORMATION: hnSR100-7168-LNA(17)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (15)..(16)
<223> OTHER INFORMATION: 2',4'-BNA/LNA
<220> FEATURE:
<221> NAME/KEY: modified_base
<222> LOCATION: (15)..(15)
<223> OTHER INFORMATION: 5mC

<400> SEQUENCE: 129
gtgactgaag cctccat                                                                                    17

<210> SEQ ID NO 130
<211> LENGTH: 19
<212> TYPE: DNA
<213> ORGANISM: Artificial Sequence

```
<220> FEATURE:
<223> OTHER INFORMATION: hnSR100-7166-LNA(19)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (17)..(18)
<223> OTHER INFORMATION: 2',4'-BNA/LNA

<400> SEQUENCE: 130
gtgactgaag cctccattt                                                19

<210> SEQ ID NO 131
<211> LENGTH: 15
<212> TYPE: DNA
<213> ORGANISM: Artificial Sequence
<220> FEATURE:
<223> OTHER INFORMATION: hnSR100-7176-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 131
atttgtgtga ctgaa                                                    15

<210> SEQ ID NO 132
<211> LENGTH: 17
<212> TYPE: DNA
<213> ORGANISM: Artificial Sequence
<220> FEATURE:
<223> OTHER INFORMATION: hnSR100-7174-LNA(17)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (15)..(16)
<223> OTHER INFORMATION: 2',4'-BNA/LNA

<400> SEQUENCE: 132
atttgtgtga ctgaagc                                                  17

<210> SEQ ID NO 133
<211> LENGTH: 19
<212> TYPE: DNA
<213> ORGANISM: Artificial Sequence
<220> FEATURE:
<223> OTHER INFORMATION: hnSR100-7172-LNA(19)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (17)..(18)
<223> OTHER INFORMATION: 2',4'-BNA/LNA
<220> FEATURE:
<221> NAME/KEY: modified_base
<222> LOCATION: (17)..(18)
<223> OTHER INFORMATION: 5mC

<400> SEQUENCE: 133
atttgtgtga ctgaagcct                                                19
```

```
<210> SEQ ID NO 134
<211> LENGTH: 15
<212> TYPE: DNA
<213> ORGANISM: Artificial Sequence
<220> FEATURE:
<223> OTHER INFORMATION: hnSR100-7178-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA
<220> FEATURE:
<221> NAME/KEY: modified_base
<222> LOCATION: (13)..(13)
<223> OTHER INFORMATION: 5mC

<400> SEQUENCE: 134
taatttgtgt gactg                                                  15

<210> SEQ ID NO 135
<211> LENGTH: 17
<212> TYPE: DNA
<213> ORGANISM: Artificial Sequence
<220> FEATURE:
<223> OTHER INFORMATION: hnSR100-7176-LNA(17)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (15)..(16)
<223> OTHER INFORMATION: 2',4'-BNA/LNA

<400> SEQUENCE: 135
taatttgtgt gactgaa                                                17

<210> SEQ ID NO 136
<211> LENGTH: 19
<212> TYPE: DNA
<213> ORGANISM: Artificial Sequence
<220> FEATURE:
<223> OTHER INFORMATION: hnSR100-7174-LNA(19)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (17)..(18)
<223> OTHER INFORMATION: 2',4'-BNA/LNA

<400> SEQUENCE: 136
taatttgtgt gactgaagc                                              19

<210> SEQ ID NO 137
<211> LENGTH: 15
<212> TYPE: DNA
<213> ORGANISM: Artificial Sequence
<220> FEATURE:
<223> OTHER INFORMATION: hnSR100-786-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA
```

```
<400> SEQUENCE: 137
ttttcttctt ctttt                                                    15

<210> SEQ ID NO 138
<211> LENGTH: 17
<212> TYPE: DNA
<213> ORGANISM: Artificial Sequence
<220> FEATURE:
<223> OTHER INFORMATION: hnSR100-784-AmNA(17)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (15)..(16)
<223> OTHER INFORMATION: AmNA

<400> SEQUENCE: 138
ttttcttctt cttttc                                                   17

<210> SEQ ID NO 139
<211> LENGTH: 19
<212> TYPE: DNA
<213> ORGANISM: Artificial Sequence
<220> FEATURE:
<223> OTHER INFORMATION: hnSR100-782-AmNA(19)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (17)..(18)
<223> OTHER INFORMATION: AmNA
<220> FEATURE:
<221> NAME/KEY: modified_base
<222> LOCATION: (17)..(17)
<223> OTHER INFORMATION: 5mC

<400> SEQUENCE: 139
ttttcttctt cttttctt                                                 19

<210> SEQ ID NO 140
<211> LENGTH: 15
<212> TYPE: DNA
<213> ORGANISM: Artificial Sequence
<220> FEATURE:
<223> OTHER INFORMATION: hnSR100-784-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (3)..(3)
<223> OTHER INFORMATION: 5mC
<220> FEATURE:
<221> NAME/KEY: modified_base
<222> LOCATION: (13)..(14)
<223> OTHER INFORMATION: AmNA

<400> SEQUENCE: 140
ttcttcttct tttc                                                     15

<210> SEQ ID NO 141
<211> LENGTH: 17
<212> TYPE: DNA
<213> ORGANISM: Artificial Sequence
<220> FEATURE:
```

```
<223> OTHER INFORMATION: hnSR100-782-AmNA(17)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (3)..(3)
<223> OTHER INFORMATION: 5mC
<220> FEATURE:
<221> NAME/KEY: modified_base
<222> LOCATION: (15)..(16)
<223> OTHER INFORMATION: AmNA
<220> FEATURE:
<221> NAME/KEY: modified_base
<222> LOCATION: (15)..(15)
<223> OTHER INFORMATION: 5mC

<400> SEQUENCE: 141
ttcttcttct ttttctt                                              17

<210> SEQ ID NO 142
<211> LENGTH: 19
<212> TYPE: DNA
<213> ORGANISM: Artificial Sequence
<220> FEATURE:
<223> OTHER INFORMATION: hnSR100-780-AmNA(19)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (3)..(3)
<223> OTHER INFORMATION: 5mC
<220> FEATURE:
<221> NAME/KEY: modified_base
<222> LOCATION: (17)..(18)
<223> OTHER INFORMATION: AmNA

<400> SEQUENCE: 142
ttcttcttct ttttcttga                                            19

<210> SEQ ID NO 143
<211> LENGTH: 15
<212> TYPE: DNA
<213> ORGANISM: Artificial Sequence
<220> FEATURE:
<223> OTHER INFORMATION: hnSR100-782-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (1)..(1)
<223> OTHER INFORMATION: 5mC
<220> FEATURE:
<221> NAME/KEY: modified_base
<222> LOCATION: (13)..(14)
<223> OTHER INFORMATION: AmNA
<220> FEATURE:
<221> NAME/KEY: modified_base
<222> LOCATION: (13)..(13)
<223> OTHER INFORMATION: 5mC

<400> SEQUENCE: 143
cttcttcttt ttctt                                                15

<210> SEQ ID NO 144
<211> LENGTH: 17
<212> TYPE: DNA
<213> ORGANISM: Artificial Sequence
```

```
<220> FEATURE:
<223> OTHER INFORMATION: hnSR100-780-AmNA(17)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (1)..(1)
<223> OTHER INFORMATION: 5mC
<220> FEATURE:
<221> NAME/KEY: modified_base
<222> LOCATION: (15)..(16)
<223> OTHER INFORMATION: AmNA

<400> SEQUENCE: 144
cttcttcttt ttcttga                                                17

<210> SEQ ID NO 145
<211> LENGTH: 19
<212> TYPE: DNA
<213> ORGANISM: Artificial Sequence
<220> FEATURE:
<223> OTHER INFORMATION: hnSR100-778-AmNA(19)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (1)..(1)
<223> OTHER INFORMATION: 5mC
<220> FEATURE:
<221> NAME/KEY: modified_base
<222> LOCATION: (17)..(18)
<223> OTHER INFORMATION: AmNA
<220> FEATURE:
<221> NAME/KEY: modified_base
<222> LOCATION: (18)..(18)
<223> OTHER INFORMATION: 5mC

<400> SEQUENCE: 145
cttcttcttt ttcttgaca                                              19

<210> SEQ ID NO 146
<211> LENGTH: 15
<212> TYPE: DNA
<213> ORGANISM: Artificial Sequence
<220> FEATURE:
<223> OTHER INFORMATION: hnSR100-788-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (2)..(2)
<223> OTHER INFORMATION: 5mC
<220> FEATURE:
<221> NAME/KEY: modified_base
<222> LOCATION: (13)..(14)
<223> OTHER INFORMATION: AmNA
<220> FEATURE:
<221> NAME/KEY: modified_base
<222> LOCATION: (13)..(13)
<223> OTHER INFORMATION: 5mC

<400> SEQUENCE: 146
acttttcttc ttctt                                                  15

<210> SEQ ID NO 147
<211> LENGTH: 17
<212> TYPE: DNA
```

```
<213> ORGANISM: Artificial Sequence
<220> FEATURE:
<223> OTHER INFORMATION: hnSR100-786-AmNA(17)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (2)..(2)
<223> OTHER INFORMATION: 5mC
<220> FEATURE:
<221> NAME/KEY: modified_base
<222> LOCATION: (15)..(16)
<223> OTHER INFORMATION: AmNA

<400> SEQUENCE: 147
acttttcttc ttcttt                                                   17

<210> SEQ ID NO 148
<211> LENGTH: 19
<212> TYPE: DNA
<213> ORGANISM: Artificial Sequence
<220> FEATURE:
<223> OTHER INFORMATION: hnSR100-784-AmNA(19)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (2)..(2)
<223> OTHER INFORMATION: 5mC
<220> FEATURE:
<221> NAME/KEY: modified_base
<222> LOCATION: (17)..(18)
<223> OTHER INFORMATION: AmNA

<400> SEQUENCE: 148
acttttcttc ttcttttc                                                 19

<210> SEQ ID NO 149
<211> LENGTH: 15
<212> TYPE: DNA
<213> ORGANISM: Artificial Sequence
<220> FEATURE:
<223> OTHER INFORMATION: hnSR100-790-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA

<400> SEQUENCE: 149
gaacttttct tcttc                                                    15

<210> SEQ ID NO 150
<211> LENGTH: 17
<212> TYPE: DNA
<213> ORGANISM: Artificial Sequence
<220> FEATURE:
<223> OTHER INFORMATION: hnSR100-788-AmNA(17)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (15)..(16)
<223> OTHER INFORMATION: AmNA
```

```
<220> FEATURE:
<221> NAME/KEY: modified_base
<222> LOCATION: (15)..(15)
<223> OTHER INFORMATION: 5mC

<400> SEQUENCE: 150
gaacttttct tcttctt                                                    17

<210> SEQ ID NO 151
<211> LENGTH: 19
<212> TYPE: DNA
<213> ORGANISM: Artificial Sequence
<220> FEATURE:
<223> OTHER INFORMATION: hnSR100-786-AmNA(19)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (17)..(18)
<223> OTHER INFORMATION: AmNA

<400> SEQUENCE: 151
gaacttttct tcttctttt                                                  19

<210> SEQ ID NO 152
<211> LENGTH: 15
<212> TYPE: DNA
<213> ORGANISM: Artificial Sequence
<220> FEATURE:
<223> OTHER INFORMATION: hnSR100-7174-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA

<400> SEQUENCE: 152
ttgtgtgact gaagc                                                      15

<210> SEQ ID NO 153
<211> LENGTH: 17
<212> TYPE: DNA
<213> ORGANISM: Artificial Sequence
<220> FEATURE:
<223> OTHER INFORMATION: hnSR100-7172-AmNA(17)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (15)..(16)
<223> OTHER INFORMATION: 5mC
<220> FEATURE:
<221> NAME/KEY: modified_base
<222> LOCATION: (15)..(16)
<223> OTHER INFORMATION: AmNA

<400> SEQUENCE: 153
ttgtgtgact gaagcct                                                    17

<210> SEQ ID NO 154
<211> LENGTH: 19
<212> TYPE: DNA
<213> ORGANISM: Artificial Sequence
<220> FEATURE:
```

```
<223> OTHER INFORMATION: hnSR100-7170-AmNA(19)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (17)..(18)
<223> OTHER INFORMATION: AmNA
<220> FEATURE:
<221> NAME/KEY: modified_base
<222> LOCATION: (18)..(18)
<223> OTHER INFORMATION: 5mC

<400> SEQUENCE: 154
ttgtgtgact gaagcctcc                                             19

<210> SEQ ID NO 155
<211> LENGTH: 15
<212> TYPE: DNA
<213> ORGANISM: Artificial Sequence
<220> FEATURE:
<223> OTHER INFORMATION: hnSR100-7172-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA
<220> FEATURE:
<221> NAME/KEY: modified_base
<222> LOCATION: (13)..(14)
<223> OTHER INFORMATION: 5mC

<400> SEQUENCE: 155
gtgtgactga agcct                                                 15

<210> SEQ ID NO 156
<211> LENGTH: 17
<212> TYPE: DNA
<213> ORGANISM: Artificial Sequence
<220> FEATURE:
<223> OTHER INFORMATION: hnSR100-7170-AmNA(17)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (15)..(16)
<223> OTHER INFORMATION: AmNA
<220> FEATURE:
<221> NAME/KEY: modified_base
<222> LOCATION: (16)..(16)
<223> OTHER INFORMATION: 5mC

<400> SEQUENCE: 156
gtgtgactga agcctcc                                               17

<210> SEQ ID NO 157
<211> LENGTH: 19
<212> TYPE: DNA
<213> ORGANISM: Artificial Sequence
<220> FEATURE:
<223> OTHER INFORMATION: hnSR100-7168-AmNA(19)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
```

<222> LOCATION: (17)..(18)
<223> OTHER INFORMATION: AmNA
<220> FEATURE:
<221> NAME/KEY: modified_base
<222> LOCATION: (17)..(17)
<223> OTHER INFORMATION: 5mC

<400> SEQUENCE: 157
gtgtgactga agcctccat                                            19

<210> SEQ ID NO 158
<211> LENGTH: 15
<212> TYPE: DNA
<213> ORGANISM: Artificial Sequence
<220> FEATURE:
<223> OTHER INFORMATION: hnSR100-7170-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA
<220> FEATURE:
<221> NAME/KEY: modified_base
<222> LOCATION: (14)..(14)
<223> OTHER INFORMATION: 5mC

<400> SEQUENCE: 158
gtgactgaag cctcc                                                15

<210> SEQ ID NO 159
<211> LENGTH: 17
<212> TYPE: DNA
<213> ORGANISM: Artificial Sequence
<220> FEATURE:
<223> OTHER INFORMATION: hnSR100-7168-AmNA(17)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (15)..(16)
<223> OTHER INFORMATION: AmNA
<220> FEATURE:
<221> NAME/KEY: modified_base
<222> LOCATION: (15)..(15)
<223> OTHER INFORMATION: 5mC

<400> SEQUENCE: 159
gtgactgaag cctccat                                              17

<210> SEQ ID NO 160
<211> LENGTH: 19
<212> TYPE: DNA
<213> ORGANISM: Artificial Sequence
<220> FEATURE:
<223> OTHER INFORMATION: hnSR100-7166-AmNA(19)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (17)..(18)
<223> OTHER INFORMATION: AmNA

<400> SEQUENCE: 160
gtgactgaag cctccattt                                            19

```
<210> SEQ ID NO 161
<211> LENGTH: 15
<212> TYPE: DNA
<213> ORGANISM: Artificial Sequence
<220> FEATURE:
<223> OTHER INFORMATION: hnSR100-7176-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA

<400> SEQUENCE: 161
atttgtgtga ctgaa                                               15

<210> SEQ ID NO 162
<211> LENGTH: 17
<212> TYPE: DNA
<213> ORGANISM: Artificial Sequence
<220> FEATURE:
<223> OTHER INFORMATION: hnSR100-7174-AmNA(17)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (15)..(16)
<223> OTHER INFORMATION: AmNA

<400> SEQUENCE: 162
atttgtgtga ctgaagc                                             17

<210> SEQ ID NO 163
<211> LENGTH: 19
<212> TYPE: DNA
<213> ORGANISM: Artificial Sequence
<220> FEATURE:
<223> OTHER INFORMATION: hnSR100-7172-AmNA(19)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (17)..(18)
<223> OTHER INFORMATION: AmNA
<220> FEATURE:
<221> NAME/KEY: modified_base
<222> LOCATION: (17)..(18)
<223> OTHER INFORMATION: 5mC

<400> SEQUENCE: 163
atttgtgtga ctgaagcct                                           19

<210> SEQ ID NO 164
<211> LENGTH: 15
<212> TYPE: DNA
<213> ORGANISM: Artificial Sequence
<220> FEATURE:
<223> OTHER INFORMATION: hnSR100-7178-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA
```

-continued

```
<220> FEATURE:
<221> NAME/KEY: modified_base
<222> LOCATION: (13)..(13)
<223> OTHER INFORMATION: 5mC

<400> SEQUENCE: 164
taatttgtgt gactg                                                    15

<210> SEQ ID NO 165
<211> LENGTH: 17
<212> TYPE: DNA
<213> ORGANISM: Artificial Sequence
<220> FEATURE:
<223> OTHER INFORMATION: hnSR100-7176-AmNA(17)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (15)..(16)
<223> OTHER INFORMATION: AmNA

<400> SEQUENCE: 165
taatttgtgt gactgaa                                                  17

<210> SEQ ID NO 166
<211> LENGTH: 19
<212> TYPE: DNA
<213> ORGANISM: Artificial Sequence
<220> FEATURE:
<223> OTHER INFORMATION: hnSR100-7174-AmNA(19)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (17)..(18)
<223> OTHER INFORMATION: AmNA

<400> SEQUENCE: 166
taatttgtgt gactgaagc                                                19

<210> SEQ ID NO 167
<211> LENGTH: 15
<212> TYPE: DNA
<213> ORGANISM: Artificial Sequence
<220> FEATURE:
<223> OTHER INFORMATION: NEG#26AmNA
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA

<400> SEQUENCE: 167
tgaacaaaat aatac                                                    15

<210> SEQ ID NO 168
<211> LENGTH: 15
<212> TYPE: DNA
<213> ORGANISM: Artificial Sequence
<220> FEATURE:
<223> OTHER INFORMATION: hnSR100-680-LNA(15)
<220> FEATURE:
<221> NAME/KEY: modified_base
<222> LOCATION: (1)..(3)
```

<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 168
tggtgtcaag tcttt                                                    15

<210> SEQ ID NO 169
<211> LENGTH: 15
<212> TYPE: DNA
<213> ORGANISM: Artificial Sequence
<220> FEATURE:
<223> OTHER INFORMATION: hnSR100-1064-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (2)..(2)
<223> OTHER INFORMATION: 5mC
<220> FEATURE:
<221> NAME/KEY: modified_base
<222> LOCATION: (13)..(14)
<223> OTHER INFORMATION: 2',4'-BNA/LNA

<400> SEQUENCE: 169
gcagagggtc ttgga                                                    15

<210> SEQ ID NO 170
<211> LENGTH: 15
<212> TYPE: DNA
<213> ORGANISM: Artificial Sequence
<220> FEATURE:
<223> OTHER INFORMATION: hnSR100-3841-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 170
ggaaagattg ggtag                                                    15

<210> SEQ ID NO 171
<211> LENGTH: 15
<212> TYPE: DNA
<213> ORGANISM: Artificial Sequence
<220> FEATURE:
<223> OTHER INFORMATION: hnSR100-3854-LNA(15)
<220> FEATURE:
<221> NAME/KEY: modified_base
<222> LOCATION: (1)..(3)
<223> OTHER INFORMATION: 2',4'-BNA/LNA
<220> FEATURE:
<221> NAME/KEY: modified_base
<222> LOCATION: (13)..(14)
<223> OTHER INFORMATION: 2',4'-BNA/LNA

<400> SEQUENCE: 171
ggttgatagg atggg                                                    15

<210> SEQ ID NO 172
<211> LENGTH: 15
<212> TYPE: DNA
<213> ORGANISM: Artificial Sequence

```
<220> FEATURE:
<223> OTHER INFORMATION: hnSR100-604-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (1)..(1)
<223> OTHER INFORMATION: 5mC
<220> FEATURE:
<221> NAME/KEY: modified_base
<222> LOCATION: (13)..(14)
<223> OTHER INFORMATION: AmNA
<220> FEATURE:
<221> NAME/KEY: modified_base
<222> LOCATION: (13)..(13)
<223> OTHER INFORMATION: 5mC
<220> FEATURE:
<221> NAME/KEY: modified_base
<222> LOCATION: (14)..(14)
<223> OTHER INFORMATION: 5mC

<400> SEQUENCE: 172
caactgttgg tgccc                                                    15

<210> SEQ ID NO 173
<211> LENGTH: 15
<212> TYPE: DNA
<213> ORGANISM: Artificial Sequence
<220> FEATURE:
<223> OTHER INFORMATION: hnSR100-1566-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA
<220> FEATURE:
<221> NAME/KEY: modified_base
<222> LOCATION: (13)..(14)
<223> OTHER INFORMATION: 5mC

<400> SEQUENCE: 173
tgctggcata ggagg                                                    15

<210> SEQ ID NO 174
<211> LENGTH: 15
<212> TYPE: DNA
<213> ORGANISM: Artificial Sequence
<220> FEATURE:
<223> OTHER INFORMATION: hnSR100-1582-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA
<220> FEATURE:
<221> NAME/KEY: modified_base
<222> LOCATION: (13)..(13)
<223> OTHER INFORMATION: 5mC

<400> SEQUENCE: 174
tgactggagg atcgg                                                    15

<210> SEQ ID NO 175
<211> LENGTH: 15
<212> TYPE: DNA
```

```
<213> ORGANISM: Artificial Sequence
<220> FEATURE:
<223> OTHER INFORMATION: hnSR100-1584-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA

<400> SEQUENCE: 175
agtgactgga ggatc                                                        15

<210> SEQ ID NO 176
<211> LENGTH: 15
<212> TYPE: DNA
<213> ORGANISM: Artificial Sequence
<220> FEATURE:
<223> OTHER INFORMATION: hnSR100-1633-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (1)..(1)
<223> OTHER INFORMATION: 5mC
<220> FEATURE:
<221> NAME/KEY: modified_base
<222> LOCATION: (13)..(14)
<223> OTHER INFORMATION: AmNA

<400> SEQUENCE: 176
cggctttggg tgtac                                                        15

<210> SEQ ID NO 177
<211> LENGTH: 15
<212> TYPE: DNA
<213> ORGANISM: Artificial Sequence
<220> FEATURE:
<223> OTHER INFORMATION: hnSR100-1645-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA
<220> FEATURE:
<221> NAME/KEY: modified_base
<222> LOCATION: (13)..(13)
<223> OTHER INFORMATION: 5mC

<400> SEQUENCE: 177
gaagaggtgg atcgg                                                        15

<210> SEQ ID NO 178
<211> LENGTH: 15
<212> TYPE: DNA
<213> ORGANISM: Artificial Sequence
<220> FEATURE:
<223> OTHER INFORMATION: hnSR100-1689-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (2)..(2)
<223> OTHER INFORMATION: 5mC
```

<220> FEATURE:
<221> NAME/KEY: modified_base
<222> LOCATION: (13)..(14)
<223> OTHER INFORMATION: AmNA

<400> SEQUENCE: 178
acttggagga atagc                                                        15

<210> SEQ ID NO 179
<211> LENGTH: 15
<212> TYPE: DNA
<213> ORGANISM: Artificial Sequence
<220> FEATURE:
<223> OTHER INFORMATION: hnSR100-1690-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (3)..(3)
<223> OTHER INFORMATION: 5mC
<220> FEATURE:
<221> NAME/KEY: modified_base
<222> LOCATION: (13)..(14)
<223> OTHER INFORMATION: AmNA

<400> SEQUENCE: 179
gacttggagg aatag                                                        15

<210> SEQ ID NO 180
<211> LENGTH: 15
<212> TYPE: DNA
<213> ORGANISM: Artificial Sequence
<220> FEATURE:
<223> OTHER INFORMATION: hnSR100-1697-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (1)..(1)
<223> OTHER INFORMATION: 5mC
<220> FEATURE:
<221> NAME/KEY: modified_base
<222> LOCATION: (13)..(14)
<223> OTHER INFORMATION: AmNA

<400> SEQUENCE: 180
cttgccagac ttgga                                                        15

<210> SEQ ID NO 181
<211> LENGTH: 15
<212> TYPE: DNA
<213> ORGANISM: Artificial Sequence
<220> FEATURE:
<223> OTHER INFORMATION: hnSR100-1858-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA

<400> SEQUENCE: 181
tttctcatag gcgag                                                        15

<210> SEQ ID NO 182

-continued

```
<211> LENGTH: 15
<212> TYPE: DNA
<213> ORGANISM: Artificial Sequence
<220> FEATURE:
<223> OTHER INFORMATION: hnSR100-1863-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (3)..(3)
<223> OTHER INFORMATION: 5mC
<220> FEATURE:
<221> NAME/KEY: modified_base
<222> LOCATION: (13)..(14)
<223> OTHER INFORMATION: AmNA

<400> SEQUENCE: 182
ggcgctttct catag                                           15

<210> SEQ ID NO 183
<211> LENGTH: 15
<212> TYPE: DNA
<213> ORGANISM: Artificial Sequence
<220> FEATURE:
<223> OTHER INFORMATION: hnSR100-2906-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (1)..(1)
<223> OTHER INFORMATION: 5mC
<220> FEATURE:
<221> NAME/KEY: modified_base
<222> LOCATION: (13)..(14)
<223> OTHER INFORMATION: AmNA

<400> SEQUENCE: 183
catgctgagg tattg                                           15

<210> SEQ ID NO 184
<211> LENGTH: 15
<212> TYPE: DNA
<213> ORGANISM: Artificial Sequence
<220> FEATURE:
<223> OTHER INFORMATION: hnSR100-4810-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (2)..(2)
<223> OTHER INFORMATION: 5mC
<220> FEATURE:
<221> NAME/KEY: modified_base
<222> LOCATION: (13)..(14)
<223> OTHER INFORMATION: AmNA

<400> SEQUENCE: 184
acaagggatt tcgac                                           15

<210> SEQ ID NO 185
<211> LENGTH: 15
<212> TYPE: DNA
<213> ORGANISM: Artificial Sequence
<220> FEATURE:
<223> OTHER INFORMATION: hnSR100-5907-AmNA(15)
<220> FEATURE:
<221> NAME/KEY: modified_base
```

```
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA

<400> SEQUENCE: 185
tggtgatctg tcata                                                     15

<210> SEQ ID NO 186
<211> LENGTH: 15
<212> TYPE: DNA
<213> ORGANISM: Artificial Sequence
<220> FEATURE:
<223> OTHER INFORMATION: hnSR100-5908-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (1)..(1)
<223> OTHER INFORMATION: 5mC
<220> FEATURE:
<221> NAME/KEY: modified_base
<222> LOCATION: (13)..(14)
<223> OTHER INFORMATION: AmNA
<220> FEATURE:
<221> NAME/KEY: modified_base
<222> LOCATION: (13)..(13)
<223> OTHER INFORMATION: 5mC

<400> SEQUENCE: 186
ctggtgatct gtcat                                                     15

<210> SEQ ID NO 187
<211> LENGTH: 15
<212> TYPE: DNA
<213> ORGANISM: Artificial Sequence
<220> FEATURE:
<223> OTHER INFORMATION: hnSR100-5950-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA

<400> SEQUENCE: 187
ggatgttggt ttttg                                                     15

<210> SEQ ID NO 188
<211> LENGTH: 15
<212> TYPE: DNA
<213> ORGANISM: Artificial Sequence
<220> FEATURE:
<223> OTHER INFORMATION: hnSR100-6015-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (3)..(3)
<223> OTHER INFORMATION: 5mC
<220> FEATURE:
<221> NAME/KEY: modified_base
<222> LOCATION: (13)..(14)
<223> OTHER INFORMATION: AmNA
```

<400> SEQUENCE: 188
agcgggaagg tcaaa                                                        15

<210> SEQ ID NO 189
<211> LENGTH: 15
<212> TYPE: DNA
<213> ORGANISM: Artificial Sequence
<220> FEATURE:
<223> OTHER INFORMATION: hnSR100-6239-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (2)..(2)
<223> OTHER INFORMATION: 5mC
<220> FEATURE:
<221> NAME/KEY: modified_base
<222> LOCATION: (13)..(14)
<223> OTHER INFORMATION: AmNA
<220> FEATURE:
<221> NAME/KEY: modified_base
<222> LOCATION: (14)..(14)
<223> OTHER INFORMATION: 5mC

<400> SEQUENCE: 189 tcgttttta c tttca                                                       15

<210> SEQ ID NO 190
<211> LENGTH: 15
<212> TYPE: DNA
<213> ORGANISM: Artificial Sequence
<220> FEATURE:
<223> OTHER INFORMATION: hnSR100-6240-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (3)..(3)
<223> OTHER INFORMATION: 5mC
<220> FEATURE:
<221> NAME/KEY: modified_base
<222> LOCATION: (13)..(14)
<223> OTHER INFORMATION: AmNA

<400> SEQUENCE: 190
ttcgttttta ctttc                                                        15

<210> SEQ ID NO 191
<211> LENGTH: 15
<212> TYPE: DNA
<213> ORGANISM: Artificial Sequence
<220> FEATURE:
<223> OTHER INFORMATION: hnSR100-6302-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA

<400> SEQUENCE: 191 aataggggc tttga                                                         15

<210> SEQ ID NO 192
<211> LENGTH: 15

```
-continued

<212> TYPE: DNA
<213> ORGANISM: Artificial Sequence
<220> FEATURE:
<223> OTHER INFORMATION: hnSR100-6448-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA
<220> FEATURE:
<221> NAME/KEY: modified_base
<222> LOCATION: (14)..(14)
<223> OTHER INFORMATION: 5mC

<400> SEQUENCE: 192
aaatgaagtg atgcg                                                    15

<210> SEQ ID NO 193
<211> LENGTH: 15
<212> TYPE: DNA
<213> ORGANISM: Artificial Sequence
<220> FEATURE:
<223> OTHER INFORMATION: hnSR100-6755-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (1)..(1)
<223> OTHER INFORMATION: 5mC
<220> FEATURE:
<221> NAME/KEY: modified_base
<222> LOCATION: (13)..(14)
<223> OTHER INFORMATION: AmNA

<400> SEQUENCE: 193
cataagtttc tcagc                                                    15

<210> SEQ ID NO 194
<211> LENGTH: 15
<212> TYPE: DNA
<213> ORGANISM: Artificial Sequence
<220> FEATURE:
<223> OTHER INFORMATION: hnSR100-6870-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (2)..(2)
<223> OTHER INFORMATION: 5mC
<220> FEATURE:
<221> NAME/KEY: modified_base
<222> LOCATION: (13)..(14)
<223> OTHER INFORMATION: AmNA

<400> SEQUENCE: 194
acagcaacca cagat                                                    15

<210> SEQ ID NO 195
<211> LENGTH: 15
<212> TYPE: DNA
<213> ORGANISM: Artificial Sequence
<220> FEATURE:
<223> OTHER INFORMATION: hnSR100-7057-AmNA(15)
<220> FEATURE:
<221> NAME/KEY: modified_base
<222> LOCATION: (1)..(3)
```

<223> OTHER INFORMATION: AmNA
<220> FEATURE:
<221> NAME/KEY: modified_base
<222> LOCATION: (1)..(1)
<223> OTHER INFORMATION: 5mC
<220> FEATURE:
<221> NAME/KEY: modified_base
<222> LOCATION: (2)..(2)
<223> OTHER INFORMATION: 5mC
<220> FEATURE:
<221> NAME/KEY: modified_base
<222> LOCATION: (13)..(14)
<223> OTHER INFORMATION: AmNA

<400> SEQUENCE: 195
ccaattctca atagc                                              15

<210> SEQ ID NO 196
<211> LENGTH: 15
<212> TYPE: DNA
<213> ORGANISM: Artificial Sequence
<220> FEATURE:
<223> OTHER INFORMATION: hnSR100-7060-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA

<400> SEQUENCE: 196
ggaccaattc tcaat                                              15

<210> SEQ ID NO 197
<211> LENGTH: 15
<212> TYPE: DNA
<213> ORGANISM: Artificial Sequence
<220> FEATURE:
<223> OTHER INFORMATION: hnSR100-7130-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA
<220> FEATURE:
<221> NAME/KEY: modified_base
<222> LOCATION: (13)..(13)
<223> OTHER INFORMATION: 5mC

<400> SEQUENCE: 197
gtgattctag cactc                                              15

<210> SEQ ID NO 198
<211> LENGTH: 15
<212> TYPE: DNA
<213> ORGANISM: Artificial Sequence
<220> FEATURE:
<223> OTHER INFORMATION: hnSR100-7131-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA
<220> FEATURE:
<221> NAME/KEY: modified_base
<222> LOCATION: (14)..(14)
<223> OTHER INFORMATION: 5mC

<400> SEQUENCE: 198
ggtgattcta gcact                                              15

<210> SEQ ID NO 199
<211> LENGTH: 15
<212> TYPE: DNA
<213> ORGANISM: Artificial Sequence
<220> FEATURE:
<223> OTHER INFORMATION: hnSR100-7133-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA
<220> FEATURE:
<221> NAME/KEY: modified_base
<222> LOCATION: (14)..(14)
<223> OTHER INFORMATION: 5mC

<400> SEQUENCE: 199
ttggtgattc tagca                                              15

<210> SEQ ID NO 200
<211> LENGTH: 15
<212> TYPE: DNA
<213> ORGANISM: Artificial Sequence
<220> FEATURE:
<223> OTHER INFORMATION: hnSR100-7134-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (1)..(1)
<223> OTHER INFORMATION: 5mC
<220> FEATURE:
<221> NAME/KEY: modified_base
<222> LOCATION: (13)..(14)
<223> OTHER INFORMATION: AmNA

<400> SEQUENCE: 200
cttggtgatt ctagc                                              15

<210> SEQ ID NO 201
<211> LENGTH: 15
<212> TYPE: DNA
<213> ORGANISM: Artificial Sequence
<220> FEATURE:
<223> OTHER INFORMATION: hnSR100-7135-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (2)..(2)
<223> OTHER INFORMATION: 5mC
<220> FEATURE:
<221> NAME/KEY: modified_base
<222> LOCATION: (13)..(14)
<223> OTHER INFORMATION: AmNA

<400> SEQUENCE: 201
gcttggtgat tctag                                              15

```
<210> SEQ ID NO 202
<211> LENGTH: 15
<212> TYPE: DNA
<213> ORGANISM: Artificial Sequence
<220> FEATURE:
<223> OTHER INFORMATION: hnSR100-7136-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (3)..(3)
<223> OTHER INFORMATION: 5mC
<220> FEATURE:
<221> NAME/KEY: modified_base
<222> LOCATION: (13)..(14)
<223> OTHER INFORMATION: AmNA
<220> FEATURE:
<221> NAME/KEY: modified_base
<222> LOCATION: (13)..(13)
<223> OTHER INFORMATION: 5mC

<400> SEQUENCE: 202
tgcttggtga ttcta                                                  15

<210> SEQ ID NO 203
<211> LENGTH: 15
<212> TYPE: DNA
<213> ORGANISM: Artificial Sequence
<220> FEATURE:
<223> OTHER INFORMATION: hnSR100-7203-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (1)..(1)
<223> OTHER INFORMATION: 5mC
<220> FEATURE:
<221> NAME/KEY: modified_base
<222> LOCATION: (2)..(2)
<223> OTHER INFORMATION: 5mC
<220> FEATURE:
<221> NAME/KEY: modified_base
<222> LOCATION: (13)..(14)
<223> OTHER INFORMATION: AmNA

<400> SEQUENCE: 203
ccagtgtttt agttc                                                  15

<210> SEQ ID NO 204
<211> LENGTH: 15
<212> TYPE: DNA
<213> ORGANISM: Artificial Sequence
<220> FEATURE:
<223> OTHER INFORMATION: hnSR100-7365-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA

<400> SEQUENCE: 204
aagatgaggc atagc                                                  15

<210> SEQ ID NO 205
<211> LENGTH: 15
```

```
<212> TYPE: DNA
<213> ORGANISM: Artificial Sequence
<220> FEATURE:
<223> OTHER INFORMATION: hnSR100-7373-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (1)..(1)
<223> OTHER INFORMATION: 5mC
<220> FEATURE:
<221> NAME/KEY: modified_base
<222> LOCATION: (3)..(3)
<223> OTHER INFORMATION: 5mC
<220> FEATURE:
<221> NAME/KEY: modified_base
<222> LOCATION: (13)..(14)
<223> OTHER INFORMATION: AmNA

<400> SEQUENCE: 205
ctcgttagaa gatga                                              15

<210> SEQ ID NO 206
<211> LENGTH: 15
<212> TYPE: DNA
<213> ORGANISM: Artificial Sequence
<220> FEATURE:
<223> OTHER INFORMATION: hnSR100-7688-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA

<400> SEQUENCE: 206
tatatgactg tggga                                              15

<210> SEQ ID NO 207
<211> LENGTH: 15
<212> TYPE: DNA
<213> ORGANISM: Artificial Sequence
<220> FEATURE:
<223> OTHER INFORMATION: hnSR100-7733-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (1)..(1)
<223> OTHER INFORMATION: 5mC
<220> FEATURE:
<221> NAME/KEY: modified_base
<222> LOCATION: (13)..(14)
<223> OTHER INFORMATION: AmNA

<400> SEQUENCE: 207
caggatacaa gagtt                                              15

<210> SEQ ID NO 208
<211> LENGTH: 15
<212> TYPE: DNA
<213> ORGANISM: Artificial Sequence
<220> FEATURE:
<223> OTHER INFORMATION: hnSR100-7734-AmNA(15)
<220> FEATURE:
<221> NAME/KEY: modified_base
<222> LOCATION: (1)..(3)
```

```
<223> OTHER INFORMATION: AmNA
<220> FEATURE:
<221> NAME/KEY: modified_base
<222> LOCATION: (1)..(1)
<223> OTHER INFORMATION: 5mC
<220> FEATURE:
<221> NAME/KEY: modified_base
<222> LOCATION: (2)..(2)
<223> OTHER INFORMATION: 5mC
<220> FEATURE:
<221> NAME/KEY: modified_base
<222> LOCATION: (13)..(14)
<223> OTHER INFORMATION: AmNA

<400> SEQUENCE: 208
ccaggataca agagt                                                   15

<210> SEQ ID NO 209
<211> LENGTH: 15
<212> TYPE: DNA
<213> ORGANISM: Artificial Sequence
<220> FEATURE:
<223> OTHER INFORMATION: hnSR100-7769-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA

<400> SEQUENCE: 209
gagagaagtt caaac                                                   15

<210> SEQ ID NO 210
<211> LENGTH: 15
<212> TYPE: DNA
<213> ORGANISM: Artificial Sequence
<220> FEATURE:
<223> OTHER INFORMATION: hnSR100-7792-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA
<220> FEATURE:
<221> NAME/KEY: modified_base
<222> LOCATION: (13)..(13)
<223> OTHER INFORMATION: 5mC

<400> SEQUENCE: 210
atgactttgg accac                                                   15

<210> SEQ ID NO 211
<211> LENGTH: 15
<212> TYPE: DNA
<213> ORGANISM: Artificial Sequence
<220> FEATURE:
<223> OTHER INFORMATION: hnSR100-7794-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA
<220> FEATURE:
<221> NAME/KEY: modified_base
```

```
<222> LOCATION: (14)..(14)
<223> OTHER INFORMATION: 5mC

<400> SEQUENCE: 211
tgatgacttt ggacc                                                    15

<210> SEQ ID NO 212
<211> LENGTH: 15
<212> TYPE: DNA
<213> ORGANISM: Artificial Sequence
<220> FEATURE:
<223> OTHER INFORMATION: hnSR100-7827-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (1)..(1)
<223> OTHER INFORMATION: 5mC
<220> FEATURE:
<221> NAME/KEY: modified_base
<222> LOCATION: (13)..(14)
<223> OTHER INFORMATION: AmNA

<400> SEQUENCE: 212
cagggcaagg taagc                                                    15

<210> SEQ ID NO 213
<211> LENGTH: 15
<212> TYPE: DNA
<213> ORGANISM: Artificial Sequence
<220> FEATURE:
<223> OTHER INFORMATION: hnSR100-7829-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (3)..(3)
<223> OTHER INFORMATION: 5mC
<220> FEATURE:
<221> NAME/KEY: modified_base
<222> LOCATION: (13)..(14)
<223> OTHER INFORMATION: AmNA

<400> SEQUENCE: 213
agcagggcaa ggtaa                                                    15

<210> SEQ ID NO 214
<211> LENGTH: 15
<212> TYPE: DNA
<213> ORGANISM: Artificial Sequence
<220> FEATURE:
<223> OTHER INFORMATION: hnSR100-7859-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA
<220> FEATURE:
<221> NAME/KEY: modified_base
<222> LOCATION: (13)..(13)
<223> OTHER INFORMATION: 5mC

<400> SEQUENCE: 214
tgggcatgtc aactc                                                    15
```

<210> SEQ ID NO 215
<211> LENGTH: 15
<212> TYPE: DNA
<213> ORGANISM: Artificial Sequence
<220> FEATURE:
<223> OTHER INFORMATION: hnSR100-7860-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA
<220> FEATURE:
<221> NAME/KEY: modified_base
<222> LOCATION: (14)..(14)
<223> OTHER INFORMATION: 5mC

<400> SEQUENCE: 215
ttgggcatgt caact                                                      15

<210> SEQ ID NO 216
<211> LENGTH: 15
<212> TYPE: DNA
<213> ORGANISM: Artificial Sequence
<220> FEATURE:
<223> OTHER INFORMATION: hnSR100-8001-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA

<400> SEQUENCE: 216
atgttggaca ttgag                                                      15

<210> SEQ ID NO 217
<211> LENGTH: 15
<212> TYPE: DNA
<213> ORGANISM: Artificial Sequence
<220> FEATURE:
<223> OTHER INFORMATION: hnSR100-8165-AmNA(15)
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (13)..(14)
<223> OTHER INFORMATION: AmNA

<400> SEQUENCE: 217
atggccttgg ggtgc                                                      15

<210> SEQ ID NO 218
<211> LENGTH: 15
<212> TYPE: DNA
<213> ORGANISM: Artificial Sequence
<220> FEATURE:
<223> OTHER INFORMATION: hnSR100-7174-AmNA, scpBNA(15)
<220> FEATURE:
<221> NAME/KEY: modified_base
<222> LOCATION: (1)..(2)
<223> OTHER INFORMATION: scpBNA
<220> FEATURE:
<221> NAME/KEY: modified_base
<222> LOCATION: (3)..(3)
<223> OTHER INFORMATION: AmNA

```
<220> FEATURE:
<221> NAME/KEY: modified_base
<222> LOCATION: (13)..(14)
<223> OTHER INFORMATION: AmNA
<220> FEATURE:
<221> NAME/KEY: modified_base
<222> LOCATION: (15)..(15)
<223> OTHER INFORMATION: scpBNA
<220> FEATURE:
<221> NAME/KEY: modified_base
<222> LOCATION: (15)..(15)
<223> OTHER INFORMATION: 5mC

<400> SEQUENCE: 218
ttgtgtgact gaagc                                                    15

<210> SEQ ID NO 219
<211> LENGTH: 15
<212> TYPE: DNA
<213> ORGANISM: Artificial Sequence
<220> FEATURE:
<223> OTHER INFORMATION: hnSR100-7174-AmNA, GuNA(15)
<220> FEATURE:
<221> NAME/KEY: modified_base
<222> LOCATION: (1)..(2)
<223> OTHER INFORMATION: GuNA
<220> FEATURE:
<221> NAME/KEY: modified_base
<222> LOCATION: (3)..(3)
<223> OTHER INFORMATION: AmNA
<220> FEATURE:
<221> NAME/KEY: modified_base
<222> LOCATION: (13)..(14)
<223> OTHER INFORMATION: AmNA

<400> SEQUENCE: 219
ttgtgtgact gaagc                                                    15
```

SMALL CELL LUNG CANCER THERAPEUTIC AGENT CONTAINING OLIGONUCLEOTIDE

TECHNICAL FIELD

The present invention relates to an oligonucleotide having nSR100 gene expression inhibiting activity, and a therapeutic agent for cancer (e.g., small cell lung cancer (SCLC)) containing such an oligonucleotide.

BACKGROUND ART

Lung cancer, which is a major cause of cancer-related death, is classified into two types, namely small cell lung cancer (SCLC) and non-small cell lung cancer (NSCLC). In general, SCLC is a high-grade cancer involving rapid growth and metastasis of cancer cells, and it is often difficult to surgically remove it. Furthermore, a cytocidal antitumor agent is effective at an initial stage of treatment of small cell lung cancer, but recurrence is frequent. In the case of recurrence, tolerance to existing antitumor agents is often a problem, and prognosis is unfavorable. On the other hand, molecular-targeted therapeutic agents for NSCLC have been developed and shown to have a certain therapeutic effect. However, NSCLC may change into SCLC in some patients, and thus is often treated inappropriately. It is recently reported that the number of lung cancer patients including many children is rapidly increasing with an increase in carcinogens such as PM2.5.

Unlike NSCLC, SCLC is a tumor derived from neuroendocrine cells, and many neural gene products are expressed in neuroendocrine cells. It is reported that a transcription suppressing factor REST (RE1-Silencing Transcription factor) is a master molecule for neural genes and also serves as a tumor suppressing factor. nSR100 (neural-specific SR-related protein of 100 kDa) (also referred to as "SRRM4 (Serine Arginine Repetitive Matrix 4)") is known to have a function of controlling splicing of REST. It is known that the abnormal expression of nSR100 (SRRM4) has an influence on the malignancy of SCLC (Non-Patent Document 1 and Patent Document 1). Accordingly, the nSR100 (SRRM4) gene is useful as a marker gene for SCLC (Patent Document 1).

In the current treatment of SCLC, PE therapy (cisplatin and etoposide are used together) and PI therapy (cisplatin and irinotecan are used together) are used. However, both therapies are problematic in that the incidence rate of side effects such as diarrhea is significantly high. In addition, irinotecan is limited in use because the use thereof is contraindicated for patients with interstitial pneumonia. Moreover, if SCLC recurs after treatment with chemotherapy, tolerance to chemotherapy is developed.

Accordingly, there is a demand for development of a novel SCLC therapeutic agent.

RELATED ART DOCUMENTS

Patent Document

Patent Document 1: WO2015/012175

Non-Patent Document

Non-Patent Document 1: Mol. Cancer Res., vol. 11, no. 10, 2013: 1258-1268

SUMMARY OF THE INVENTION

Problem to be Solved by the Invention

An object of the present invention is to provide a nucleic acid medicine that is effective for treatment of small cell lung cancer (SCLC).

Means for Solving the Problem

The present invention provides an oligonucleotide or a pharmacologically acceptable salt thereof, wherein the oligonucleotide comprises at least one nucleoside structure represented by Formula (I) below:

[Chemical Formula 1]

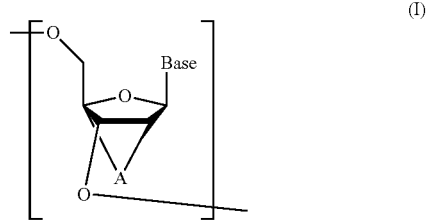

where
Base represents a purin-9-yl group that may have any one or more substituents selected from an α group, or a 2-oxo-1,2-dihydropyrimidin-1-yl group that may have any one or more substituents selected from the a group, the a group consisting of a hydroxy group, a hydroxy group protected by a protecting group for nucleic acid synthesis, linear alkyl groups having 1 to 6 carbon atoms, linear alkoxy groups having 1 to 6 carbon atoms, a mercapto group, a mercapto group protected by a protecting group for nucleic acid synthesis, linear alkylthio groups having 1 to 6 carbon atoms, an amino group, linear alkylamino groups having 1 to 6 carbon atoms, an amino group protected by a protecting group for nucleic acid synthesis, and halogen atoms, and
A is a divalent group represented by:

[Chemical Formula 2]

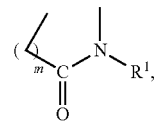

(a-1)

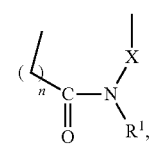

(a-2)

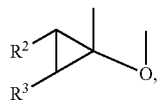

(b-1)

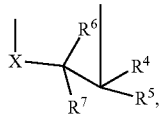

(c-1)

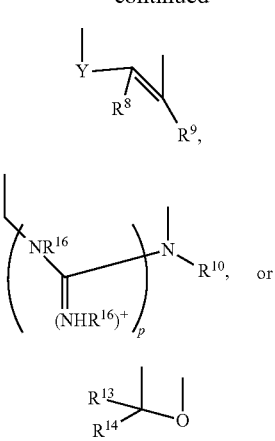

(c-2)

(d-1)

(e-1)

where R¹ represents a hydrogen atom, an alkyl group having 1 to 7 carbon atoms that may form a branch or a ring, an alkenyl group having 2 to 7 carbon atoms that may form a branch or a ring, an aryl group having 3 to 12 carbon atoms that may have any one or more substituents selected from the a group and that may have a hetero atom, an aralkyl group with an aryl moiety having 3 to 12 carbon atoms that may have any one or more substituents selected from the a group and that may include a hetero atom, or an amino group protecting group for nucleic acid synthesis;

R² and R³ are independently a hydrogen atom, an alkyl group having 1 to 7 carbon atoms that may have undergone substitution by an aryl group having 3 to 12 carbon atoms that may include a hetero atom and that may form a branch or a ring, or an aralkyl group with an aryl moiety having 3 to 12 carbon atoms that may include a hetero atom, or R² and R³ represent —(CH$_2$)$_q$— [where q is an integer from 2 to 5] together;

R⁴ and R⁵ are independently a group selected from the group consisting of a hydrogen atom, a hydroxy group, alkyl groups having 1 to 7 carbon atoms that optionally form a branch or a ring, alkoxy groups having 1 to 7 carbon atoms that optionally form a branch or a ring, an amino group, and an amino group protected by a protecting group for nucleic acid synthesis, or R⁴ and R⁵ form =C(R¹¹)R¹² [where R¹¹ and R¹² independently represent a hydrogen atom, a hydroxy group, a hydroxy group protected by a protecting group for nucleic acid synthesis, a mercapto group, a mercapto group protected by a protecting group for nucleic acid synthesis, an amino group, a linear or branched alkoxy group having 1 to 6 carbon atoms, a linear or branched alkylthio group having 1 to 6 carbon atoms, a cyanoalkoxy group having 1 to 6 carbon atoms, or a linear or branched alkylamino group having 1 to 6 carbon atoms] together;

R⁶ and R⁷ are independently a hydrogen atom, an alkyl group having 1 to 7 carbon atoms that may form a branch or a ring, an alkoxy group having 1 to 7 carbon atoms that may form a branch or a ring, or a linear or branched alkylthio group having 1 to 6 carbon atoms;

R⁸ represents a hydrogen atom, an alkyl group having 1 to 7 carbon atoms that may form a branch or a ring, or a linear or branched alkylthio group having 1 to 6 carbon atoms;

R⁹ is a hydrogen atom, a hydroxy group, an alkyl group having 1 to 7 carbon atoms that may form a branch or a ring, an alkoxy group having 1 to 7 carbon atoms that may form a branch or a ring, an amino group, or an amino group protected by a protecting group for nucleic acid synthesis;

R¹⁰ is a hydrogen atom, an alkyl group having 1 to 7 carbon atoms that may form a branch or a ring, an amino group protecting group, or

[Chemical Formula 3]

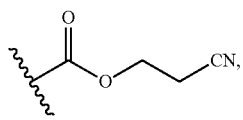

or

—(C=(NHR¹⁷)+)—NR¹⁸R¹⁹ [where R¹⁷, R¹⁸, and R¹⁹ are independently a hydrogen atom, an alkyl group having 1 to 7 carbon atoms that may form a branch or a ring, an amino group protecting group, or

[Chemical Formula 4]

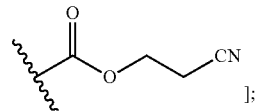

];

R¹³ and R¹⁴ are independently a group selected from the group consisting of a hydrogen atom, a hydroxy group, alkyl groups having 1 to 7 carbon atoms that optionally form a branch or a ring, alkoxy groups having 1 to 7 carbon atoms that optionally form a branch or a ring, an amino group, and an amino group protected by a protecting group for nucleic acid synthesis;

m is an integer from 0 to 2;

n is an integer of 0 to 1;

when R¹⁰ is a hydrogen atom, an alkyl group having 1 to 7 carbon atoms that may form a branch or a ring, an amino group protecting group, or

[Chemical Formula 5]

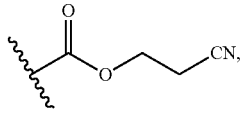

p is 1, and R¹⁵ and R¹⁶ are independently a hydrogen atom, an alkyl group having 1 to 7 carbon atoms that may form a branch or a ring, an amino group protecting group, or

[Chemical Formula 6]

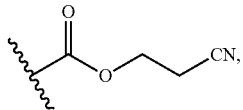

or when R¹⁰ is —(C=(NHR¹⁷)+)—NR¹⁸R¹⁹, p is 0;

X is an oxygen atom, a sulfur atom, or an amino group; and

Y is an oxygen atom or a sulfur atom,
the oligonucleotide can bind to a human nSR100 gene and has human nSR100 expression inhibiting activity,
the oligonucleotide has a length of 12 to 20 mer, and
the oligonucleotide includes a sequence that is complementary to a target region having a 12- to 20-mer continuous sequence in a base sequence from position 600 to position 620, from position 640 to position 700, from position 710 to position 800, from position 1060 to position 1080, from position 1560 to position 1600, from position 1630 to position 1660, from position 1685 to position 1720, from position 1850 to position 1900, from position 2900 to position 2925, from position 3835 to position 3875, from position 4800 to position 4830, from position 5900 to position 5970, from position 6010 to position 6035, from position 6230 to position 6270, from position 6300 to position 6320, from position 6440 to position 6470, from position 6750 to position 6772, from position 6865 to position 6890, from position 7045 to position 7080, from position 7130 to position 7155, from position 7160 to position 7220, from position 7360 to position 7390, from position 7680 to position 7850, from position 7950 to position 7980, from position 7995 to position 8020 or from position 8160 to position 8180 in SEQ ID No. 1.

In one embodiment, the 5' end of the target region corresponds to position 7168, position 7170, position 7172, or position 7174 in SEQ ID No. 1, and the oligonucleotide has a length of 15 to 19 mer.

In one embodiment, the base sequence of the oligonucleotide includes any of base sequences of SEQ ID Nos. 2 to 71.

In one embodiment, the oligonucleotide is a gapmer comprising a 6- to 15-mer gap region, a 3- to 5-mer 5' wing, and a 3- to 5-mer 3' wing, the gap region is located between the 5' wing and the 3' wing, and the 5' wing and the 3' wing comprises at least one nucleoside structure represented by Formula (I).

In one embodiment, the nucleoside structure represented by Formula (I) is

[Chemical Formula 7]

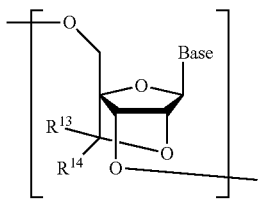

where both $R^{13}$ and $R^{14}$ are hydrogen atoms;

[Chemical Formula 8]

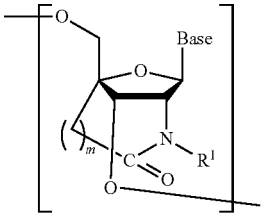

where m is 0, and $R^1$ is a hydrogen atom, a methyl group, an ethyl group, an n-propyl group, an isopropyl group, a phenyl group, or a benzyl group;

[Chemical Formula 9]

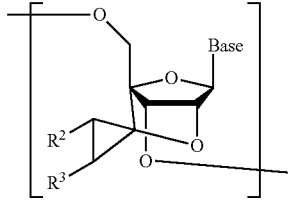

where $R^2$ and $R^3$ are independently a hydrogen atom, an alkyl group having 1 to 7 carbon atoms that may have undergone substitution by an aryl group having 3 to 12 carbon atoms that may include a hetero atom and that may form a branch or a ring, or an aralkyl group with an aryl moiety having 3 to 12 carbon atoms that may include a hetero atom, or $R^2$ and $R^3$ represent —$(CH_2)O_q$— (where q is an integer from 2 to 5) together; or

[Chemical Formula 10]

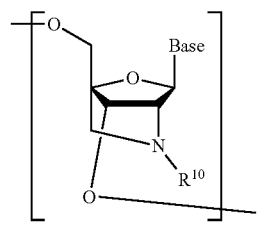

where $R^{10}$ is —(C=(NHR$^{17}$)+)—NR$^{18}$R$^{19}$, where $R^{17}$ and $R^{18}$ are independently a hydrogen atom or an alkyl group having 1 to 7 carbon atoms that may form a branch or a ring, and $R^{19}$ is a hydrogen atom.

In one embodiment, the oligonucleotide is
nSR100L #1/hnSR100-712-LNA(15) (SEQ ID No. 76),
hnSR100L #2/hnSR100-717-LNA(15) (SEQ ID No. 77),
hnSR100L #3/hnSR100-721-LNA(15) (SEQ ID No. 78),
hnSR100L #4/hnSR100-780-LNA(15) (SEQ ID No. 79),
hnSR100L #5/hnSR100-783-LNA(15) (SEQ ID No. 80),
hnSR100L #6/hnSR100-786-LNA(15) (SEQ ID No. 81),
hnSR100L #21/hnSR100-7174-LNA(15) (SEQ ID No. 96),
hnSR100L #22/hnSR100-7177-LNA(15) (SEQ ID No. 97),
hnSR100-7170-LNA(19) (SEQ ID No. 124),
hnSR100-7172-LNA(15) (SEQ ID No. 125),
hnSR100-7170-LNA(17) (SEQ ID No. 126),
hnSR100-7168-LNA(19) (SEQ ID No. 127),
hnSR100-7170-LNA(15) (SEQ ID No. 128),
hnSR100-7168-LNA(17) (SEQ ID No. 129),
hnSR100-7166-LNA(19) (SEQ ID No. 130),
hnSR100-7176-LNA(15) (SEQ ID No. 131),
hnSR100-7174-LNA(17) (SEQ ID No. 132),
hnSR100-7172-LNA(19) (SEQ ID No. 133),
hnSR100-7178-LNA(15) (SEQ ID No. 134),
hnSR100-7174-AmNA(15) (SEQ ID No. 152),
hnSR100-7172-AmNA(17) (SEQ ID No. 153),
hnSR100-7170-AmNA(19) (SEQ ID No. 154),
hnSR100-7172-AmNA(15) (SEQ ID No. 155), hnSR100-7170-AmNA(17) (SEQ ID No. 156),
hnSR100-7168-AmNA(19) (SEQ ID No. 157),
hnSR100-7170-AmNA(15) (SEQ ID No. 158),
hnSR100-7168-AmNA(17) (SEQ ID No. 159),
hnSR100-7174-AmNA(17) (SEQ ID No. 162),
hnSR100-7172-AmNA(19) (SEQ ID No. 163),
hnSR100-680-LNA(15) (SEQ ID No. 168),
hnSR100-1064-LNA(15) (SEQ ID No. 169),
hnSR100-3841-LNA(15) (SEQ ID No. 170),
hnSR100-3854-LNA(15) (SEQ ID No. 171),
hnSR100-604-AmNA(15) (SEQ ID No. 172),
hnSR100-1566-AmNA(15) (SEQ ID No. 173),
hnSR100-1582-AmNA(15) (SEQ ID No. 174),
hnSR100-1584-AmNA(15) (SEQ ID No. 175),
hnSR100-1633-AmNA(15) (SEQ ID No. 176),
hnSR100-1645-AmNA(15) (SEQ ID No. 177),
hnSR100-1689-AmNA(15) (SEQ ID No. 178),
hnSR100-1690-AmNA(15) (SEQ ID No. 179),
hnSR100-1697-AmNA(15) (SEQ ID No. 180),
hnSR100-1858-AmNA(15) (SEQ ID No. 181),
hnSR100-1863-AmNA(15) (SEQ ID No. 182),
hnSR100-2906-AmNA(15) (SEQ ID No. 183),
hnSR100-4810-AmNA(15) (SEQ ID No. 184),
hnSR100-5907-AmNA(15) (SEQ ID No. 185),
hnSR100-5908-AmNA(15) (SEQ ID No. 186),
hnSR100-5950-AmNA(15) (SEQ ID No. 187),
hnSR100-6015-AmNA(15) (SEQ ID No. 188),
hnSR100-6239-AmNA(15) (SEQ ID No. 189),
hnSR100-6240-AmNA(15) (SEQ ID No. 190),
hnSR100-6302-AmNA(15) (SEQ ID No. 191),
hnSR100-6448-AmNA(15) (SEQ ID No. 192),
hnSR100-6755-AmNA(15) (SEQ ID No. 193),
hnSR100-6870-AmNA(15) (SEQ ID No. 194),
hnSR100-7057-AmNA(15) (SEQ ID No. 195),
hnSR100-7060-AmNA(15) (SEQ ID No. 196),
hnSR100-7130-AmNA(15) (SEQ ID No. 197),
hnSR100-7131-AmNA(15) (SEQ ID No. 198),
hnSR100-7133-AmNA(15) (SEQ ID No. 199),
hnSR100-7134-AmNA(15) (SEQ ID No. 200),
hnSR100-7135-AmNA(15) (SEQ ID No. 201),
hnSR100-7136-AmNA(15) (SEQ ID No. 202),
hnSR100-7203-AmNA(15) (SEQ ID No. 203),
hnSR100-7365-AmNA(15) (SEQ ID No. 204),
hnSR100-7373-AmNA(15) (SEQ ID No. 205),
hnSR100-7688-AmNA(15) (SEQ ID No. 206),
hnSR100-7733-AmNA(15) (SEQ ID No. 207),
hnSR100-7734-AmNA(15) (SEQ ID No. 208),
hnSR100-7769-AmNA(15) (SEQ ID No. 209),
hnSR100-7792-AmNA(15) (SEQ ID No. 210)
hnSR100-7794-AmNA(15) (SEQ ID No. 211),
hnSR100-7827-AmNA(15) (SEQ ID No. 212),
hnSR100-7829-AmNA(15) (SEQ ID No. 213),
hnSR100-7859-AmNA(15) (SEQ ID No. 214),
hnSR100-7860-AmNA(15) (SEQ ID No. 215),
hnSR100-8001-AmNA(15) (SEQ ID No. 216),
hnSR100-8165-AmNA(15) (SEQ ID No. 217),
hnSR100-7174-AmNA, scpBNA(15) (SEQ ID No. 218), or
hnSR100-7174-AmNA, GuNA(15) (SEQ ID No. 219).

The present invention provides an nSR100 gene expression inhibitor comprising the oligonucleotide or the pharmacologically acceptable salt thereof as mentioned above.

The present invention provides a cancer therapeutic agent comprising the oligonucleotide or the pharmacologically acceptable salt thereof as mentioned above, or the nSR100 expression inhibitor as mentioned above.

In one embodiment, the cancer therapeutic agent is for use in treatment of at least one type of cancer selected from the group consisting of small cell lung cancer, prostate cancer, and breast cancer.

Effects of the Invention

According to the present invention, an oligonucleotide that is useful for inhibiting the nSR100 gene expression is provided. Furthermore, a therapeutic agent for cancer including small cell lung cancer can be provided. The present invention is also useful for developing a cancer therapeutic agent based on the suppression of the expression of the nSR100 gene.

DESCRIPTION OF EMBODIMENTS

Figure 1:
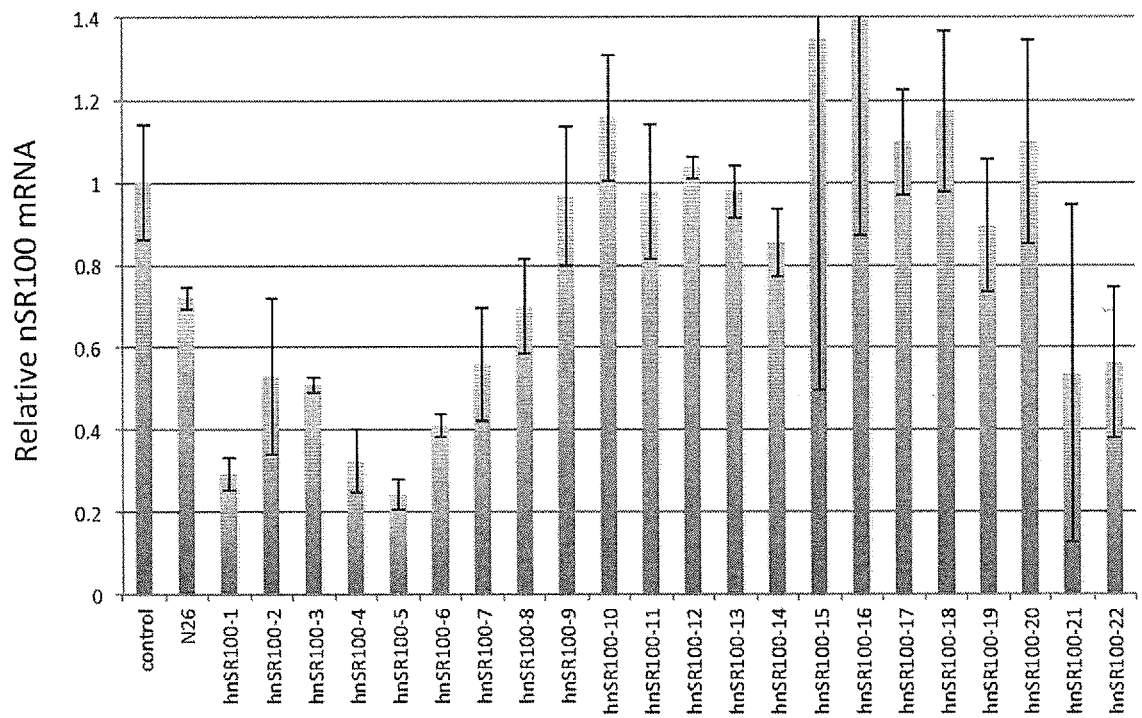
FIG. 1 shows graphs illustrating hnSR100 mRNA levels in human SCLC cells (A: human NCI-H82 cells; and B: human STC-1 cells) to which various antisense oligonucleotides have been added in vitro.
Figure 1:
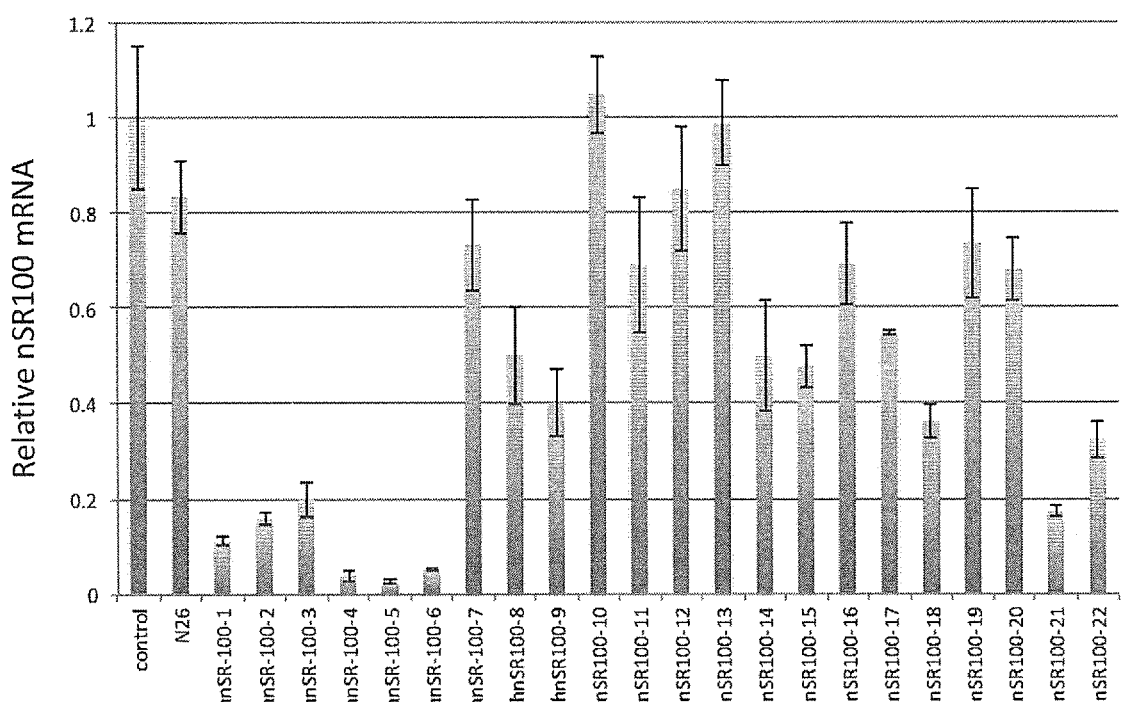

The following definitions shall apply throughout the specification.

The term "alkyl group having 1 to 3 carbon atoms" as used herein encompasses any alkyl groups having 1 to 3 carbon atoms. Specific examples thereof are a methyl group, an ethyl group, an n-propyl group, and an isopropyl group.

The term "linear alkyl group having 1 to 6 carbon atoms" encompasses any linear alkyl groups having 1 to 6 carbon atoms. Specific examples thereof are a methyl group, an ethyl group, an n-propyl group, an n-butyl group, an n-pentyl group, and an n-hexyl group.

The term "linear alkoxy group having 1 to 6 carbon atoms" encompasses alkoxy groups including any linear alkyl groups having 1 to 6 carbon atoms. Examples thereof include a methyloxy group, an ethyloxy group, and an n-propyloxy group. The term "linear or branched alkoxy group having 1 to 6 carbon atoms" encompasses alkoxy groups including any linear or branched alkyl groups having 1 to 6 carbon atoms. Examples thereof include a methyloxy group, an ethyloxy group, an n-propyloxy group, an isopropyloxy group, an n-butyloxy group, an isobutyloxy group, a tert-butyloxy group, an n-pentyloxy group, and an isopentyloxy group.

The term "linear alkylthio group having 1 to 6 carbon atoms" as used herein encompasses alkylthio groups including any linear alkyl group having 1 to 6 carbon atoms. Examples thereof include a methythio group, an ethylthio group, and an n-propylthio group. The term "linear or branched alkylthio group having 1 to 6 carbon atoms" as used herein encompasses alkylthio groups including any linear or branched alkyl groups having 1 to 6 carbon atoms. Examples thereof include a methythio group, an ethylthio group, an n-propylthio group, an isopropylthio group, an n-butylthio group, an isobutylthio group, a tert-butylthio group, an n-pentylthio group, and an isopentylthio group.

The term "cyanoalkoxy group having 1 to 6 carbon atoms" as used herein refers to a group obtained by substituting at least one hydrogen atom included in the above-mentioned linear alkoxy group having 1 to 6 carbon atoms with a cyano group.

The term "linear alkylamino group having 1 to 6 carbon atoms" as used herein encompasses groups obtained by substituting one or two hydrogen atoms included in an amino group with a linear alkyl group having 1 to 6 carbon atoms. Examples thereof include a methylamino group, a dimethylamino group, an ethylamino group, a methylethylamino group, and diethylamino group. The term "linear or branched alkylamino group having 1 to 6 carbon atoms" as used herein encompasses groups obtained by substituting one or two hydrogen atoms included in an amino group with a linear or branched alkyl group having 1 to 6 carbon atoms. Examples thereof include a methylamino group, a dimethylamino group, an ethylamino group, a methylethylamino group, a diethylamino group, an n-propylamino group, a di-n-propylamino group, an isopropylamino group, and diisopropylamino group.

The term "alkyl group having 1 to 7 carbon atoms that may form a branch or a ring" as used herein encompasses any linear alkyl groups having 1 to 7 carbon atoms, any branched alkyl groups having 3 to 7 carbon atoms, and any cyclic alkyl groups having 3 to 7 carbon atoms. Such groups may also be referred to merely as "lower alkyl groups". Examples of any linear alkyl groups having 1 to 7 carbon atoms include a methyl group, an ethyl group, an n-propyl group, an n-butyl group, an n-pentyl group, an n-hexyl group, and an n-heptyl group, examples of any branched alkyl groups having 3 to 7 carbon atoms include an isopropyl group, an isobutyl group, a tert-butyl group, and an isopentyl group, and examples of any cyclic alkyl groups having 3 to 7 carbon atoms include a cyclobutyl group, a cyclopentyl group, and a cyclohexyl group.

The term "alkenyl group having 2 to 7 carbon atoms that may form a branch or a ring" as used herein encompasses any linear alkenyl groups having 2 to 7 carbon atoms, any branched alkenyl groups having 3 to 7 carbon atoms, and any cyclic alkenyl groups having 3 to 7 carbon atoms. Such groups may also be referred to merely as "lower alkenyl groups". Examples of any linear alkenyl groups having 2 to 7 carbon atoms include an ethenyl group, a 1-propenyl group, a 2-propenyl group, a 1-butenyl group, a 2-butenyl group, a 1-pentenyl group, a 2-pentenyl group, a 3-pentenyl group, a 4-pentenyl group, and 1-hexenyl group, examples of any branched alkenyl groups having 3 to 7 carbon atoms include an isopropenyl group, a 1-methyl-1-propenyl group, a 1-methyl-2-propenyl group, a 2-methyl-1-propenyl group, a 2-methyl-2-propenyl group, and a 1-methyl-2-butenyl group, and examples of any cyclic alkenyl groups having 3 to 7 carbon atoms include a cyclobutenyl group, a cyclopentenyl group, and a cyclohexenyl group.

The term "alkoxy group having 1 to 7 carbon atoms that may form a branch or a ring" as used herein encompasses any linear alkoxy groups having 1 to 7 carbon atoms, any branched alkoxy groups having 3 to 7 carbon atoms, and any cyclic alkoxy groups having 3 to 7 carbon atoms. Such groups may also be referred to as "lower alkoxy groups". Examples of any linear alkoxy groups having 1 to 7 carbon atoms include a methoxy group, an ethoxy group, an n-propoxy group, an n-butyloxy, an n-pentyloxy group, an n-hexyloxy group, and an n-heptyloxy group, examples of any branched alkoxy groups having 3 to 7 carbon atoms include an isopropoxy group, an isobutyloxy group, a tert-butyloxy group, and an isopentyloxy group, and examples of any cyclic alkoxy groups having 3 to 7 carbon atoms include a cyclobutyloxy group, a cyclopentyloxy group, and a cyclohexyloxy group.

The term "aryl group having 3 to 12 carbon atoms that may include a hetero atom" as used herein encompasses any aryl groups having 6 to 12 carbon atoms that are only constituted by a hydrocarbon, and any heteroaryl groups having 3 to 12 carbon atoms obtained by substituting at least one carbon atom included in the ring structure of the above-mentioned aryl groups with a hetero atom (e.g., a nitrogen atom, an oxygen atom, a sulfur atom, and a combination thereof). Examples of the aryl groups having 6 to 12 carbon atoms include a phenyl group, a naphthyl group, an indenyl group, and an azulenyl group, and examples of any heteroaryl groups having 3 to 12 carbon atoms include a pyridyl group, a pyrrolyl group, a quinolyl group, an indolyl group, an imidazolyl group, a furyl group, and a thienyl group.

Examples of the term "aralkyl group including an aryl moiety having 3 to 12 carbon atoms that may include a hetero atom" as used herein include a benzyl group, a phenethyl group, a naphthylmethyl group, a 3-phenylpropyl group, a 2-phenylpropyl group, a 4-phenylbutyl group, a 2-phenylbutyl group, a pyridylmethyl group, an indolylmethyl group, a furylmethyl group, a thienylmethyl group, a pyrrolylmethyl group, a 2-pyridylethyl group, a 1-pyridylethyl group, and a 3-thienylpropyl group.

Examples of the term "acyl group" as used herein include aliphatic acyl groups and aromatic acyl groups. Specifically, examples of the aliphatic acyl groups include alkylcarbonyl groups such as a formyl group, an acetyl group, a propionyl group, a butyryl group, an isobutyryl group, a pentanoyl group, a pivaloyl group, a valeryl group, an isovaleryl group, an octanoyl group, a nonanoyl group, a decanoyl group, a 3-methylnonanoyl group, a 8-methylnonanoyl group, a 3-ethyloctanoyl group, a 3,7-dimethyloctanoyl group, an undecanoyl group, a dodecanoyl group, a tridecanoyl group, a tetradecanoyl group, a pentadecanoyl group, a hexadecanoyl group, a 1-methylpentadecanoyl group, a 14-methylpentadecanoyl group, a 13,13-dimethyltetradecanoyl group, a heptadecanoyl group, a 15-methylhexadecanoyl group, an octadecanoyl group, a 1-methylheptadecanoyl group, a nonadecanoyl group, an eicosanoyl group, and a heneicosanoyl group; carboxylated alkylcarbonyl groups such as a succinoyl group, a glutaroyl group, and an adipoyl group; halogeno lower-alkyl-carbonyl groups such as a chloroacetyl group, a dichloroacetyl group, a trichloroacetyl group, and a trifluoroacetyl group; lower-alkoxy-lower-alkyl-carbonyl groups such as a methoxyacetyl group; and unsaturated alkylcarbonyl groups such as an (E)-2-methyl-2-butenoyl group. Examples of the aromatic acyl groups include arylcarbonyl groups such as a benzoyl group, an α-naphthoyl group, and a 8-naphthoyl group; halogeno arylcarbonyl groups such as a 2-bromobenzoyl group and a 4-chlorobenzoyl group; low-alkylated arylcarbonyl groups such as a 2,4,6-trimethylbenzoyl group and a 4-toluoyl group; low-alkoxylated arylcarbonyl groups such as a 4-anisoyl group; carboxylated arylcarbonyl groups such as a 2-carboxybenzoyl group, a 3-carboxybenzoyl group, and a 4-carboxybenzoyl group; nitrated arylcarbonyl groups such as a 4-nitrobenzoyl group and a 2-nitrobenzoyl group; low-alkoxycarbonylated arylcarbonyl groups such as a 2-(methoxycarbonyl)benzoyl group; and arylated arylcarbonyl groups such as a 4-phenylbenzoyl group. A formyl group, an acetyl group, a propionyl group, a butyryl group, an isobutyryl group, a pentanoyl group, a pivaloyl group, and a benzoyl group are favorable.

Examples of the term "silyl group" as used herein include tri-lower-alkyl-silyl groups such as a trimethylsilyl group, a triethylsilyl group, an isopropyldimethylsilyl group, a t-butyldimethylsilyl group, a methyldiisopropylsilyl group, a methyldi-t-butylsilyl group, and a triisopropylsilyl group; and tri-lower-alkyl-silyl groups that have undergone substitution by one or two aryl groups such as a diphenylmethylsilyl group, a butyldiphenylbutylsilyl group, a diphenylisopropylsilyl group, and a phenyldiisopropylsilyl group. A trimethylsilyl group, a triethylsilyl group, a triisopropylsilyl group, a t-butyldimethylsilyl group, and a t-butyldiphenylsilyl group are favorable, and a trimethylsilyl group is more favorable.

Examples of the term "halogen atom" as used herein include a fluorine atom, a chlorine atom, a bromine atom, and an iodine atom. A fluorine atom or a chlorine atom is favorable.

Examples of the term "halide ion" as used herein include a fluoride ion, a chloride ion, a bromide ion, and an iodide ion. A fluoride ion or a chloride ion is favorable.

"Protecting groups" in the terms "amino group protecting group for nucleic acid synthesis", "hydroxy group protecting group for nucleic acid synthesis", "hydroxy group protected by a protecting group for nucleic acid synthesis", "phosphate group protected by a protecting group for nucleic acid synthesis", and "mercapto group protected by a protecting group for nucleic acid synthesis" as used herein are not particularly limited as long as they can stably protect an amino group, a hydroxy group, a phosphate group, or a mercapto group during nucleic acid synthesis. Specifically, the protecting groups are stable under an acidic or neutral condition and can be cleaved using chemical techniques such as hydrogenolysis, hydrolysis, electrolysis, and photolysis. Examples of such protecting groups include lower alkyl groups, lower alkenyl groups, acyl groups, tetrahydropyranyl or tetrahydrothiopyranyl groups, tetrahydrofuranyl or tetrahydrothiofuranyl groups, silyl groups, lower-alkoxy-methyl groups, low-alkoxilated lower-alkoxy-methyl groups, halogeno lower-alkoxy-methyl groups, low-alkoxilated ethyl groups, halogenated ethyl groups, methyl groups that have undergone substitution by 1 to 3 aryl groups, "methyl groups that have undergone substitution by 1 to 3 aryl groups in which an aryl ring has undergone substitution by a lower alkyl group, lower alkoxy group, halogen atom, or cyano group", lower-alkoxy-carbonyl groups, "aryl groups that have undergone substitution by a halogen atom, lower alkoxy group, or nitro group", "lower-alkoxy-carbonyl groups that have undergone substitution by a halogen atom or tri-lower-alkyl-silyl group", alkenyloxycarbonyl groups, "aralkyloxycarbonyl groups in which an aryl ring has optionally undergone substitution by a lower alkoxy group or nitro group", "lower-alkoxy-carbonyl groups that have undergone substitution by a cyano group", and "benzenesulfonyl groups that have undergone substitution by 1 to 4 nitro groups".

More specific examples of the tetrahydropyranyl or tetrahydrothiopyranyl groups include a tetrahydropyran-2-yl group, a 3-bromotetrahydropyran-2-yl group, a 4-methoxytetrahydropyran-4-yl group, a tetrahydrothiopyran-4-yl group, and a 4-methoxytetrahydrothiopyran-4-yl group. Examples of the tetrahydrofuranyl or tetrahydrothiofuranyl groups include a tetrahydrofuran-2-yl group and a tetrahydrothiofuran-2-yl group. Examples of the lower-alkoxy-methyl groups include a methoxymethyl group, a 1,1-dimethyl-1-methoxymethyl group, an ethoxymethyl group, a propoxymethyl group, an isopropoxymethyl group, a butoxymethyl group, and a t-butoxymethyl group. An example of the low-alkoxilated lower-alkoxy-methyl groups is a 2-methoxyethoxymethyl group. Examples of the halogeno lower-alkoxy-methyl groups include a 2,2,2-trichloroethoxymethyl group and a bis(2-chloroethoxy)methyl group. Examples of the low-alkoxilated ethyl groups include a 1-ethoxyethyl group and a 1-(isopropoxy)ethyl group. An example of the halogenated ethyl groups is a 2,2,2-trichloroethyl group. Examples of the methyl groups that have undergone substitution by 1 to 3 aryl groups include a benzyl group, an α-naphthylmethyl group, a β-naphthylmethyl group, a diphenylmethyl group, a triphenylmethyl group, an α-naphthyldiphenylmethyl group, and a 9-anthrylmethyl group. Examples of the "methyl groups that have undergone substitution by 1 to 3 aryl groups in which an aryl ring has undergone substitution by a lower alkyl group, lower alkoxy group, halogen atom, or cyano group" include a 4-methylbenzyl group, a 2,4,6-trimethylbenzyl group, a 3,4,5-trimethylbenzyl group, a 4-methoxybenzyl group, a 4-methoxyphenyldiphenylmethyl group, a 4,4'-dimethoxytriphenylmethyl group, a 2-nitrobenzyl group, a 4-nitrobenzyl group, a 4-chlorobenzyl group, a 4-bromobenzyl group, and a 4-cyanobenzyl group. Examples of the lower-alkoxy-carbonyl groups include a methoxycarbonyl group, an ethoxycarbonyl group, a t-butoxycarbonyl group, and an isobutoxycarbonyl group. Examples of the "aryl groups that have undergone substitution by a halogen atom, lower alkoxy group, or nitro group" include a 4-chlorophenyl group, a 2-fluorophenyl group, a 4-methoxyphenyl group, a 4-nitrophenyl group, and a 2,4-dinitrophenyl group. Examples of the "lower-alkoxy-carbonyl groups that have undergone substitution by a halogen atom or tri-lower-alkyl-silyl group" include a 2,2,2-trichloroethoxycarbonyl group and 2-trimethylsilylethoxycarbonyl group. Examples of the alkenyloxycarbonyl groups include a vinyloxycarbonyl group and an aryloxycarbonyl group. Examples of the "aralkyloxycarbonyl groups in which an aryl ring has optionally undergone substitution by a lower alkoxy group or nitro group" include a benzyloxycarbonyl group, a 4-methoxybenzyloxycarbonyl group, a 3,4-dimethoxybenzyloxycarbonyl group, a 2-nitrobenzyloxycarbonyl group, and a 4-nitrobenzyloxycarbonyl group. An example of the "lower-alkoxy-carbonyl groups that have undergone substitution by a cyano group" is a cyanoethoxycarbonyl group. Examples of the "benzenesulfonyl groups that have undergone substitution by 1 to 4 nitro groups" include a 2-nitrobenzenesulfonyl group and a 2,4-dinitrobenzenesulfonyl group.

The "hydroxy group protecting group for nucleic acid synthesis" is favorably an aliphatic acyl group, an aromatic acyl group, a methyl group that has undergone substitution by 1 to 3 aryl groups, a "methyl group that has undergone substitution by 1 to 3 aryl groups in which an aryl ring has undergone substitution by a lower alkyl, lower alkoxy, halogen, or cyano group", or a silyl group, and more favorably an acetyl group, a benzoyl group, a benzyl group, a p-methoxybenzoyl group, a dimethoxytrityl group, a monomethoxytrityl group, or a tert-butyldiphenylsilyl group. The protecting group used for the "hydroxy group protected by a protecting group for nucleic acid synthesis" is favorably an aliphatic acyl group, an aromatic acyl group, a "methyl group that has undergone substitution by 1 to 3 aryl groups", an "aryl group that has undergone substitution by a halogen atom, lower alkoxy group, or nitro group", a lower alkyl group, or a lower alkenyl group, and more favorably a benzoyl group, a benzyl group, a 2-chlorophenyl group, a 4-chlorophenyl group, or a 2-propenyl group. The "amino group protecting group for nucleic acid synthesis" is favorably an acyl group, and more favorably a benzoyl group. The "protecting group" used for the "phosphate group protected by a protecting group for nucleic acid synthesis" is favorably a lower alkyl group, a lower alkyl group that has undergone substitution by a cyano group, an aralkyl group, an "aralkyl group in which an aryl ring has undergone substitution by a nitro group or halogen atom", or an "aryl group that has undergone substitution by a lower alkyl group, halogen atom, or nitro group", and more favorably a 2-cyanoethyl group, a 2,2,2-trichloroethyl group, a benzyl group, a 2-chlorophenyl group, or a 4-chlorophenyl group. One or more protecting groups may be used for the "phosphate group protected by a protecting group for nucleic acid synthesis". The "protecting group" used for the "mercapto group protected by a protecting group for nucleic acid synthesis" is favorably an aliphatic acyl group or an aromatic acyl group, and more favorably a benzoyl group.

Examples of the "amino group protecting group" for the $R^{IO}$ group in this specification include an acetyl group, a tertiary butoxycarbonyl (Boc) group, and a 9-fluorenylmethyloxycarbonyl (Fmoc) group.

In this specification, among groups represented by $-P(R^{24})R^{25}$ (where the $R^{24}$ and the $R^{25}$ independently represent a hydroxy group, a hydroxy group protected by a protecting group for nucleic acid synthesis, a mercapto group, a mercapto group protected by a protecting group for nucleic acid synthesis, an amino group, a linear or branched alkoxy group having 1 to 6 carbon atoms, a linear or branched alkylthio group having 1 to 6 carbon atoms, a cyanoalkoxy group having 1 to 6 carbon atoms, or a linear or branched alkylamino group having 1 to 6 carbon atoms), a group in which the $R^{24}$ can be represented as $-OR^{24a}$ and the $R^{25}$ can be represented as $-N(R^{25a})_2$ is referred to as a "phosphoramidite group". Favorable examples of the phosphoramidite group include a group represented by a formula $-P(OC_2H_4CN)(N(iPr)_2)$ and a group represented by a formula $-P(OCH_3)(N(iPr)_2)$. In these formulae, iPr represents an isopropyl group.

The term "nucleoside" as used herein encompasses "nucleosides" in which a purine base or a pyrimidine base binds to sugar, as well as those in which a heteroaromatic ring and an aromatic hydrocarbon ring other than purine and pyrimidine, serving as a substitute for a purine base or a pyrimidine base, binds to sugar. A natural nucleoside is also referred to as a "native nucleoside". A modified non-natural nucleoside is also referred to as a "modified nucleoside", and in particular, a nucleotide in which a sugar moiety is modified is referred to as a "sugar-modified nucleoside". The term "nucleotide" means a compound obtained through binding of a phosphate group to sugar of a nucleoside.

The term "oligonucleotide" as used herein refers to a polymer of "nucleotides" in which two to fifty of the same or different "nucleosides" are bound via phosphodiester bonds or other bonds, and encompasses natural oligonucleotides and non-natural oligonucleotides. Preferable examples of the non-natural "oligonucleotides" include sugar derivatives with sugar moieties modified, thiolated derivatives with phosphate diester moieties thiolated; esters with terminal phosphate moieties esterificated; and amides in which amino groups on purine bases are amidated. The sugar derivatives with sugar moieties modified are more favorable.

The term "salts thereof" as used herein refers to salts of compounds represented by Formula (II), which will be shown later. Examples of such salts include metal salts including alkali metal salts such as sodium salts, potassium salts, and lithium salts, alkali earth metal salts such as calcium salts and magnesium salts, and aluminum salts, iron salts, zinc salts, copper salts, nickel salts, and cobalt salts; amine salts including inorganic salts such as ammonium salts, and organic salts such as t-octylamine salts, dibenzylamine salts, morpholine salts, glucosamine salts, phenylglycine alkylester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts, and tris(hydroxymethyl)aminomethane salts; inorganic acid salts including halide hydroacid salts such as hydrofluoric acid salts, hydrochloric acid salt, hydrobromic acid salts, and hydroiodic acid salts, nitrates, perchlorates, sulfates, and phosphates; organic acid salts including lower-alkanesulfonates such as methanesulfonates, trifluoromethanesulfonates, and ethanesulfonates, arylsulfonates such as benzenesulfonates and p-toluenesulfonates, acetates, malates, fumarates, succinates, citrates, tartrates, oxalates and maleates; and amino acid salts such as glycine salts, lysine salts, arginine salts, ornithine salts, glutamates, and aspartates.

The term "pharmacologically acceptable salts thereof" refers to physiologically and pharmaceutically acceptable salts of oligonucleotides according to the present including at least one nucleoside structure represented by Formula (I) below, that is, salts that keep desired biological activity of those oligonucleotides and do not exhibit undesired toxic effects. Examples of such salts include metal salts including alkali metal salts such as sodium salts, potassium salts, and lithium salts, alkali earth metal salts such as calcium salts and magnesium salts, and aluminum salts, iron salts, zinc salts, copper salts, nickel salts, and cobalt salts; amine salts including inorganic salts such as ammonium salts, and organic salts such as t-octylamine salts, dibenzylamine salts, morpholine salts, glucosamine salts, phenylglycine alkylester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts, and tris(hydroxymethyl)aminomethane salts; inorganic acid salts including halide hydroacid salts such as hydrofluoric acid salts, hydrochloric acid salt, hydrobromic acid salts, and hydroiodic acid salts, nitrates, perchlorates, sulfates, and phosphates; organic acid salts including lower-alkane-sulfonates such as methanesulfonates, trifluoromethanesulfonates, and ethanesulfonates, arylsulfonates such as benzenesulfonates and p-toluenesulfonates, acetates, malates, fumarates, succinates, citrates, tartrates, oxalates and maleates; and amino acid salts such as glycine salts, lysine salts, arginine salts, ornithine salts, glutamates, and aspartates.

Hereinafter, the present invention will be described in detail.

The present invention provides an oligonucleotide that can bind to the nSR100 gene and has nSR100 expression inhibiting activity. Such an oligonucleotide may be in the form of a pharmacologically acceptable salt thereof. Regarding the nSR100 gene, the base sequence information of the human nSR100 ("hnSR100") gene is available as GenBank Accession No.: NM_194286.3, and is shown as SEQ ID No. 1 in the sequence list. The term "binding to the nSR100 gene" as used herein encompasses all of direct binding to the nSR100 gene, binding to the mRNA of the nSR100 gene, and binding to an mRNA precursor of the nSR100 gene, for example. The term "can bind to the nSR100 gene and have nSR100 expression inhibiting activity" encompasses a case where an expression inhibitor binds to the nSR100 mRNA transcribed from the nSR100 gene and then RNase H acts on and degrades the RNA, so that the expression level of the nSR100 mRNA is reduced, for example. The nSR100 gene expression inhibiting activity (knockdown activity) can be measured using a known method (e.g., quantitative reverse transcription-polymerase chain reaction (qRT-PCR)). When an oligonucleotide having nSR100 gene expression inhibiting activity (knockdown activity) is used in the in vitro mRNA expression experiment described in 3-1 in Example 3 or 4-2 in Example 4 below, or in equivalent experiments, for example, the expression level of the nSR100 mRNA in human SLCL cells may be concentration-dependent, but is lower than that in the case (control) where the antisense oligonucleotide is not added, and may be 0.8 or less, preferably 0.7 or less, and more preferably 0.6 or less, for example, when the nSR100 mRNA level in human SLCL cells in the control is taken as 1.

The term "can bind to" as used herein means that a plurality of different single-stranded oligonucleotides or nucleic acids can form a nucleic acid including two or more strands due to the complementarity between the bases of the nucleic acids. Favorably, it means that a double-stranded nucleic acid can be formed. There is no particular limitation on the melting temperature ($T_m$), which is an index for the thermal stability of a bond, of the nucleic acid including two or more strands. The melting temperature ($T_m$) of a double-stranded nucleic acid can be determined as described below, for example. Equimolar amounts of an oligonucleotide and a target RNA are mixed in a buffer solution (8.1 mM $Na_2HPO_4$, 2.68 mM KCl, 1.47 mM $KH_2PO_4$, pH 7.2). The resultant mixture is heated at 95° C. for 5 minutes, and then allowed to cool slowly to room temperature, so that annealing is performed, forming a double-stranded nucleic acid. The temperature of the double-stranded nucleic acid is raised from 20° C. to 95° C. at a rate of 0.5° C./minute, and changes in absorbance (A) at 260 nm relative to the temperature (T) are measured. A graph of dA/dT vs T is drawn based on the measurement results, and the temperature at which the value of dA/dT is the largest, that is, the temperature at which a change in A relative to T is the largest, is taken as $T_m$ of the double-stranded nucleic acid. The melting temperature ($T_m$) is 40° C. or higher, for example, and preferably 50° C. or higher.

The term "complementary" as used herein means that two different single-stranded oligonucleotides or nucleic acids have such a paring relationship that they can form a double-stranded nucleic acid. It is preferable that the base sequences of the regions that form a double-stranded product is completely complementary to each other, but there may be one or several mismatches therebetween as long as the double-stranded nucleic acid can be formed and the expression inhibiting function is exhibited. The term "one or several mismatches" means one to four mismatches, preferably one to three mismatches, and more preferably one or two mismatches, which may depend on the length of the oligonucleotide. It is preferable that the oligonucleotide of the present invention is completely (100%) complementary to the base sequence of the region for forming a double-stranded product.

An example of an oligonucleotide that can bind to the nSR100 gene and has nSR100 gene expression inhibiting activity is an antisense oligonucleotide (ASO) targeting the nSR100 gene. An antisense oligonucleotide (ASO) is a single-stranded oligonucleotide that can bind to the RNA (e.g., mRNA or mRNA precursor)/DNA of a target gene, has activity for inhibiting the expression of the target gene, and is complementary to the sequence of the RNA (e.g., mRNA or mRNA precursor)/DNA of the target gene.

The oligonucleotide according to the present invention can bind to a target region corresponding to a portion of the sequence represented by SEQ ID No. 1. A predetermined "target region" encompasses all of a DNA in a predetermined region shown in SEQ ID No. 1, and an mRNA and an mRNA precursor that correspond to the DNA The target region is preferably a region in human nSR100 that relates particularly to nSR100 expression inhibiting activity or knockdown activity. For example, the target region for the oligonucleotide according to the present invention has a length of 12 to 20 mer, preferably a length of 13 to 20 mer, more preferably 14 to 20 mer, and even more preferably 15 to 19 mer, but the number of bases in the region is not limited thereto. The term "binding to a target region" related to a nucleic acid molecule or oligonucleotide does not necessarily mean that the nucleic acid molecule or oligonucleotide forms a product including two or more strands (preferably two strands) together with the entire target region, and may mean that the nucleic acid molecule or oligonucleotide forms a product including two or more strands (preferably two strands) together with a portion of the target region as long as nSR100 gene expression inhibiting activity or knockdown activity is exhibited. The oligonucleotide that can bind to the nSR100 gene and has nSR100 gene expression inhibiting activity is complementary to a target region, for example, and it is preferable that the oligonucleotide is completely complementary to the target region.

The oligonucleotide (e.g., antisense oligonucleotide) according to the present invention has a length of 12 to 20 mer, for example, preferably a length of 13 to 20 mer, more preferably 14 to 20 mer, and even more preferably 15 to 19 mer. The oligonucleotide with a length as mentioned above can more efficiently bind to the nSR100 gene and suppress (e.g., knock down) the mRNA expression.

The oligonucleotide (e.g., antisense oligonucleotide) according to the present invention is an oligonucleotide that can bind to the nSR100 gene and has nSR100 gene expression inhibiting activity, and includes a sequence that is complementary to a target region having a 12- to 20-mer continuous sequence in a base sequence from position 600 to position 620, from position 640 to position 700, from position 710 to position 800, from position 1060 to position 1080, from position 1560 to position 1600, from position 1630 to position 1660, from position 1685 to position 1720, from position 1850 to position 1900, from position 2900 to position 2925, from position 3835 to position 3875, from position 4800 to position 4830, from position 5900 to position 5970, from position 6010 to position 6035, from position 6230 to position 6270, from position 6300 to position 6320, from position 6440 to position 6470, from position 6750 to position 6772, from position 6865 to position 6890, from position 7045 to position 7080, from position 7130 to position 7155, from position 7160 to position 7220, from position 7360 to position 7390, from position 7680 to position 7850, from position 7950 to position 7980, from position 7995 to position 8020 or from position 8160 to position 8180 in SEQ ID No. 1, for example. In one embodiment, the oligonucleotide (e.g., antisense oligonucleotide) according to the present invention includes a sequence that is complementary to a target region having a 12- to 20-mer continuous sequence in a base sequence from position 604 to position 618, from position 680 to position 694, from position 712 to position 800, from position 1064 to position 1078, from position 1566 to position 1580, from position 1582 to position 1598, from position 1633 to position 1659, from position 1689 to position 1711, from position 1858 to position 1877, from position 2906 to position 2920, from position 3841 to position 3868, from position 4810 to position 4824, from position 5907 to position 5922, from position 5950 to position 5964, from position 6015 to position 6029, from position 6239 to position 6254, from position 6302 to position 6316, from position 6448 to position 6462, from position 6755 to position 6769, from position 6870 to position 6884, from position 7057 to position 7074, from position 7130 to position 7150, from position 7166 to position 7192, from position 7203 to position 7217, from position 7365 to position 7387, from position 7688 to position 7702, from position 7733 to position 7748, from position 7769 to position 7783, from position 7792 to position 7808, from position 7827 to position 7843, from position 7959 to position 7974, from position 8001 to position 8015, or from position 8165 to position 8179. In one embodiment, the 5' end of a target region for the oligonucleotide (e.g., antisense oligonucleotide) according to the present invention corresponds to position 7168, position 7170, position 7172, or position 7174 in SEQ ID No. 1, and the oligonucleotide has a length of 15 to 19 mer. A method that is commonly used by a person skilled in the art can be used to design the sequence of an antisense oligonucleotide based on the selected target region.

The following sequences (bases are aligned in a direction from 5' toward 3') are examples of the base sequence of the antisense oligonucleotide (target regions are shown together as "5'-end position –3'-end position" using the numbers of the base positions in SEQ ID No. 1).

ttcttttcttcttt (SEQ ID No. 2) (712-726);
atttcttcttttct (SEQ ID No. 3) (717-731);
gtggatttcttcttt (SEQ ID No. 4) (721-735);
tcttcttttcttga (SEQ ID No. 5) (780-794);
tcttcttcttttct (SEQ ID No. 6) (783-797);
ttttcttcttcttt (SEQ ID No. 7) (786-800);
ttgtgtgactgaagc (SEQ ID No. 8) (7174-7188);
aatttgtgtgactga (SEQ ID No. 9) (7177-7191);
ttgtgtgactgaagcct (SEQ ID No. 10) (7172-7188);
ttgtgtgactgaagcctcc (SEQ ID No. 11) (7170-7188);
gtgtgactgaagcct (SEQ ID No. 12) (7172-7186);
gtgtgactgaagcctcc (SEQ ID No. 13) (7170-7186);
gtgtgactgaagcctccat (SEQ ID No. 14) (7168-7186);
gtgactgaagcctcc (SEQ ID No. 15) (7170-7184);
gtgactgaagcctccat (SEQ ID No. 16) (7168-7184);
gtgactgaagcctccattt (SEQ ID No. 17) (7166-7184);
atttgtgtgactgaa (SEQ ID No. 18) (7176-7190);
atttgtgtgactgaagc (SEQ ID No. 19) (7174-7190);
atttgtgtgactgaagcct (SEQ ID No. 20) (7172-7190);
taatttgtgtgactg (SEQ ID No. 21) (7178-7192);
caactgttggtgccc (SEQ ID No. 22) (604-618);
tggtgtcaagtcttt (SEQ ID No. 23) (680-694);
gcagagggtcttgga (SEQ ID No. 24) (1064-1078);
tgctggcataggagg (SEQ ID No. 25) (1566-1580);

tgactggaggatcgg (SEQ ID No. 26) (1582-1596);
agtgactggaggatc (SEQ ID No. 27) (1584-1598);
cgggctttgggtgtac (SEQ ID No. 28) (1633-1647);
gaagaggtggatcgg (SEQ ID No. 29) (1645-1659);
acttggaggaatagc (SEQ ID No. 30) (1689-1703);
gacttggaggaatag (SEQ ID No. 31) (1690-1704);
cttgccagacttgga (SEQ ID No. 32) (1697-1711);
tttctcataggcgag (SEQ ID No. 33) (1858-1872);
ggcgctttctcatag (SEQ ID No. 34) (1863-1877);
catgctgaggtattg (SEQ ID No. 35) (2906-2920);
ggaaagattgggtag (SEQ ID No. 36) (3841-3855);
ggttgataggatggg (SEQ ID No. 37) (3854-3868);
acaagggatttcgac (SEQ ID No. 38) (4810-4824);
tggtgatctgtcata (SEQ ID No. 39) (5907-5921);
ctggtgatctgtcat (SEQ ID No. 40) (5908-5922);
ggatgttggttttg (SEQ ID No. 41) (5950-5964);
agcgggaaggtcaaa (SEQ ID No. 42) (6015-6029);
tcgtttttactttca (SEQ ID No. 43) (6239-6253);
ttcgtttttactttc (SEQ ID No. 44) (6240-6254);
aataggggcttttga (SEQ ID No. 45) (6302-6316);
aaatgaagtgatgcg (SEQ ID No. 46) (6448-6462);
cataagtttctcagc (SEQ ID No. 47) (6755-6769);
acagcaaccacagat (SEQ ID No. 48) (6870-6884);
ccaattctcaatagc (SEQ ID No. 49) (7057-7071);
ggaccaattctcaat (SEQ ID No. 50) (7060-7074);
gtgattctagcactc (SEQ ID No. 51) (7130-7144);
ggtgattctagcact (SEQ ID No. 52) (7131-7145);
ttggtgattctagca (SEQ ID No. 53) (7133-7147);
cttggtgattctagc (SEQ ID No. 54) (7134-7148);
gcttggtgattctag (SEQ ID No. 55) (7135-7149);
tgcttggtgattcta (SEQ ID No. 56) (7136-7150);
ccagtgttttagttc (SEQ ID No. 57) (7203-7217);
aagatgaggcatagc (SEQ ID No. 58) (7365-7379);
ctcgttagaagatga (SEQ ID No. 59) (7373-7387);
tatatgactgtggga (SEQ ID No. 60) (7688-7702);
caggatacaagagtt (SEQ ID No. 61) (7733-7747);
ccaggatacaagagt (SEQ ID No. 62) (7734-7748);
gagagaagttcaaac (SEQ ID No. 63) (7769-7783);
atgactttggaccac (SEQ ID No. 64) (7792-7806);
tgatgactttggacc (SEQ ID No. 65) (7794-7808);
cagggcaaggtaagc (SEQ ID No. 66) (7827-7841);
agcagggcaaggtaa (SEQ ID No. 67) (7829-7843);
tgggcatgtcaactc (SEQ ID No. 68) (7959-7973);
ttgggcatgtcaact (SEQ ID No. 69) (7960-7974);
atgttggacattgag (SEQ ID No. 70) (8001-8015); and
atggccttggggtgc (SEQ ID No. 71) (8165-8179).

One to several bases (e.g., two or three bases) may be added to the 5' end and/or 3' end of the sequence mentioned above as long as the oligonucleotide can bind to the nSR100 gene and has nSR100 expression inhibiting activity. These additional bases can be complementary to the bases of a sequence, shown in SEQ ID No. 1, adjacent to the target region having a sequence to which the bases are to be added.

The oligonucleotide according to the present invention encompasses an oligonucleotide containing a chemically modified DNA Such a modification can change the activity of the oligonucleotide and, for example, can improve the affinity for a target nucleic acid or improve the tolerance to a nucleic acid degradation enzyme (nuclease). Improving the affinity of the oligonucleotide for a target makes it possible to enable the use of a shorter oligonucleotide.

The oligonucleotide according to the present invention includes at least one sugar-modified nucleoside at any position. This sugar-modified nucleoside includes a cross-link as described below, for example, between position 2 and position 4 in the sugar ring.

In one embodiment, the oligonucleotide according to the present invention includes at least one nucleoside structure represented by Formula (I) below as a sugar-modified nucleoside.

[Chemical Formula 11]

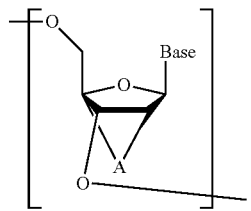
(I)

In this Formula,

Base represents a purin-9-yl group that may have any one or more substituents selected from an α group, or a 2-oxo-1,2-dihydropyrimidin-1-yl group that may have any one or more substituents selected from the a group, the a group consisting of a hydroxy group, a hydroxy group protected by a protecting group for nucleic acid synthesis, linear alkyl groups having 1 to 6 carbon atoms, linear alkoxy groups having 1 to 6 carbon atoms, a mercapto group, a mercapto group protected by a protecting group for nucleic acid synthesis, linear alkylthio groups having 1 to 6 carbon atoms, an amino group, linear alkylamino groups having 1 to 6 carbon atoms, an amino group protected by a protecting group for nucleic acid synthesis, and halogen atoms, and A is a divalent group represented by:

[Chemical Formula 12]

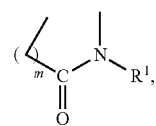
(a-1)

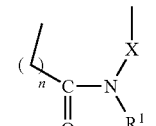
(a-2)

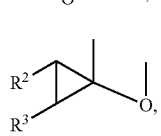
(b-1)

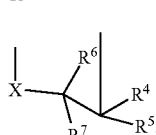
(c-1)

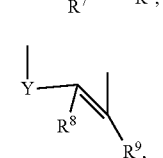
(c-2)

(d-1)

[structure d-1: N with NR¹⁶ and (NHR¹⁶)⁺ subscript p, and N-R¹⁰]

or (e-1)

[structure e-1: R¹³, R¹⁴, and O]

where R¹ represents a hydrogen atom, an alkyl group having 1 to 7 carbon atoms that may form a branch or a ring, an alkenyl group having 2 to 7 carbon atoms that may form a branch or a ring, an aryl group having 3 to 12 carbon atoms that may have any one or more substituents selected from the a group and optionally has a hetero atom, an aralkyl group with an aryl moiety having 3 to 12 carbon atoms that may have any one or more substituents selected from the a group and optionally has a hetero atom, or an amino group protecting group for nucleic acid synthesis; R² and R³ are independently a hydrogen atom, an alkyl group having 1 to 7 carbon atoms that has optionally undergone substitution by an aryl group having 3 to 12 carbon atoms that may include a hetero atom and that may form a branch or a ring, or an aralkyl group with an aryl moiety having 3 to 12 carbon atoms that may include a hetero atom, or R² and R³ represent —(CH$_2$)$_q$— [where q is an integer from 2 to 5] together;

R⁴ and R⁵ are independently a group selected from the group consisting of a hydrogen atom, a hydroxy group, alkyl groups having 1 to 7 carbon atoms that optionally form a branch or a ring, alkoxy groups having 1 to 7 carbon atoms that optionally form a branch or a ring, an amino group, and an amino group protected by a protecting group for nucleic acid synthesis, or R⁴ and R⁵ form =C(R¹¹)R¹² [where R¹¹ and R¹² independently represent a hydrogen atom, a hydroxy group, a hydroxy group protected by a protecting group for nucleic acid synthesis, a mercapto group, a mercapto group protected by a protecting group for nucleic acid synthesis, an amino group, a linear or branched alkoxy group having 1 to 6 carbon atoms, a linear or branched alkylthio group having 1 to 6 carbon atoms, a cyanoalkoxy group having 1 to 6 carbon atoms, or a linear or branched alkylamino group having 1 to 6 carbon atoms] together;

R⁶ and R⁷ are independently a hydrogen atom, an alkyl group having 1 to 7 carbon atoms that may form a branch or a ring, an alkoxy group having 1 to 7 carbon atoms that may form a branch or a ring, or a linear or branched alkylthio group having 1 to 6 carbon atoms;

R⁸ represents a hydrogen atom, an alkyl group having 1 to 7 carbon atoms that may form a branch or a ring, an alkoxy group having 1 to 7 carbon atoms that may form a branch or a ring, or a linear or branched alkylthio group having 1 to 6 carbon atoms;

R⁹ is a hydrogen atom, a hydroxy group, an alkyl group having 1 to 7 carbon atoms that may form a branch or a ring, an alkoxy group having 1 to 7 carbon atoms that may form a branch or a ring, an amino group, or an amino group protected by a protecting group for nucleic acid synthesis;

R¹⁰ is an alkyl group having 1 to 7 carbon atoms that may form a branch or a ring, an amino group protecting group, or

[Chemical Formula 13]

[structure: ester linkage with OCH₂CH₂CN]

or

—(C=(NHR¹⁷)+)—NR¹⁸R¹⁹ [where R¹⁷, R¹⁸, and R¹⁹ are independently a hydrogen atom, an alkyl group having 1 to 7 carbon atoms that may form a branch or a ring, an amino group protecting group, or

[Chemical Formula 14]

[structure: ester linkage with OCH₂CH₂CN]
];

R¹³ and R¹⁴ are independently a group selected from the group consisting of a hydrogen atom, a hydroxy group, alkyl groups having 1 to 7 carbon atoms that optionally form a branch or a ring, alkoxy groups having 1 to 7 carbon atoms that optionally form a branch or a ring, an amino group, and an amino group protected by a protecting group for nucleic acid synthesis;

m is an integer from 0 to 2;

n is an integer of 0 to 1;

when R¹⁰ is a hydrogen atom, an alkyl group having 1 to 7 carbon atoms that may form a branch or a ring, an amino group protecting group, or

[Chemical Formula 15]

[structure: ester linkage with OCH₂CH₂CN]

p is 1, and R¹⁵ and R¹⁶ are independently a hydrogen atom, an alkyl group having 1 to 7 carbon atoms that may form a branch or a ring, an amino group protecting group, or

[Chemical Formula 16]

[structure: ester linkage with OCH₂CH₂CN]

or when R¹⁰ is —(C=(NHR¹⁷)+)—NR¹⁸R¹⁹ [where R¹⁷, R¹⁸, and R¹⁹ are independently a hydrogen atom, an alkyl group having 1 to 7 carbon atoms that may form a branch or a ring, an amino group protecting group, or

[Chemical Formula 17]

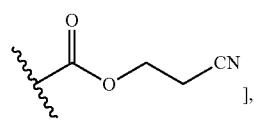

], p is 0;

X is an oxygen atom, a sulfur atom, or an amino group; and

Y is an oxygen atom or a sulfur atom.

In one embodiment, the nucleoside structure represented by Formula (I) above is a structure represented by

[Chemical Formula 18]

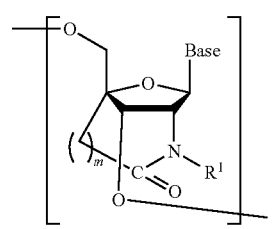
(I-1)

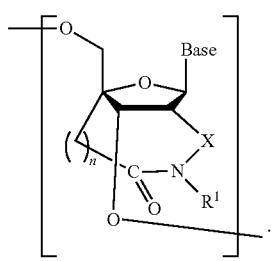
(I-2)

Base, $R^1$, X, m, and n in Formulae (I-1) and (I-2) are the same as those in Formula (I) described above. An amide (—$CONR^1$—) is introduced into the cross-link between position 2' and position 4', and such a nucleoside structure is also referred to as an "amide bridged nucleic acid", an "amide BNA (Bridged Nucleic Acid)", or "AmNA".

In Formulae (I-1) and (I-2), $R^1$ is a hydrogen atom, an alkyl group having 1 to 7 carbon atoms that may form a branch or a ring, an alkenyl group having 2 to 7 carbon atoms that may form a branch or a ring, an aryl group having 3 to 12 carbon atoms that may have any one or more substituents selected from the a group and optionally has a hetero atom, or an aralkyl group with an aryl moiety having 3 to 12 carbon atoms that may have any one or more substituents selected from the a group and optionally has a hetero atom. $R^1$ is more favorably a hydrogen atom, a methyl group, an ethyl group, an n-propyl group, an isopropyl group, a phenyl group, or a benzyl group, and even more favorably a hydrogen atom or a methyl group.

In Formula (I-1), m is an integer from 0 to 2, and in Formula (I-2), n is an integer of 0 to 1. That is, a ring including position 2', position 3', position 4', and a cross-linked portion is a five- to seven-membered ring.

In Formula (I-2), X is an oxygen atom, a sulfur atom, an amino group, or a methylene group. X is favorably an oxygen atom or an amino group. It should be noted that, when X is an amino group or a methylene group, X has optionally undergone substitution by a lower alkyl group.

In one embodiment, the nucleoside structure represented by Formula (I) above is a structure represented by Formula (I-1) above, and in this Formula (I-1), m is 0, and $R^1$ is a hydrogen atom, a methyl group, an ethyl group, an n-propyl group, an isopropyl group, a phenyl group, or a benzyl group.

In the compounds represented by Formulae (I-1) and (1-2), an amide bond is formed between the amino group at position 2' and a carbonyl group extending from position 4' in a sugar moiety. An amide bond, which has little structural fluctuation and excellent hydrophilicity, is provided, and therefore, the structure of the sugar moiety in the nucleoside is fixed by the cross-link.

Examples of the nucleoside structure represented by Formula (I) above include those represented by Formulae (I-3) to (I-7) in addition to those represented by Formulae (I-1) and (1-2).

[Chemical Formula 19]

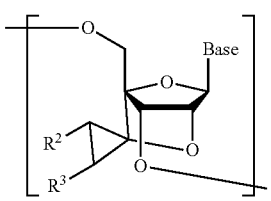
(I-3)

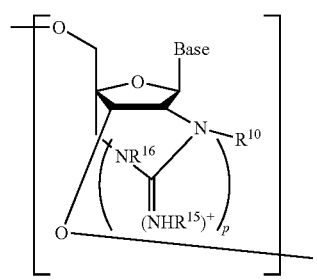
(I-4)

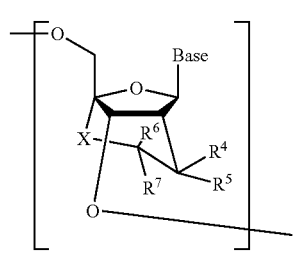
(I-5)

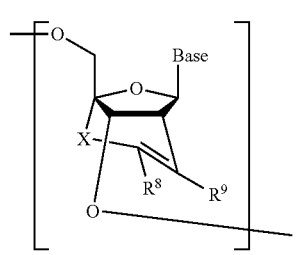
(I-6)

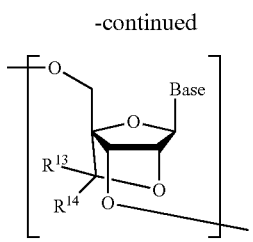

(I-7)

In the formulae above, Base, $R^2$, $R^3$, $R^4$, $R^5$, $R^6$, $R^7$, $R^8$, $R^9$, $R^{10}$, $R^{13}$, $R^{14}$, $R^{15}$, $R^{16}$, and p are the same as those in Formula (I) described above. Formula (I-7) corresponds to a nucleoside structure called a 2',4'-BNA or an LNA (Locked Nucleic Acid) (also referred to as a "2',4'-BNA/LNA" or "LNA" in this specification) (in one example, both $R^{13}$ and $R^{14}$ are hydrogen atoms). Formula (I-3) shows a structure obtained by introducing a spirocyclopropane group into position 6' of the cross-link structure of a 2',4'-BNA/LNA, and this structure is also called a spirocyclopropane bridged nucleic acid (spcBNA). Formula (I-4) shows a structure obtained by introducing a guanidine into the cross-link structure of a 2',4'-BNA/LNA, and this structure is also called a guanidine bridged nucleic acid (GuNA). It should be noted that Formula (I-4) encompasses Formulae (I-4-1) (p=0) and (I-4-2) (p=1).

[Chemical Formula 20]

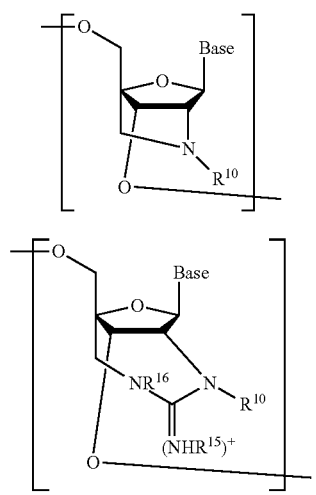

"Base" above is a purine base (i.e., purin-9-yl group) or a pyrimidine base (i.e., 2-oxo-1,2-dihydropyrimidin-1-yl group). These bases optionally have any one or more substituents selected from the a group consisting of a hydroxy group, linear alkyl groups having 1 to 6 carbon atoms, linear alkoxy groups having 1 to 6 carbon atoms, a mercapto group, linear alkylthio groups having 1 to 6 carbon atoms, an amino group, linear alkylamino groups having 1 to 6 carbon atoms, and halogen atoms.

Specific examples of the "Base" above include an adeninyl group, a guaninyl group, a cytosinyl group, an uracilyl group, a thyminyl group, a 6-aminopurin-9-yl group, a 2,6-diaminopurin-9-yl group, a 2-amino-6-chloropurin-9-yl group, a 2-amino-6-fluoropurin-9-yl group, a 2-amino-6-bromopurin-9-yl group, a 2-amino-6-hydroxypurin-9-yl group, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl group, a 4-amino-2-oxo-5-fluoro-1,2-dihydropyrimidin-1-yl group, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl group, a 2-oxo-4-hydroxy-5-methyl-1,2-dihydropyrimidin-1-yl group, and a 4-amino-5-methyl-2-oxo-1,2-dihydropyrimidin-1-yl group.

In particular, as the "Base", groups represented by structural formulae below:

[Chemical Formula 21]

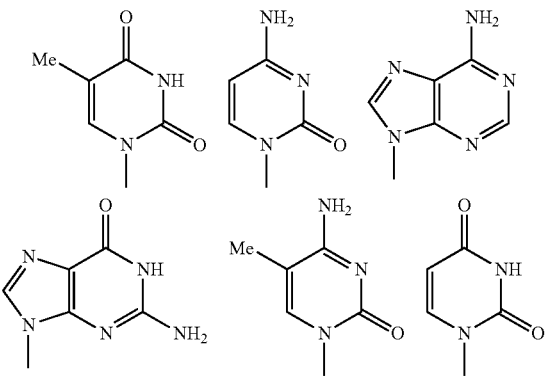

(i.e., a thyminyl group, a cytosinyl group, an adeninyl group, a guaninyl group, a 5-methylcytosinyl group, and an uracilyl group), and a 2-oxo-4-hydroxy-5-methyl-1,2-dihydropyrimidin-1-yl group, a 2-oxo-4-amino-1,2-dihydropyrimidin-1-yl group, a 6-aminopurin-9-yl group, a 2-amino-6-hydroxypurin-9-yl group, a 4-amino-5-methyl-2-oxo-1,2-dihydropyrimidin-1-yl group, and a 2-oxo-4-hydroxy-1,2-dihydropyrimidin-1-yl group are favorable, and a 2-oxo-4-hydroxy-5-methyl-1,2-dihydropyrimidin-1-yl group and a thyminyl group are particularly favorable. It is preferable that a hydroxy group and an amino group are protected by a protecting group during oligonucleotide synthesis.

It should be noted that, in one embodiment, when the oligonucleotide according to the present invention includes, as a sugar-modified nucleoside, the nucleoside structure represented by Formula (I-4), or Formula (I-4-1) or Formula (I-4-2) above, the nucleoside structure represented by Formula (I-4), or Formula (I-4-1) or Formula (I-4-2) is kept electrically neutral by an anion (e.g., represented as $Z^-$) that is not shown in Formula (I-4), or Formula (I-4-1) or Formula (I-4-2). Examples of such an anion include halide ions (e.g., chloride ion) and a phosphate ion.

The oligonucleotide including at least one sugar-modified nucleoside structure as described above can be synthesized using a sugar-modified nucleoside compound and using the methods disclosed in WO 2011/052436, JP 2014-043462A, WO 2014/046212, and WO 2015/125783, for example.

Examples of the sugar-modified nucleoside compound include compounds represented by Formula (II) below, or salts thereof:

[Chemical Formula 22]

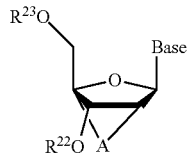
(II)

(where

Base represents a purin-9-yl group that may have any one or more substituents selected from an a group, or a 2-oxo-1,2-dihydropyrimidin-1-yl group that may have any one or more substituents selected from the a group, the a group consisting of a hydroxy group, a hydroxy group protected by a protecting group for nucleic acid synthesis, linear alkyl groups having 1 to 6 carbon atoms, linear alkoxy groups having 1 to 6 carbon atoms, a mercapto group, a mercapto group protected by a protecting group for nucleic acid synthesis, linear alkylthio groups having 1 to 6 carbon atoms, an amino group, linear alkylamino groups having 1 to 6 carbon atoms, an amino group protected by a protecting group for nucleic acid synthesis, and halogen atoms, and A is a divalent group represented by:

[Chemical Formula 23]

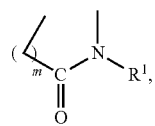
(a-1)

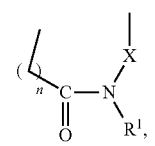
(a-2)

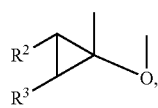
(b-1)

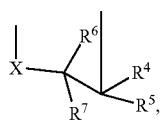
(c-1)

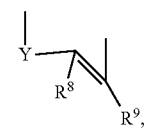
(c-2)

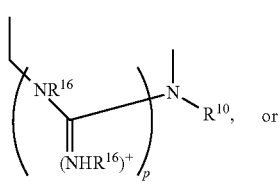
(d-1)

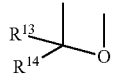
(e-1)

where $R^1$ represents a hydrogen atom, an alkyl group having 1 to 7 carbon atoms that may form a branch or a ring, an alkenyl group having 2 to 7 carbon atoms that may form a branch or a ring, an aryl group having 3 to 12 carbon atoms that may have any one or more substituents selected from the a group and optionally has a hetero atom, an aralkyl group with an aryl moiety having 3 to 12 carbon atoms that may have any one or more substituents selected from the a group and optionally has a hetero atom, or an amino group protecting group for nucleic acid synthesis;

$R^2$ and $R^3$ are independently a hydrogen atom, an alkyl group having 1 to 7 carbon atoms that has optionally undergone substitution by an aryl group having 3 to 12 carbon atoms that may include a hetero atom and that may form a branch or a ring, or an aralkyl group with an aryl moiety having 3 to 12 carbon atoms that may include a hetero atom, or $R^2$ and $R^3$ represent $-(CH_2)_q-$ [where q is an integer from 2 to 5] together;

$R^4$ and $R^5$ are independently a group selected from the group consisting of a hydrogen atom, a hydroxy group, alkyl groups having 1 to 7 carbon atoms that optionally form a branch or a ring, alkoxy groups having 1 to 7 carbon atoms that optionally form a branch or a ring, an amino group, and an amino group protected by a protecting group for nucleic acid synthesis, or $R^4$ and $R^5$ form $=C(R^{11})R^{12}$ [where $R^{11}$ and $R^{12}$ independently represent a hydrogen atom, a hydroxy group, a hydroxy group protected by a protecting group for nucleic acid synthesis, a mercapto group, a mercapto group protected by a protecting group for nucleic acid synthesis, an amino group, a linear or branched alkoxy group having 1 to 6 carbon atoms, a linear or branched alkylthio group having 1 to 6 carbon atoms, a cyanoalkoxy group having 1 to 6 carbon atoms, or a linear or branched alkylamino group having 1 to 6 carbon atoms] together;

$R^6$ and $R^7$ are independently a hydrogen atom, an alkyl group having 1 to 7 carbon atoms that may form a branch or a ring, an alkoxy group having 1 to 7 carbon atoms that may form a branch or a ring, or a linear or branched alkylthio group having 1 to 6 carbon atoms;

$R^8$ represents a hydrogen atom, an alkyl group having 1 to 7 carbon atoms that may form a branch or a ring, an alkoxy group having 1 to 7 carbon atoms that may form a branch or a ring, or a linear or branched alkylthio group having 1 to 6 carbon atoms;

$R^9$ is a hydrogen atom, a hydroxy group, an alkyl group having 1 to 7 carbon atoms that may form a branch or a ring, an alkoxy group having 1 to 7 carbon atoms that may form a branch or a ring, an amino group, or an amino group protected by a protecting group for nucleic acid synthesis;

$R^{10}$ is a hydrogen atom, an alkyl group having 1 to 7 carbon atoms that may form a branch or a ring, an amino group protecting group, or

[Chemical Formula 24]

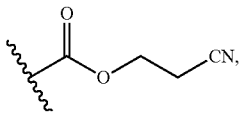

or

—(C=(NHR$^{17}$)+)—NR$^{18}$R$^{19}$ [where R$^{17}$, R$^{18}$, and R$^{19}$ are independently a hydrogen atom, an alkyl group having 1 to 7 carbon atoms that may form a branch or a ring, an amino group protecting group, or

[Chemical Formula 25]

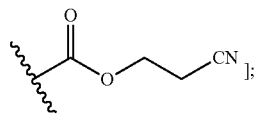

R$^{13}$ and R$^{14}$ are independently a group selected from the group consisting of a hydrogen atom, a hydroxy group, alkyl groups having 1 to 7 carbon atoms that optionally form a branch or a ring, alkoxy groups having 1 to 7 carbon atoms that optionally form a branch or a ring, an amino group, and an amino group protected by a protecting group for nucleic acid synthesis;

m is an integer from 0 to 2;
n is an integer of 0 to 1;
when R$^{10}$ is a hydrogen atom, an alkyl group having 1 to 7 carbon atoms that may form a branch or a ring, an amino group protecting group, or

[Chemical Formula 26]

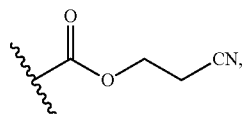

p is 1, and R$^{15}$ and R$^{16}$ are independently a hydrogen atom, an alkyl group having 1 to 7 carbon atoms that may form a branch or a ring, an amino group protecting group, or

[Chemical Formula 27]

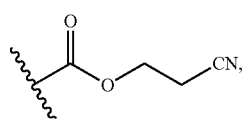

or when R$^{10}$ is —(C=(NHR$^{17}$)+)—NR$^{18}$R$^{19}$ [where R$^{17}$, R$^{18}$, and R$^{19}$ are independently a hydrogen atom, an alkyl group having 1 to 7 carbon atoms that may form a branch or a ring, an amino group protecting group, or

[Chemical Formula 28]

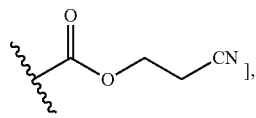

p is 0;
X is an oxygen atom, a sulfur atom, or an amino group;
Y is an oxygen atom or a sulfur atom;
R$^{22}$ and R$^{23}$ independently represent a hydrogen atom, a hydroxy group protecting group for nucleic acid synthesis, an alkyl group having 1 to 7 carbon atoms that may form a branch or a ring, an alkenyl group having 2 to 7 carbon atoms that may form a branch or a ring, an aryl group having 3 to 12 carbon atoms that may have any one or more substituents selected from the a group and optionally has a hetero atom, an aralkyl group with an aryl moiety having 3 to 12 carbon atoms that may have any one or more substituents selected from the a group and optionally has a hetero atom, an acyl group that may have any one or more substituents selected from the a group, a silyl group that may have any one or more substituents selected from the a group, a phosphate group that may have any one or more substituents selected from the a group, a phosphate group protected by a protecting group for nucleic acid synthesis, or —P(R$^{24}$)R$^{25}$ [where R$^{24}$ and R$^{25}$ independently represent a hydroxy group, a hydroxy group protected by a protecting group for nucleic acid synthesis, a mercapto group, a mercapto group protected by a protecting group for nucleic acid synthesis, an amino group, an alkoxy group having 1 to 5 carbon atoms, an alkylthio group having 1 to 5 carbon atoms, a cyanoalkoxy group having 1 to 6 carbon atoms, or a dialkylamino group that has undergone substitution by an alkyl group having 1 to 6 carbon atoms]).

A sugar-modified nucleotide can be easily prepared using the sugar-modified nucleosides as described above. For example, thiophosphorylation can be easily performed in accordance with the method described in M. Kuwahara et al., Nucleic Acids Res., 2008, vol. 36, No. 13, pp. 4257-65.

The nucleotide modifications known in the art other than the above-mentioned modification to sugar can also be used. A modification to phosphate and a modification to a nucleic acid base are known as the nucleotide modifications. Such modifications to a nucleic acid can be performed based on methods known in the art.

Examples of the modification to phosphate include a phosphodiester bond included in a native nucleic acid, S-oligo(phosphorothioate), D-oligo(phosphodiester), M-oligo(methylphosphonate), and boranophosphate. S-oligo(phosphorothioate) includes a PS backbone in which an oxygen atom in the phosphate group moiety of the phosphodiester bond between nucleosides is substituted by a sulfur atom. This modification is introduced into an oligonucleotide in accordance with a known method. An antisense oligonucleotide that includes this modification at one or more positions in the oligonucleotide is referred to as an S-oligo type (phosphorothioate type).

Examples of the modification to a nucleic acid base include 5-methylcytosine, 5-hydroxymethylcytosine, and 5-propynylcytosine.

There is no particular limitation on the positions and number of the sugar-modified nucleosides in the oligonucleotide of the present invention, and the oligonucleotide can be designed as appropriate depending on the purpose. Two or more sugar-modified nucleosides may be the same or different.

It is preferable that the oligonucleotide of the present invention is a gapmer (particularly in the case of a single-stranded oligonucleotide). The "gapmer" means an oligonucleotide including a "gap", which is a central region, and two wings, which are regions located on both sides of the gap, namely a "5' wing" located on the 5' side and a "3' wing" located on the 3' side. The gap region can have a length of 6 to 15 mer, and the wing regions can have a length of 3 to 5 mer. The gap is constituted by native nucleosides, and the wings can include at least one modified nucleotide.

The oligonucleotide of the present invention includes at least one sugar-modified nucleoside, preferably 1 to 5 sugar-modified nucleosides, in the "5' wing" and/or the "3' wing". In one embodiment, the gapmer can include a gap region having 9 to 13 bases, a 5' wing having 3 to 5 bases, and a 3' wing having 3 to 5 bases, the gap region can be located between the 5' wing and the 3' wing, and the 5' wing and the 3' wing each can have at least one nucleoside structure represented by Formula (I) above. In addition, the gapmer may include a modification to phosphate, a modification to a base, and the like. The types, number, and positions of modifications in one wing may be the same as or different from those in the other wing. The "wings" of the gapmer may be a wing in which all the bases included are modified nucleotides, or a wing in which some of the bases included are native nucleosides, and also encompasses a wing (e.g., 3-9-2-1) in which one base at the 3' end of the 3' wing is a native nucleoside (e.g., DNA).

Examples of such a gapmer include, but are not limited to, 3-6-3, 3-6-2-1, 3-7-3, 3-7-2-1, 3-8-2-1, 3-8-3-1, 3-8-3, 3-9-2-1, 3-9-3, 3-9-3-1, 3-10-2-1, 3-10-3, 3-11-2-1, 3-11-3, 3-12-2-1, 3-12-3, 3-13-2-1, 3-13-3, 4-11-3-1, 4-11-4, and 5-10-5. For example, "3-9-2-1" refers to a gapmer in which nine bases constituting the gap are native nucleosides (DNAs), the 5' wing (three bases on the 5' end side) is constituted by sugar-modified nucleosides, three bases close to the center in the 3' wing (three bases on the 3' end) are sugar-modified nucleosides, and the last one base (the base of the 3'-end) is a native nucleoside (DNA). For example, "3-9-3" refers to a gapmer in which nine bases constituting the gap are native nucleosides (DNAs), the 5' wing (three bases on the 5' end side) is constituted by sugar-modified nucleosides, and 3' wing (three bases on the 3' end side) is constituted by sugar-modified nucleosides. It is preferable to use 3-9-2-1, 3-9-3, 3-10-2-1, 3-10-3, 3-11-2-1, 3-11-3, 3-12-2-1, 3-12-3, 3-13-2-1, or 3-13-3, but this can depend on the sequence.

In one embodiment, the nucleoside structure represented by Formula (I) above is

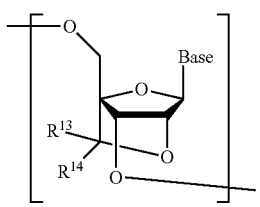
[Chemical Formula 29]

(where both $R^{13}$ and $R^{14}$ are hydrogen atoms);

[Chemical Formula 30]

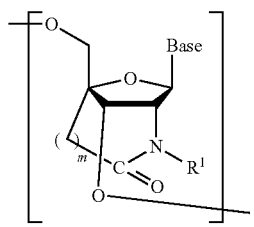

(where m is 0, and $R^1$ is a hydrogen atom, a methyl group, an ethyl group, an n-propyl group, an isopropyl group, a phenyl group, or a benzyl group);

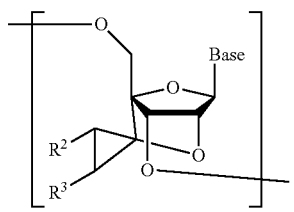
[Chemical Formula 31]

(where $R^2$ and $R^3$ are independently a hydrogen atom, an alkyl group having 1 to 7 carbon atoms that has optionally undergone substitution by an aryl group having 3 to 12 carbon atoms that may include a hetero atom and that may form a branch or a ring, or an aralkyl group with an aryl moiety having 3 to 12 carbon atoms that may include a hetero atom, or $R^2$ and $R^3$ represent —$(CH_2)_q$— [where q is an integer from 2 to 5] together); or

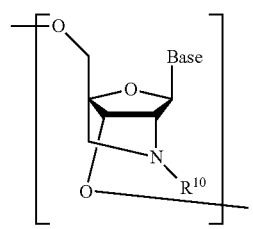
[Chemical Formula 32]

(where $R^{10}$ is —(C=(NHR$^{17}$)+)—NR$^{18}$R$^{19}$, where $R^{17}$ and $R^{18}$ are independently a hydrogen atom or an alkyl group having 1 to 7 carbon atoms that may form a branch or a ring, and $R^{19}$ is a hydrogen atom).

In one embodiment, the oligonucleotide according to the present invention is an oligonucleotide that includes a base sequence represented by any of the base sequences of SEQ ID Nos. 2 to 71 described above, and in which at least one of the bases is the sugar-modified nucleoside mentioned above. The following sequences are examples of such an oligonucleotide:

nSR100L #1/hnSR100-712-LNA(15) (SEQ ID No. 76),
hnSR100L #2/hnSR100-717-LNA(15) (SEQ ID No. 77),
hnSR100L #3/hnSR100-721-LNA(15) (SEQ ID No. 78),
hnSR100L #4/hnSR100-780-LNA(15) (SEQ ID No. 79),
hnSR100L #5/hnSR100-783-LNA(15) (SEQ ID No. 80),
hnSR100L #6/hnSR100-786-LNA(15) (SEQ ID No. 81),
hnSR100L #21/hnSR100-7174-LNA(15) (SEQ ID No. 96),
hnSR100L #22/hnSR100-7177-LNA(15) (SEQ ID No. 97),
hnSR100-7170-LNA(19) (SEQ ID No. 124),
hnSR100-7172-LNA(15) (SEQ ID No. 125),
hnSR100-7170-LNA(17) (SEQ ID No. 126),
hnSR100-7168-LNA(19) (SEQ ID No. 127),
hnSR100-7170-LNA(15) (SEQ ID No. 128),
hnSR100-7168-LNA(17) (SEQ ID No. 129),
hnSR100-7166-LNA(19) (SEQ ID No. 130),
hnSR100-7176-LNA(15) (SEQ ID No. 131),
hnSR100-7174-LNA(17) (SEQ ID No. 132), hnSR100-7172-LNA(19) (SEQ ID No. 133),
hnSR100-7178-LNA(15) (SEQ ID No. 134),
hnSR100-7174-AmNA(15) (SEQ ID No. 152),
hnSR100-7172-AmNA(17) (SEQ ID No. 153),
hnSR100-7170-AmNA(19) (SEQ ID No. 154),
hnSR100-7172-AmNA(15) (SEQ ID No. 155),
hnSR100-7170-AmNA(17) (SEQ ID No. 156),
hnSR100-7168-AmNA(19) (SEQ ID No. 157),
hnSR100-7170-AmNA(15) (SEQ ID No. 158),
hnSR100-7168-AmNA(17) (SEQ ID No. 159),
hnSR100-7174-AmNA(17) (SEQ ID No. 162),
hnSR100-7172-AmNA(19) (SEQ ID No. 163),
hnSR100-680-LNA(15) (SEQ ID No. 168),
hnSR100-1064-LNA(15) (SEQ ID No. 169),
hnSR100-3841-LNA(15) (SEQ ID No. 170),
hnSR100-3854-LNA(15) (SEQ ID No. 171),
hnSR100-604-AmNA(15) (SEQ ID No. 172),
hnSR100-1566-AmNA(15) (SEQ ID No. 173),
hnSR100-1582-AmNA(15) (SEQ ID No. 174),
hnSR100-1584-AmNA(15) (SEQ ID No. 175),
hnSR100-1633-AmNA(15) (SEQ ID No. 176),
hnSR100-1645-AmNA(15) (SEQ ID No. 177),
hnSR100-1689-AmNA(15) (SEQ ID No. 178),
hnSR100-1690-AmNA(15) (SEQ ID No. 179),
hnSR100-1697-AmNA(15) (SEQ ID No. 180),
hnSR100-1858-AmNA(15) (SEQ ID No. 181),
hnSR100-1863-AmNA(15) (SEQ ID No. 182),
hnSR100-2906-AmNA(15) (SEQ ID No. 183),
hnSR100-4810-AmNA(15) (SEQ ID No. 184),
hnSR100-5907-AmNA(15) (SEQ ID No. 185),
hnSR100-5908-AmNA(15) (SEQ ID No. 186),
hnSR100-5950-AmNA(15) (SEQ ID No. 187),
hnSR100-6015-AmNA(15) (SEQ ID No. 188),
hnSR100-6239-AmNA(15) (SEQ ID No. 189),
hnSR100-6240-AmNA(15) (SEQ ID No. 190),
hnSR100-6302-AmNA(15) (SEQ ID No. 191),
hnSR100-6448-AmNA(15) (SEQ ID No. 192),
hnSR100-6755-AmNA(15) (SEQ ID No. 193),
hnSR100-6870-AmNA(15) (SEQ ID No. 194),
hnSR100-7057-AmNA(15) (SEQ ID No. 195),
hnSR100-7060-AmNA(15) (SEQ ID No. 196),
hnSR100-7130-AmNA(15) (SEQ ID No. 197),
hnSR100-7131-AmNA(15) (SEQ ID No. 198),
hnSR100-7133-AmNA(15) (SEQ ID No. 199),
hnSR100-7134-AmNA(15) (SEQ ID No. 200),
hnSR100-7135-AmNA(15) (SEQ ID No. 201),
hnSR100-7136-AmNA(15) (SEQ ID No. 202),
hnSR100-7203-AmNA(15) (SEQ ID No. 203),
hnSR100-7365-AmNA(15) (SEQ ID No. 204),
hnSR100-7373-AmNA(15) (SEQ ID No. 205),
hnSR100-7688-AmNA(15) (SEQ ID No. 206),
hnSR100-7733-AmNA(15) (SEQ ID No. 207),
hnSR100-7734-AmNA(15) (SEQ ID No. 208),
hnSR100-7769-AmNA(15) (SEQ ID No. 209),
hnSR100-7792-AmNA(15) (SEQ ID No. 210)
hnSR100-7794-AmNA(15) (SEQ ID No. 211),
hnSR100-7827-AmNA(15) (SEQ ID No. 212),
hnSR100-7829-AmNA(15) (SEQ ID No. 213),
hnSR100-7859-AmNA(15) (SEQ ID No. 214),
hnSR100-7860-AmNA(15) (SEQ ID No. 215),
hnSR100-8001-AmNA(15) (SEQ ID No. 216),
hnSR100-8165-AmNA(15) (SEQ ID No. 217),
hnSR100-7174-AmNA, scpBNA(15) (SEQ ID No. 218), or
hnSR100-7174-AmNA, GuNA(15) (SEQ ID No. 219).

In the oligonucleotides listed above, "LNA" represents an oligonucleotide including a nucleic acid represented by Formula (a) below. "AmNA" represents an oligonucleotide including a nucleic acid represented by Formula (b) below. "AmNA, scpBNA" represents an oligonucleotide including a nucleic acid (AmNA) represented by Formula (b) below and a nucleic acid (scpBNA) represented by Formula (c) below. "AmNA, GuNA" represents an oligonucleotide including a nucleic acid (AmNA) represented by Formula (b) below and a nucleic acid (GuNA) represented by Formula (d) below.

The oligonucleotide according to the present invention can be synthesized from the above-described sugar-modified nucleosides and native nucleosides using an ordinary method. For example, the oligonucleotide according to the present invention can be easily synthesized using a commercially available automated nucleic acid synthesizer (manufactured by Applied Biosystems, GeneDesign Inc., or the like, for example). Solid phase synthesis using phosphoroamidite, solid phase synthesis using hydrogen phosphonate, and the like are used as the synthesis method. For example, the methods disclosed in Tetrahedron Letters, 1981, vol. 22. pp. 1859-1862, WO 2011/052436, WO 2014/046212, WO 2015/125783, and the like can be used.

The present invention encompasses an nSR100 expression inhibitor containing the oligonucleotide mentioned above or a pharmacologically acceptable salt thereof. In addition, the present invention encompasses a cancer therapeutic agent containing the oligonucleotide mentioned above, a pharmacologically acceptable salt thereof, or the nSR100 expression inhibitor. Regarding the nSR100 expression inhibitor, any administration method and formulation known in the art can be used as an administration method and formulation of the nSR100 expression inhibitor or cancer therapeutic agent of the present invention. These can be administered using various methods for a topical or systemic treatment, or depending on regions to be treated.

The cancer therapeutic agent of the present invention can be administered using various methods for a topical or systemic treatment, or depending on regions to be treated. Examples of the administration method include topical administration (including ocular instillation, intravaginal administration, intrarectal administration, intranasal administration, and percutaneous administration), oral administration, and parenteral administration. Examples of parenteral administration include intravenous injection, intravenous instillation, subcutaneous transfusion, intraabdominal transfusion, intramuscular transfusion, pulmonary administration via the airway through aspiration or inhalation.

The cancer therapeutic agent of the present invention can be topically administered using formulations such as a percutaneous patch, ointment, lotion, cream, gel, drops, suppository, spray, liquid medicine, and powder medicine.

Examples of compositions for oral administration include powder medicine, granular medicine, a suspension or solution obtained through dissolution in water or a non-aqueous medium, a capsule, powdered medicine, and a tablet.

Examples of compositions for parenteral administration include sterile aqueous solutions containing a buffer, a diluent, and other appropriate additives.

The cancer therapeutic agent of the present invention can be obtained by mixing an effective dose of the oligonucleotide mentioned above, a pharmacologically acceptable salt thereof, or the nSR100 expression inhibitor and various pharmaceutical additives suitable for the dosage form, such as a vehicle, a binding agent, a moistening agent, a disintegrating agent, a lubricant, and a diluent. In the case of an injection, it is sufficient that a formulation is prepared by performing sterilization together with an appropriate carrier.

The cancer therapeutic agent of the present invention can be used for treatment or prevention of cancerous diseases related to the nSR100 gene expression. Examples of the cancerous diseases related to the nSR100 gene expression include small cell lung cancer, prostate cancer (e.g., castration-resistant prostate cancer (CRPC)), and breast cancer. Such cancerous diseases can be derived from neuroendocrine cells.

The present invention provides a method for inhibiting the nSR100 gene expression. The present invention also provides a method for treating or preventing a cancerous disease. In one embodiment, these methods are used for treatment of cancerous diseases (e.g., small cell lung cancer, prostate cancer and breast cancer) related to the nSR100 gene expression. These methods include a step of administrating the oligonucleotide mentioned above or a pharmacologically acceptable salt thereof to an individual. The "individual" is preferably a mammal, more preferably a human, monkey, dog, cat, rat, or mouse, and even more preferably a human. In these methods, there is no limitation on the administration method and dosage form as long as an effective dose of the oligonucleotide of the present invention is administered. Although the effective administration dose depends on the individual to which the oligonucleotide is to be administered, the effective administration dose can be determined as desired in accordance with the sex, age, weight, symptom and the like of the individual, and the method, route, frequency and the like of the administration. The administration methods and the like are as described above.

In the treatment of cancerous diseases (e.g., small cell lung cancer, prostate cancer, and breast cancer) related to the nSR100 gene expression, diagnosis based on the nSR100 gene can also be used together. In such diagnosis, miRNAs (e.g., at least one of miR-4279 (e.g., cucuccucc ggcuuc (SEQ ID No. 72)), miR-4419b (e.g., gaggcugaag gaagaugg (SEQ ID No. 73)), miR-4516 (e.g., gggagaaggg ucggggc (SEQ ID No. 74)), and miR-4635 (e.g., ucuugaaguc agaacccgca a (SEQ ID No. 75))) that are detected specifically in patients with the cancerous disease mentioned above (particularly, small cell lung cancer) can be used as index markers. It is preferable to use miR-4516. The diagnostic agent and the diagnostic method disclosed in Patent Document 1 can be used for this diagnosis, for example. Using such diagnosis together enables early diagnosis and treatment, and thus the cancerous diseases mentioned above can be more effectively treated.

EXAMPLES

Hereinafter, the present invention will be described byway of examples, but the present invention is not limited thereto.

Example 1: Oligonucleotide Synthesis

Oligonucleotides related to the present invention were synthesized using the methods disclosed in Tetrahedron Letters 22, 1859-1862 (1981), WO 2011/052436, and the like.

Specifically, the synthesis of oligonucleotides containing a 2',4'-BNA/LNA represented by Formula (a) was entrusted to GeneDesign Inc.

[Chemical Formula 33]

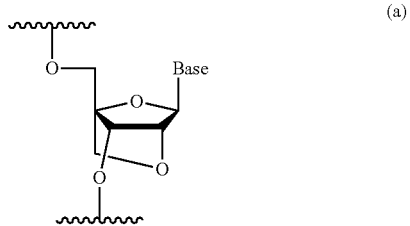

(a)

(where Base is a 5-methylcytosinyl group, thyminyl group, adeninyl group, or guaninyl group.)

Oligonucleotides containing an amide BNA (AmNA) represented by Formula (b) were synthesized with reference to the method disclosed in WO 2011/052436.

[Chemical Formula 34]

(b)

(where Base is a 5-methylcytosinyl group, thyminyl group, adeninyl group, or guaninyl group, and Me is a methyl.)

15- to 19-mer oligonucleotides containing a 2',4'-BNA/LNA represented by Formula (a) or an amide BNA (AmNA) represented by Formula (b) were synthesized at 0.2 μmol scale using an automated nucleic acid synthesizer (Type nS-8, manufactured by GeneDesign Inc.). The strand length was elongated in accordance with a standard phosphoroamidite protocol (solid phase support: CPG resin; DDT (3H-1,2-Benzodithiole-3-one, 1,1-dioxide) or the like was used in sulfurization for forming a phosphorothioated (PS) backbone), and thus an oligonucleotide in which a hydroxy group at the 5' end was protected by a DMTr (dimethoxytrityl) group and the 3' end was held in the solid phase was obtained. Next, the DMTr group was removed through acid treatment, and base treatment was performed to remove target products from the solid phase support. After neutralization using dilute acid, the solvent was distilled off, and then the resultant crude product was purified using gel filtration column chromatography and reversed phase HPLC. The target products were thus obtained.

The cross-linked structure of the LNA or AmNA used in this example and the purities and structures of the obtained oligonucleotides were confirmed using HPLC and MALDI-TOF-MS (manufactured by BRUKER DALTONICS).

Example 2: Antisense Oligonucleotide Design

Antisense oligonucleotides targeting the mRNA of human nSR100 (hnSR100) (GenBank: NM_194286.3 (SEQ ID No. 1)) were designed.

In order to select target regions, the reverse sequences (CG, GGA, and GCA) of CG, TCC, and TGC were excluded since CG, TCC, and TGC are toxic in an antisense strand. Then, regions such as a loop structure that are easy for an antisense oligonucleotide to reach were selected based on the secondary structure predicted using mfold (mfold: unafold.rna.albany.edu/?q=mfold). Next, regions of the nSR100 gene corresponding to portions that are highly homologous between the human mRNA and the mouse mRNA were mainly selected using Blast (BLAST: https #blast.ncbi.nlm.nih.gov/Blast.cgi?PAGE_TYPE=BlastSearch) such that the evaluation results obtained from mice could be applied to humans. In this manner, twenty-two candidate sequences were selected.

Oligonucleotides having base sequences complementary to the candidate sequences selected as mentioned above were designed as antisense oligonucleotides. Each of the antisense oligonucleotides had a length of 15 mer, and was provided with artificial nucleic acid regions containing sugar-modified nucleosides at the 5' end and the 3' end and a native nucleic acid region containing native nucleosides (DNAs) in the central portion. More specifically, a 3-9-2-1 gapmer was designed in which three bases on the 5' end side (5' wing region) are sugar-modified nucleosides, subsequent nine bases (gap region) are native nucleosides (DNAs), two bases close to the center in subsequent three bases on the 3' end side (3' wing region) are sugar-modified nucleosides, and one base at the 3' end is a native nucleoside.

Table 1 shows the sequences of designed antisense oligonucleotides (in the direction from 5' toward 3') and the base positions in SEQ ID No. 1 corresponding to the 5' ends and the 3' ends of the sequences of the target regions for the antisense oligonucleotides. In the oligonucleotides shown in Table 1, a 2',4'-BNA/LNA (also referred to merely as "LNA") was used as the sugar-modified nucleoside.

TABLE 1

| Oligonucleotide Name | Antisense (5'→3') | Target Seq. 5'-end | Target Seq. 3'-end | SEQ.ID. No. |
|---|---|---|---|---|
| hnSR100L#1<br>hnSR100-712-LNA(15) | T(L)^T(L)^5(L)^t^t^t^t^t^c^t^t^c^T(L)^T(L)^t | 712 | 726 | 76 |
| hnSR100L#2<br>hnSR100-717-LNA(15) | A(L)^T(L)^T(L)^t^c^t^t^c^t^t^t^t^T(L)^5(L)^t | 717 | 731 | 77 |
| hnSR100L#3<br>hnSR100-721-LNA(15) | G(L)^T(L)^G(L)^g^a^t^t^t^c^t^t^c^T(L)^T(L)^t | 721 | 735 | 78 |
| hnSR100L#4<br>hnSR100-780-LNA(15) | T(L)^5(L)^T(L)^t^c^t^t^t^t^t^t^c^t^T(L)^G(L)^a | 780 | 794 | 79 |
| hnSR100L#5<br>hnSR100-783-LNA(15) | T(L)^5(L)^T(L)^t^c^t^t^c^t^t^t^t^t^T(L)^5(L)^t | 783 | 797 | 80 |
| hnSR100L#6<br>hnSR100-786-LNA(15) | T(L)^T(L)^T(L)^t^c^t^t^c^t^t^c^t^T(L)^T(L)^t | 786 | 800 | 81 |
| hnSR100L#7<br>hnSR100-1185-LNA(15) | T(L)^T(L)^T(L)^t^g^g^t^a^a^a^g^a^G(L)^G(L)^t | 1185 | 1199 | 82 |
| hnSR100L#8<br>hnSR100-1389-LNA(15) | G(L)^T(L)^G(L)^a^g^g^a^g^g^t^g^g^T(L)^G(L)^a | 1389 | 1403 | 83 |
| hnSR100L#9<br>hnSR100-1518-LNA(15) | G(L)^G(L)^G(L)^c^t^g^t^g^g^a^t^g^G(L)^G(L)^a | 1518 | 1532 | 84 |
| hnSR100L#10<br>hnSR100-1660-LNA(15) | T(L)^A(L)^G(L)^g^a^c^c^t^t^t^t^t^T(L)^5(L)^a | 1660 | 1674 | 85 |
| hnSR100L#11<br>hnSR100-1663-LNA(15) | G(L)^A(L)^G(L)^t^a^g^g^a^c^c^t^t^T(L)^T(L)^t | 1663 | 1677 | 86 |
| hnSR100L#12<br>hnSR100-3590-LNA(15) | G(L)^T(L)^T(L)^t^a^t^t^t^t^a^a^g^G(L)^A(L)^t | 3590 | 3604 | 87 |
| hnSR100L#13<br>hnSR100-3593-LNA(15) | A(L)^G(L)^A(L)^g^t^t^t^a^t^t^t^t^A(L)^A(L)^g | 3593 | 3607 | 88 |
| hnSR100L#14<br>hnSR100-3844-LNA(15) | A(L)^T(L)^G(L)^g^g^a^a^a^g^a^t^t^G(L)^G(L)^g | 3844 | 3858 | 89 |
| hnSR100L#15<br>hnSR100-3847-LNA(15) | A(L)^G(L)^G(L)^a^t^g^g^g^a^a^a^g^A(L)^T(L)^t | 3847 | 3861 | 90 |
| hnSR100L#16<br>hnSR100-4291-LNA(15) | T(L)^A(L)^A(L)^a^t^a^a^a^a^a^g^g^T(L)^T(L)^t | 4291 | 4305 | 91 |
| hnSR100L#17<br>hnSR100-4294-LNA(15) | A(L)^A(L)^A(L)^t^a^a^a^t^a^a^a^a^A(L)^G(L)^g | 4294 | 4308 | 92 |
| hnSR100L#18<br>hnSR100-4297-LNA(15) | A(L)^T(L)^A(L)^a^a^a^t^a^a^a^t^a^A(L)^A(L)^a | 4297 | 4311 | 93 |

TABLE 1-continued

| Oligonucleotide Name | Antisense (5'→3') | Target Seq. 5'-end | Target Seq. 3'-end | SEQ.ID. No. |
|---|---|---|---|---|
| hnSR100L#19<br>hnSR100-4367-LNA(15) | A(L)Â(L)Â(L)t̂âââtââtt̂5(L)Â(L)â | 4367 | 4381 | 94 |
| hnSR100L#20<br>hnSR100-4370-LNA(15) | T(L)Â(L)T̂(L)âââtâââtâA(L)T̂(L)t̂ | 4370 | 4384 | 95 |
| hnSR100L#21<br>hnSR100-7174-LNA(15) | T(L)T̂(L)Ĝ(L)t̂ĝt̂âĉt̂ĝâA(L)Ĝ(L)ĉ | 7174 | 7188 | 96 |
| hnSR100L#22<br>hnSR100-7177-LNA(15) | A(L)Â(L)T̂(L)t̂t̂ĝt̂ĝt̂ĝâcT(L)Ĝ(L)â | 7177 | 7191 | 97 |

"5" represents 5-methylcytosine(5mC).
A(L), G(L), 5(L) and T(L) represent 2',4'-BNA/LNA-type bases.
a, g, c and t represent DNA-type bases.
"^" represents a phosphorothioated site.

The sequences of the antisense oligonucleotides shown in Table 1 correspond to SEQ ID. Nos. 76 to 97 in the order from top to bottom. In hnSR100-p-n(L) in Table 1, which represents an antisense oligonucleotide, "p" corresponds to the base position number in SEQ ID No. 1 corresponding to the 5' end of the target region, "n" represents a sugar-modified nucleoside (artificial nucleic acid) ("LNA" in Table 1), and "L" represents the length of the antisense oligonucleotide. For example, in the case of hnSR100-7174-LNA(15), position 7174 of the base sequence of SEQ ID No. 1 corresponds to the 5' end of the target region, an LNA is contained, and the length is 15 mer. In Table 1, the antisense oligonucleotide with the sequence name "hnSR100L #21" is also referred to as "hnSR100-7174-LNA(15)", and therefore, "hnSR100L #21" or "hnSR100-7174-LNA(15)" is used to represent this antisense oligonucleotide, or alternatively, "hnSR100L #21/hnSR100-7174-LNA(15)" is also used. In the case where the sequences of the antisense oligonucleotides are shown extending in the direction from 5' toward 3'(5'-3'), the antisense oligonucleotide of hnSR100-7174 having a length of 15 mer, for example, was designed by arranging bases that were complementary to 15 bases extending toward the 3' end from position 7174 of the base sequence of SEQ ID No. 1. That is, this antisense oligonucleotide was designed to have a base sequence (5'-ttgtgtgactgaagc-3') (SEQ ID No. 8) that is complementary to a target mRNA sequence 5'-gcuucagucacacaa-3' (SEQ ID No. 99) based on the DNA base sequence 5'-gcttcagtcacacaa-3'(SEQ ID No. 98) from position 7174 to position 7188 of SEQ ID No. 1. The base sequence (5'-ttgtgtgactgaagc-3') (SEQ ID No. 8) of the antisense oligonucleotide hnSR100-7174-LNA(15) designed as described above is complementary to the base sequence (5'-gcttcagt-cacacaa-3') (SEQ ID No. 98) of a region from position 7174 to position 7188 of SEQ ID No. 1.

It should be noted that the term "phosphorothioated" means that a structure is formed in which an oxygen atom in a phosphate group in a phosphodiester bond is substituted by a sulfur atom (a group corresponding to a phosphate group is referred to as a "phosphorothioate group"). In this specification, an oligonucleotide in which all the phosphate groups in the oligonucleotide are substituted by phosphorothioate groups is particularly referred to as an "S-oligonucleotide". All the oligonucleotides shown in Table 1 are S-oligonucleotides.

Example 3: Suppression of nSR100 mRNA Expression in Human SCLC Cells In Vitro 3-1: Analysis of Suppression of mRNA Expression by Various Antisense Oligonucleotides Suppression of nSR100 mRNA expression by the antisense oligonucleotides prepared in Example 2 in human SCLC cells in vitro was examined. NCI-H82 cells (American Type Culture Collection: ATCC), STC-1 cells (ATCC), and NCI-N417 cells (ATCC) were used as the human SCLC cells. A case where the oligonucleotides were not added was taken as a control. For comparison, an N26 oligonucleotide (base sequence: 5'-TGAacaaaataaTAc-3'; in this example, a base represented by an uppercase letter is a 2',4'-BNA/LNA, a base represented by a lowercase letter is a DNA, and this oligonucleotide is an S-oligonucleotide; SEQ ID No. 100) was used.

The CEM method ("$Ca^{2+}$ enrichment for medium" a method in which a calcium ion-rich medium is used: Nucleic Acids Research, 2015, Vol. 43, e 128) was used to introduce each of the antisense oligonucleotides into the human SCLC cells, the qRT-PCR method was used to measure the mRNA expression level, and thus knockdown activity (suppression of mRNA expression) was examined. The following describes the procedure.

The human SCLC cells in a logarithmic growth phase were seeded in the wells (containing a Dulbecco's modified Eagle's medium (DMEM) with 10% fetal bovine serum (FBS)) of a 24-well plate such that the number of cells was $2.0 \times 10^5$ cells per well. After 24 hours, each of the oligonucleotides was added, together with 9 mM calcium chloride, to the well to give a final concentration of 200 nM, and the resultant mixture was incubated for 72 hours.

After the incubation, the cells were collected, and a total RNA was extracted using an RNA extraction kit (Total RNeasy mini Kit manufactured by Qiagen). A reverse transcription reaction using the total RNA as a template was performed using a reverse transcription reaction kit (Quantitect reverse transcriptase manufactured by Qiagen or Primescript RT manufactured by Takara Bio Inc.). Furthermore, PCR using a sample obtained through the reverse transcription reaction as a template was performed using a real-time PCR reaction kit (SYBR Green PCR kit manufactured by Qiagen or SYBR Premix EX TaqII manufactured by Takara Bio Inc.). A nucleic acid amplification reaction was performed using the following temperature cycles: 95°

C. for 5 minutes→[(95° C. for 5 seconds→60° C. for 5 seconds)×40 cycles]. In the real-time PCR, the mRNA level of the housekeeping gene human GAPDH or actin was simultaneously quantified, and the hnSR100 mRNA level relative to the GAPDH mRNA level (FIG. 1) or actin mRNA level (FIG. 2) was evaluated. The mRNA level when each of the antisense oligonucleotides or the oligonucleotide was added is indicated as a relative value or relative % with respect to the mRNA level, which is taken as 1 or 100%, in the control (cells to which the oligonucleotides were not added).

The following shows the used primer sets.
Primer set for detecting hnSR100
Set1-Fw: tgacaaagacttgacaccacc (SEQ ID No. 101)
Set1-Rv: acctgcgtcgcttgtgttt (SEQ ID No. 102)
Set2-Fw: ctcctcaccccagaacaagg (SEQ ID No. 103)
Set2-Rv: ggatgggaccaaactggact (SEQ ID No. 104)
Primer set for detecting human Gapdh
Set1-Fw: gagtcaacggatttggtcgt (SEQ ID No. 105)
Set1-Rv: gacaagcttcccgttctcag (SEQ ID No. 106)
Primer set for detecting human actin
Set1-Fw: ggccgtcttcccctccatcg (SEQ ID No. 107)
Set1-Rv: ccagttggtgacgatgccgtgc (SEQ ID No. 108)

Figure 2:
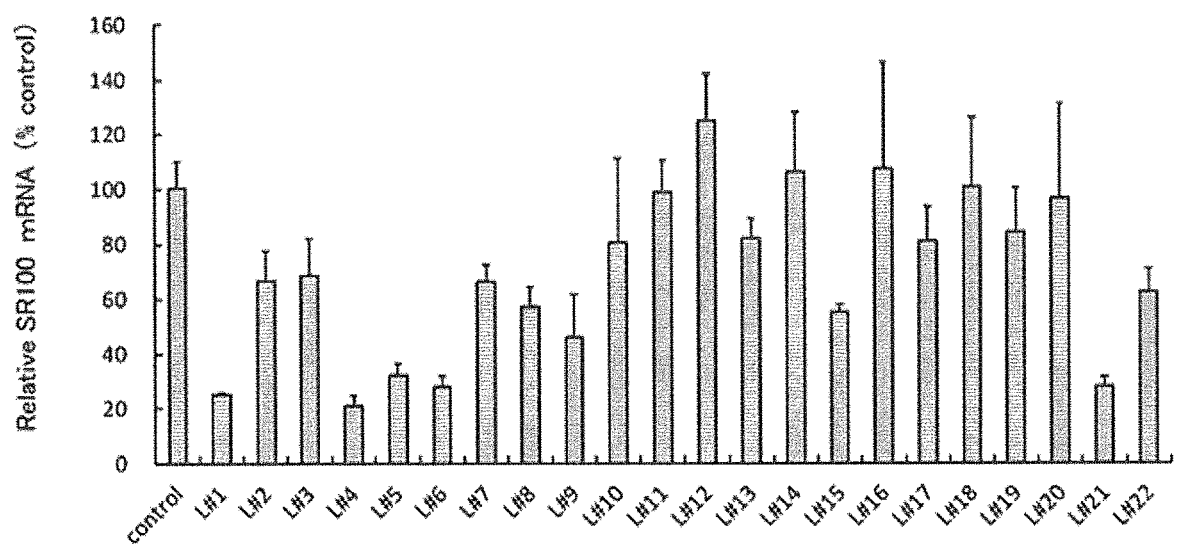
FIG. 2 is a graph illustrating hnSR100 mRNA levels in human SCLC cells (NCI-N417 cells) to which various antisense oligonucleotides have been added in vitro.

FIG. 1 (A: human NCI-H82 cells; and B: human STC-1 cells) and FIG. 2 (NCI-N417 cells) show the results. It was found that some antisense oligonucleotides reduced the mRNA level, that is, suppressed the mRNA expression, compared with the cases where the oligonucleotides had not been added to the cells ("control") and N26 had been added to the cells.

3-2: Dependence of Expression Suppression on Concentration of Antisense Oligonucleotide Regarding the antisense oligonucleotides of hnSR100 #1/hnSR100-712-LNA(15), hnSR100 #2/hnSR100-717-LNA(15), hnSR100L #3/hnSR100-721-LNA(15), hnSR100L #4/hnSR100-780-LNA(15), hnSR100L #5/hnSR100-783-LNA(15), hnSR100L #6/hnSR100-786-LNA(15), hnSR100L #21/hnSR100-7174-LNA(15), and hnSR100L #22/hnSR100-7177-LNA(15), which had been found to have a relatively high expression inhibiting activity (knockdown activity) in 3-1 above, the dependence of suppression of the nSR100 mRNA expression on the concentration of the antisense oligonucleotide was examined. The human NCI-H82 cells were used as the human SCLC cells, and the amount of the antisense oligonucleotide added to the human SCLC cells in 3-1 above was changed to any of 50 nM, 25 nM, and 12.5 nM.

Figure 3:
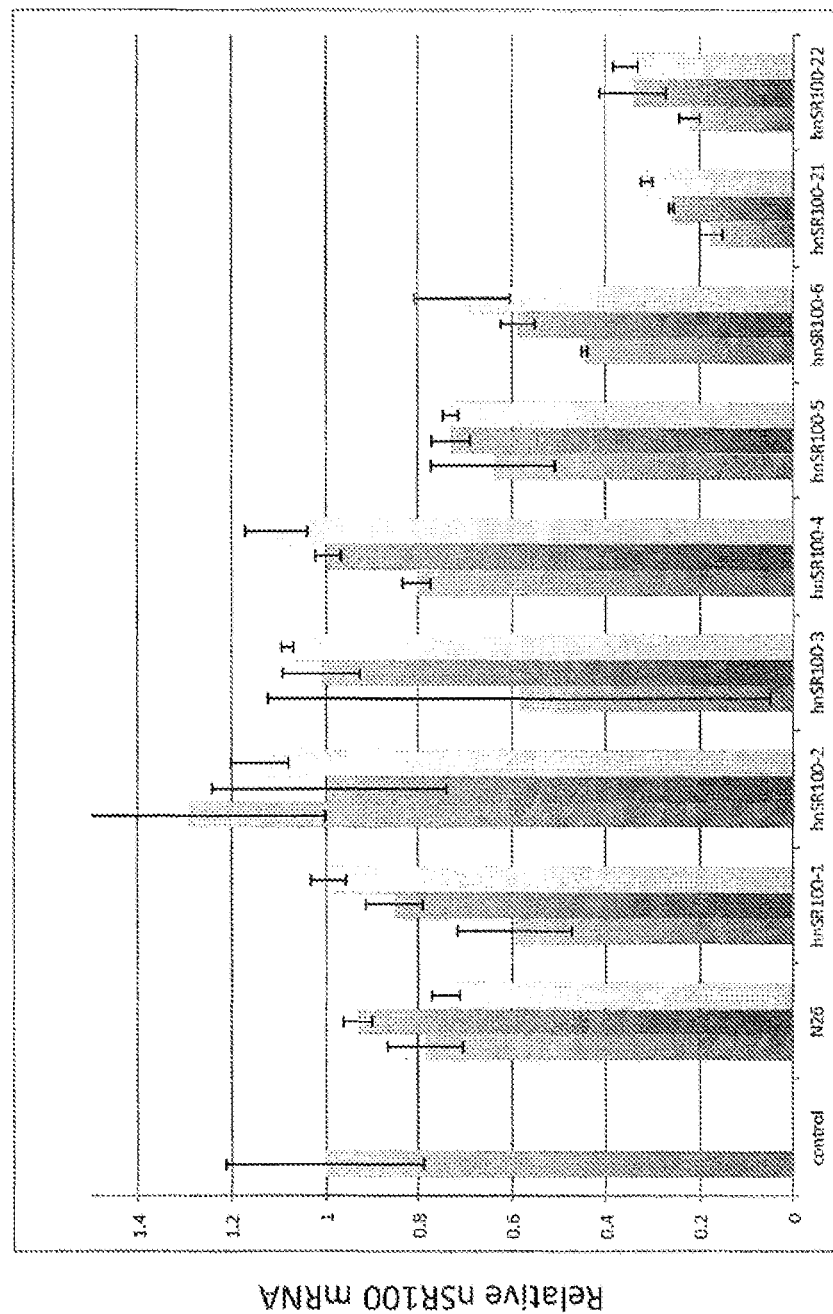
FIG. 3 is a graph illustrating nSR100 mRNA levels in human NCI-H82 cells to which hnSR100L #1 to #6, #21, and #22 have been added at various concentrations in vitro.

The results from each antisense oligonucleotide shown in FIG. 3 include the results for 50 nM, 25 nM, and 12.5 nM, which are arranged in this order from the left. It could be confirmed that the expression inhibiting activity (knockdown activity) was exhibited even when the antisense oligonucleotides were added in a low concentration. In particular, hnSR100L #6, hnSR100L #21, and hnSR100L #22 exhibited relatively high expression inhibiting activity even in the low-concentration condition.

Example 4: Suppression of nSR100 mRNA Expression in Human SCLC Cells In Vitro 4-1: Antisense Oligonucleotide Design In addition, antisense oligonucleotides that target the sequences including the target sequences of hnSR100L #6/hnSR100-786-LNA(15) and hnSR100L #21/hnSR100-7174-LNA(15), which exhibited relatively high expression inhibiting activity in the low-concentration condition in Example 3, and bases adjacent to the target sequences were designed (Tables 2 and 3).

In this example, each of the antisense oligonucleotides had a length of 15, 17, or 19 mer, and was provided with artificial nucleic acid regions containing sugar-modified nucleosides at the 5' end and the 3' end and a native nucleic acid region containing native nucleosides (DNAs) in the central portion. More specifically, a 3-9-2-1 gapmer, a 3-11-2-1 gapmer, and a 3-13-2-1 gapmer were designed in which three bases on the 5' end side (5' wing region) are sugar-modified nucleosides, subsequent nine to thirteen bases (gap region) are native nucleosides (DNAs), two bases close to the center in subsequent three bases on the 3' end side (A wing region) are sugar-modified nucleosides, and one base at the 3' end is a native nucleoside.

Tables 2 and 3 show the sequences of designed antisense oligonucleotides (in the direction from 5' toward 3') and the base positions in SEQ ID No. 1 corresponding to the 5' ends and the 3' ends of the sequences of the target regions of the antisense oligonucleotides. In the oligonucleotides shown in Table 2, a 2',-BNA/LNA was used as the sugar-modified nucleoside. In the oligonucleotides shown in Table 3, an AmNA was used as the sugar-modified nucleoside. All the oligonucleotides shown in Tables 2 and 3 are S-oligonucleotides.

TABLE 2

| Oligonucleotide Name | Antisense (5'→3') | Target Seq. 5'-end | Target Seq. 3'-end | SEQ. ID. No. |
|---|---|---|---|---|
| hnSR100-784-LNA(17) | T(L)^T(L)^T(L)^t^c^t^t^c^t^t^c^t^t^t^T(L)^T(L)^c | 784 | 800 | 109 |
| hnSR100-782-LNA(19) | T(L)^T(L)^T(L)^t^c^t^t^c^t^t^c^t^t^t^t^5(L)^T(L)^t | 782 | 800 | 110 |
| hnSR100-784-LNA(15) | T(L)^T(L)^5(L)^t^t^c^t^t^c^t^t^t^T(L)^T(L)^c | 784 | 798 | 111 |
| hnSR100-782-LNA(17) | T(L)^T(L)^5(L)^t^t^c^t^t^c^t^t^t^t^5(L)^T(L)^t | 782 | 798 | 112 |
| hnSR100-780-LNA(19) | T(L)^T(L)^5(L)^t^t^c^t^t^c^t^t^t^t^c^t^T(L)^G(L)^a | 780 | 798 | 113 |
| hnSR100-782-LNA(15) | 5(L)^T(L)^T(L)^c^t^t^c^t^t^t^t^t^5(L)^T(L)^t | 782 | 796 | 114 |
| hnSR100-780-LNA(17) | 5(L)^T(L)^T(L)^c^t^t^c^t^t^t^t^t^c^t^T(L)^G(L)^a | 780 | 796 | 115 |
| hnSR100-778-LNA(19) | 5(L)^T(L)^T(L)^c^t^t^c^t^t^t^t^t^c^t^t^g^A(L)^5(L)^a | 778 | 796 | 116 |

TABLE 2-continued

| Oligonucleotide Name | Antisense (5'→3') | Target Seq. 5'-end | Target Seq. 3'-end | SEQ. ID. No. |
|---|---|---|---|---|
| hnSR100-788-LNA(15) | A(L)^5(L)^T(L)^tttcttcttt^5(L)^T(L)^t | 788 | 802 | 117 |
| hnSR100-786-LNA(17) | A(L)^5(L)^T(L)^tttcttcttct^T(L)^T(L)^t | 786 | 802 | 118 |
| hnSR100-784-LNA(19) | A(L)^5(L)^T(L)^tttcttcttctttt^T(L)^T(L)^c | 784 | 802 | 119 |
| hnSR100-790-LNA(15) | G(L)^A(L)^A(L)^cttttcttc^T(L)^T(L)^c | 790 | 804 | 120 |
| hnSR100-788-LNA(17) | G(L)^A(L)^A(L)^cttttcttctt^5(L)^T(L)^t | 788 | 804 | 121 |
| hnSR100-786-LNA(19) | G(L)^A(L)^A(L)^cttttcttcttct^T(L)^T(L)^t | 786 | 804 | 122 |
| hnSR100-7172-LNA(17) | T(L)^T(L)^G(L)^tgtgactgaag^5(L)^5(L)^t | 7172 | 7188 | 123 |
| hnSR100-7170-LNA(19) | T(L)^T(L)^G(L)^tgtgactgaagcc^T(L)^5(L)^c | 7170 | 7188 | 124 |
| hnSR100-7172-LNA(15) | G(L)^T(L)^G(L)^tgactgaag^5(L)^5(L)^t | 7172 | 7186 | 125 |
| hnSR100-7170-LNA(17) | G(L)^T(L)^G(L)^tgactgaagcc^T(L)^5(L)^c | 7170 | 7186 | 126 |
| hnSR100-7168-LNA(19) | G(L)^T(L)^G(L)^tgactgaagcctc^5(L)^A(L)^t | 7168 | 7186 | 127 |
| hnSR100-7170-LNA(15) | G(L)^T(L)^G(L)^actgaagcc^T(L)^5(L)^c | 7170 | 7184 | 128 |
| hnSR100-7168-LNA(17) | G(L)^T(L)^G(L)^actgaagcctc^5(L)^A(L)^t | 7168 | 7184 | 129 |
| hnSR100-7166-LNA(19) | G(L)^T(L)^G(L)^actgaagctcca^T(L)^T(L)^t | 7166 | 7184 | 130 |
| hnSR100-7176-LNA(15) | A(L)^T(L)^T(L)^tgtgtgact^G(L)^A(L)^a | 7176 | 7190 | 131 |
| hnSR100-7174-LNA(17) | A(L)^T(L)^T(L)^tgtggactgaA(L)^G(L)^c | 7174 | 7190 | 132 |
| hnSR100-7172-LNA(19) | A(L)^T(L)^T(L)^tgtgtgactgaag^5(L)^5(L)^t | 7172 | 7190 | 133 |
| hnSR100-7178-LNA(15) | T(L)^A(L)^A(L)^tttgtgtga^5(L)^T(L)^g | 7178 | 7192 | 134 |
| hnSR100-7176-LNA(17) | T(L)^A(L)^A(L)^tttgtgtgact^G(L)^A(L)^a | 7176 | 7192 | 135 |
| hnSR100-7174-LNA(19) | T(L)^A(L)^A(L)^tttgtgtgactgaA(L)^G(L)^c | 7174 | 7192 | 136 |

"5" represents 5-methylcytosine(5mC).
A(L), G(L), 5(L) and T(L) represent 2',4'-BNA/LNA-type bases.
a, g, c and t represent DNA-type bases.
"^" represents a phosphorothioated site.

The base sequences of the antisense oligonucleotides shown in Table 2 correspond to SEQ ID. Nos. 109 to 136 in the order from top to bottom.

TABLE 3

| Oligonucleotide Name | Antisense (5'→3') | Target Seq. 5'-end | Target Seq. 3'-end | SEQ. ID. No. |
|---|---|---|---|---|
| hnSR100-786-AmNA(15) | T(Y)^T(Y)^T(Y)^tcttcttct^T(Y)^T(Y)^t | 786 | 800 | 137 |
| hnSR100-784-AmNA(17) | T(Y)^T(Y)^T(Y)^tcttcttctttt^T(Y)^T(Y)^c | 784 | 800 | 138 |
| hnSR100-782-AmNA(19) | T(Y)^T(Y)^T(Y)^tcttcttcttttt^5(Y)^T(Y)^t | 782 | 800 | 139 |
| hnSR100-784-AmNA(15) | T(Y)^T(Y)^5(Y)^ttcttctttt^T(Y)^T(Y)^c | 784 | 798 | 140 |
| hnSR100-782-AmNA(17) | T(Y)^T(Y)^5(Y)^ttcttcttttt^5(Y)^T(Y)^t | 782 | 798 | 141 |
| hnSR100-780-AmNA(19) | T(Y)^T(Y)^5(Y)^ttcttcttttttct^T(Y)^G(Y)^a | 780 | 798 | 142 |

TABLE 3-continued

| Oligonucleotide Name | Antisense (5'→3') | Target Seq. 5'-end | Target Seq. 3'-end | SEQ. ID. No. |
|---|---|---|---|---|
| hnSR100-782-AmNA(15) | 5(Y)^T(Y)^T(Y)^cttctttttt5(Y)^T(Y)^t | 782 | 796 | 143 |
| hnSR100-780-AmNA(17) | 5(Y)^T(Y)^T(Y)^cttctttttctT(Y)^G(Y)^a | 780 | 796 | 144 |
| hnSR100-778-AmNA(19) | 5(Y)^T(Y)^T(Y)^cttctttttcttgA(Y)^5(Y)^a | 778 | 796 | 145 |
| hnSR100-788-AmNA(15) | A(Y)^5(Y)^T(Y)^tttcttctt5(Y)^T(Y)^t | 788 | 802 | 146 |
| hnSR100-786-AmNA(17) | A(Y)^5(Y)^T(Y)^tttcttcttctT(Y)^T(Y)^t | 786 | 802 | 147 |
| hnSR100-784-AmNA(19) | A(Y)^5(Y)^T(Y)^tttcttcttctttT(Y)^T(Y)^c | 784 | 802 | 148 |
| hnSR100-790-AmNA(15) | G(Y)^A(Y)^A(Y)^cttttcttcT(Y)^T(Y)^c | 790 | 804 | 149 |
| hnSR100-788-AmNA(17) | G(Y)^A(Y)^A(Y)^cttttcttctt5(Y)^T(Y)^t | 788 | 804 | 150 |
| hnSR100-786-AmNA(19) | G(Y)^A(Y)^A(Y)^cttttcttcttctT(Y)^T(Y)^t | 786 | 804 | 151 |
| hnSR100-7174-AmNA(15) | T(Y)^T(Y)^G(Y)^tgtgactgaA(Y)^G(Y)^c | 7174 | 7188 | 152 |
| hnSR100-7172-AmNA(17) | T(Y)^T(Y)^G(Y)^tgtgactgaag5(Y)^5(Y)^t | 7172 | 7188 | 153 |
| hnSR100-7170-AmNA(19) | T(Y)^T(Y)^G(Y)^tgtgactgaagccT(Y)^5(Y)^c | 7170 | 7188 | 154 |
| hnSR100-7172-AmNA(15) | G(Y)^T(Y)^G(Y)^tgactgaag5(Y)^5(Y)^t | 7172 | 7186 | 155 |
| hnSR100-7170-AmNA(17) | G(Y)^T(Y)^G(Y)^tgactgaagccT(Y)^5(Y)^c | 7170 | 7186 | 156 |
| hnSR100-7168-AmNA(19) | G(Y)^T(Y)^G(Y)^tgactgaagcctc5(Y)^A(Y)^t | 7168 | 7186 | 157 |
| hnSR100-7170-AmNA(15) | G(Y)^T(Y)^G(Y)^actgaagccT(Y)^5(Y)^c | 7170 | 7184 | 158 |
| hnSR100-7168-AmNA(17) | G(Y)^T(Y)^G(Y)^actgaagcctc5(Y)^A(Y)^t | 7168 | 7184 | 159 |
| hnSR100-7166-AmNA(19) | G(Y)^T(Y)^G(Y)^actgaagcctccaT(Y)^T(Y)^t | 7166 | 7184 | 160 |
| hnSR100-7176-AmNA(15) | A(Y)^T(Y)^T(Y)^tgtgtgactG(Y)^A(Y)^a | 7176 | 7190 | 161 |
| hnSR100-7174-AmNA(17) | A(Y)^T(Y)^T(Y)^tgtgtgactgaA(Y)^G(Y)^c | 7174 | 7190 | 162 |
| hnSR100-7172-AmNA(19) | A(Y)^T(Y)^T(Y)^tgtgtgactgaag5(Y)^5(Y)^t | 7172 | 7190 | 163 |
| hnSR100-7178-AmNA(15) | T(Y)^A(Y)^A(Y)^tttgtgtga5(Y)^T(Y)^g | 7178 | 7192 | 164 |
| hnSR100-7176-AmNA(17) | T(Y)^A(Y)^A(Y)^tttgtgtgactG(Y)^A(Y)^a | 7176 | 7192 | 165 |
| hnSR100-7174-AmNA(19) | T(Y)^A(Y)^A(Y)^tttgtgtgactgaA(Y)^G(Y)^c | 7174 | 7192 | 166 |

"5" represents 5-methylcytosine(5mC).
A(Y), G(Y), 5(Y) and T(Y) represent bases of AmNA.
a, g, c and t represent bases of DNA.
"^" represents a phosphorothioation.

The base sequences of the antisense oligonucleotides shown in Table 3 correspond to SEQ ID. Nos. 137 to 166 in the order from top to bottom.

The description of hnSR100-p-n(L) in Table 1, which represents an antisense oligonucleotide, also applies to hnSR100-p-n(L) in Tables 2 and 3. "n" represents a sugar-modified nucleoside (artificial nucleic acid) LNA in Table 2 and a sugar-modified nucleoside (artificial nucleic acid) AmNA in Table 3. For example, in the case of hnSR100-7174-AmNA(15), position 7174 of the base sequence of SEQ ID No. 1 corresponds to the 5' end of the target region, an AmNA is contained, and the length is 15 mer.

As in Example 2, the sequence of each antisense oligonucleotide was designed as a base sequence complementary to a base sequence obtained by adding bases to the target region in the direction from the 5' end toward the 3' end based on the base sequence of SEQ ID No. 1 until the length of the antisense oligonucleotide was obtained.

4-2: Assay of Suppression of nSR100 mRNA Expression In Vitro

As in 3-1 above, the human STC-1 cells were used as the human SCLC cells in an amount of $1 \times 10^5$ cells/well, and each of the various antisense oligonucleotides was added to the human SCLC cells, and then the nSR100 mRNA level was determined. For comparison, as in 3-1 above, an N26 oligonucleotide (base sequence: 5'-TGAacaaaataaTAc-3'; in this example, a base represented by an uppercase letter is a 2',4'-BNA/LNA, a base represented by a lowercase letter is a DNA, and this oligonucleotide is an S-oligonucleotide; SEQ ID No. 100) was used.

Figure 4:
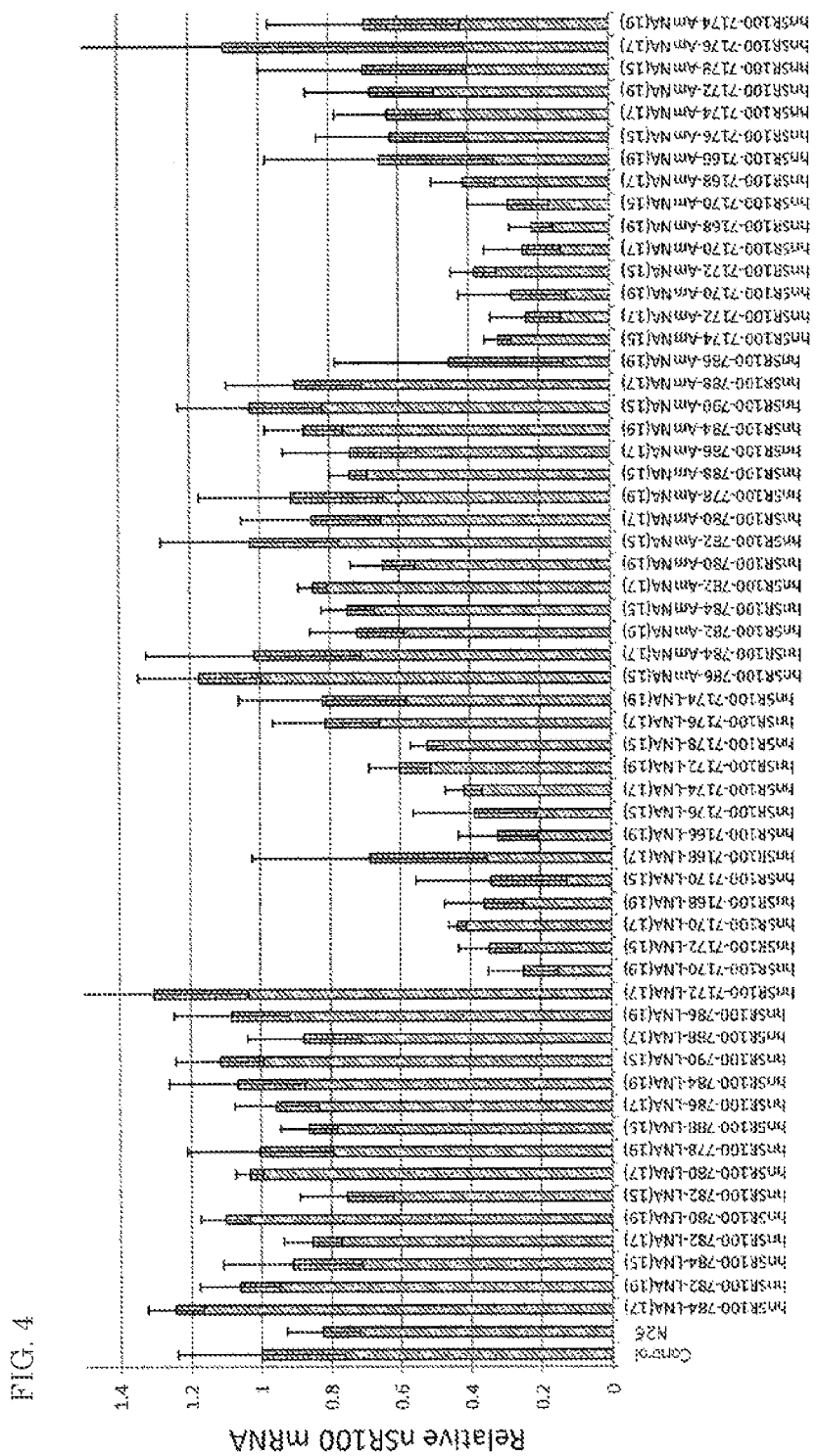
FIG. 4 is a graph illustrating nSR100 mRNA levels in human STC-1 cells to which various antisense oligonucleotides having base sequences designed based on hnSR100L #6 and #21 have been added in vitro.

FIG. 4 shows the results. It was found that, in both the case where an LNA was contained and the case where an AmNA was contained, some antisense oligonucleotides reduced the nSR100 mRNA level, that is, suppressed the mRNA expression, compared with the cases where the oligonucleotides had not been added to the cells ("control") and N26 had been added to the cells ("N26"). It was confirmed that the antisense oligonucleotides having the base sequences designed based on hnSR100L #21/hnSR100-7174-LNA(15) exhibited relatively high mRNA expression inhibiting activity.

4-3: Assay of Suppression of nSR100 mRNA Expression In Vitro by Antisense Oligonucleotide Having Base Sequence Designed Based on hnSR100L #21

Furthermore, the antisense oligonucleotides having base sequences designed based on hnSR100L #21/hnSR100-7174-LNA(15) were transfected into the human SCLC cells using a transfection reagent, and the mRNA expression inhibiting activity thereof was examined.

The human STC-1 cells in a logarithmic growth phase were seeded in the wells (containing a DMEM medium (low glucose) with 10% FBS) of a 24-well plate such that the number of cells was $1.0 \times 10^5$ cells per well. After 24 hours, each of the oligonucleotides was added, together with 9 mM calcium chloride, to the well to give a final concentration of 100 nM or 30 nM, and transfection was performed using a commercially available transfection reagent (Lipofectamine 3000: available from Thermo Fisher Scientific). The cells were further cultured, and were collected after 48 hours. The hnSR100 mRNA level was evaluated in the same manner as in 3-1 above.

Figure 5:
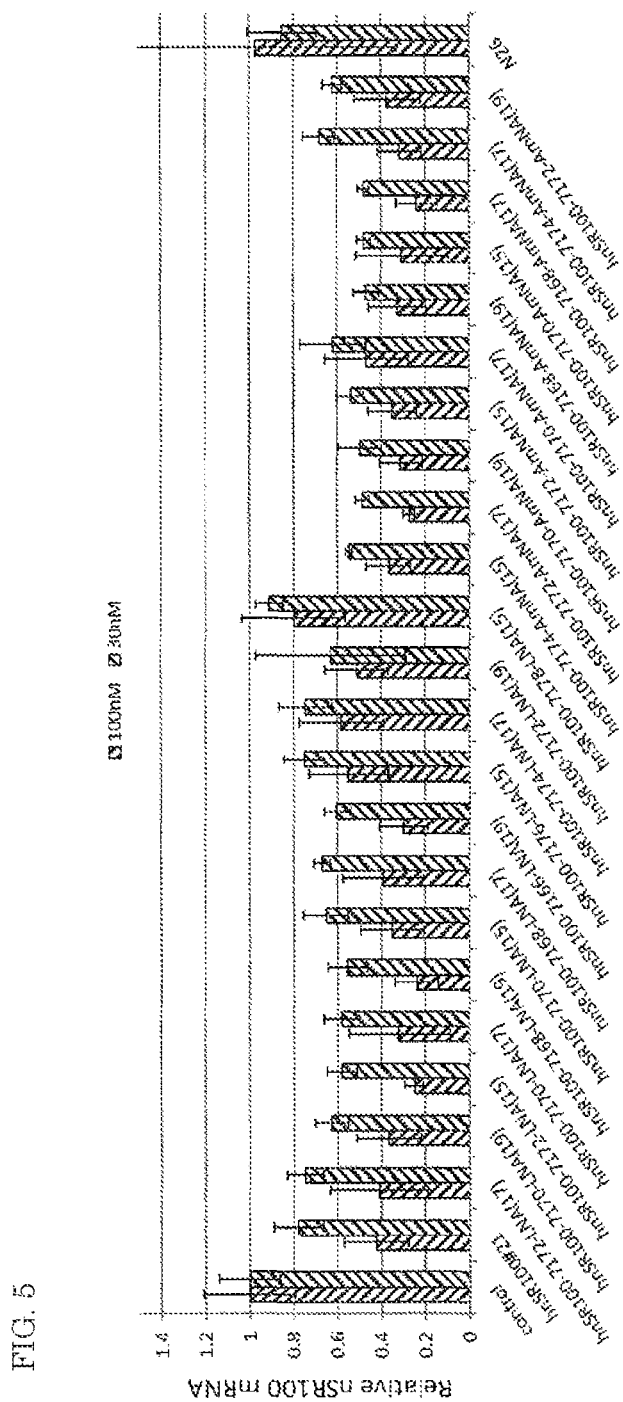
FIG. 5 is a graph illustrating nSR100 mRNA levels in human STC-1 cells to which various antisense oligonucleotides having base sequences designed based on hnSR100L #21/hnSR100-7174-LNA(15) have been added in vitro.

FIG. 5 shows the results. It was found that, in both the case where an LNA was contained and the case where an AmNA was contained, some antisense oligonucleotides reduced the mRNA level, that is, suppressed the mRNA expression, compared with the cases where the oligonucleotides had not been added to the cells (control) and N26 had been added to the cells ("N26").

4-5: Dependence of Suppression of mRNA Expression on Concentration of Antisense Oligonucleotide Regarding suppression of mRNA expression, the dependence of suppression of the nSR100 mRNA expression on the concentrations of the antisense oligonucleotides of hnSR100-7172-LNA(15), hnSR100-7170-LNA(17), hnSR100-7168-LNA(19), hnSR100-7172-AmNA(17), hnSR100-7170-AmNA(15), and hnSR100-7168-AmNA (17) was examined. The mRNA level was evaluated as described in 4-3 above, except that the amount of the antisense oligonucleotide added for transfection into the human STC-1 cells was changed to any of 200 nM, 100 nM, 30 nM, and 15 nM.

Figure 6:
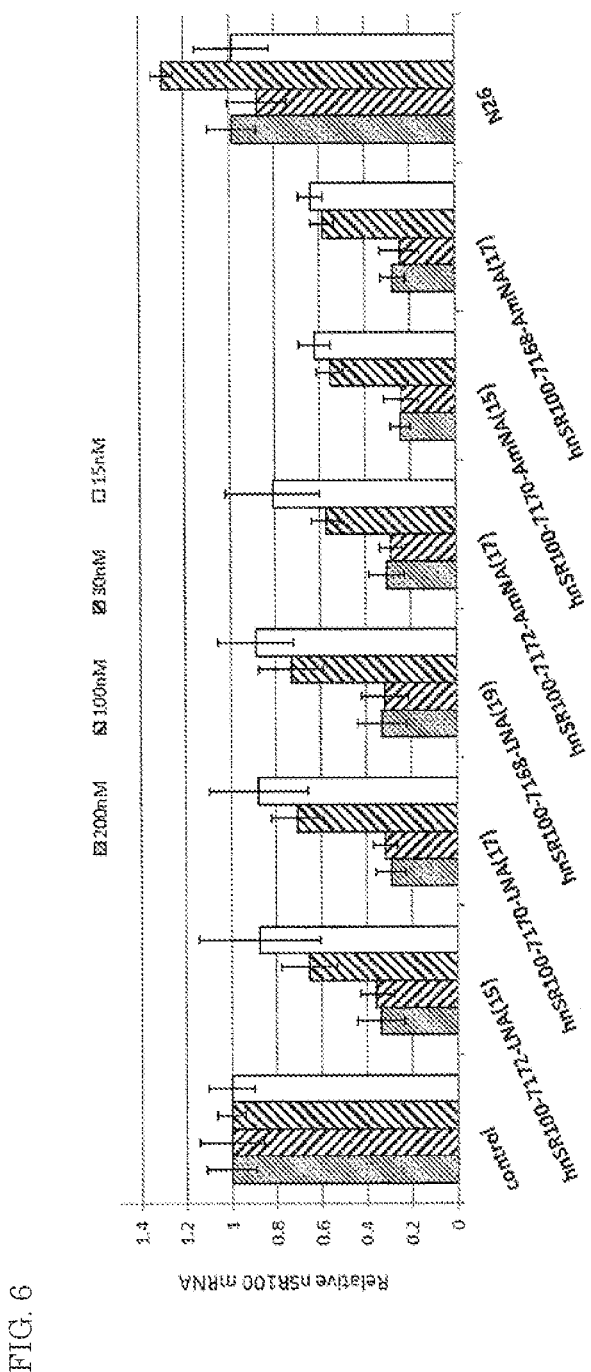
FIG. 6 is a graph illustrating nSR100 mRNA levels in human STC-1 cells to which hnSR100-7172-LNA(15), hnSR100-7170-LNA(17), hnSR100-7168-LNA(19), hnSR100-7172-AmNA(17), hnSR100-7170-AmNA(15), and hnSR100-7168-AmNA(17) have been added at various concentrations in vitro.

FIG. 6 shows the results. It was confirmed that the suppression of expression (knockdown) had a dependence on the concentrations of the used antisense oligonucleotides, and the suppression of expression (knockdown) was observed even when the antisense oligonucleotides were added at a low concentration (e.g., 15 nM or 30 nM).

4-6: Assay of Suppression of nSR100 mRNA Expression In Vitro

The nSR100 mRNA level was evaluated as described in 3-1 above using the human NCI-H82 cells to which the various antisense oligonucleotides used in 4-5 above had been added.

Figure 7:
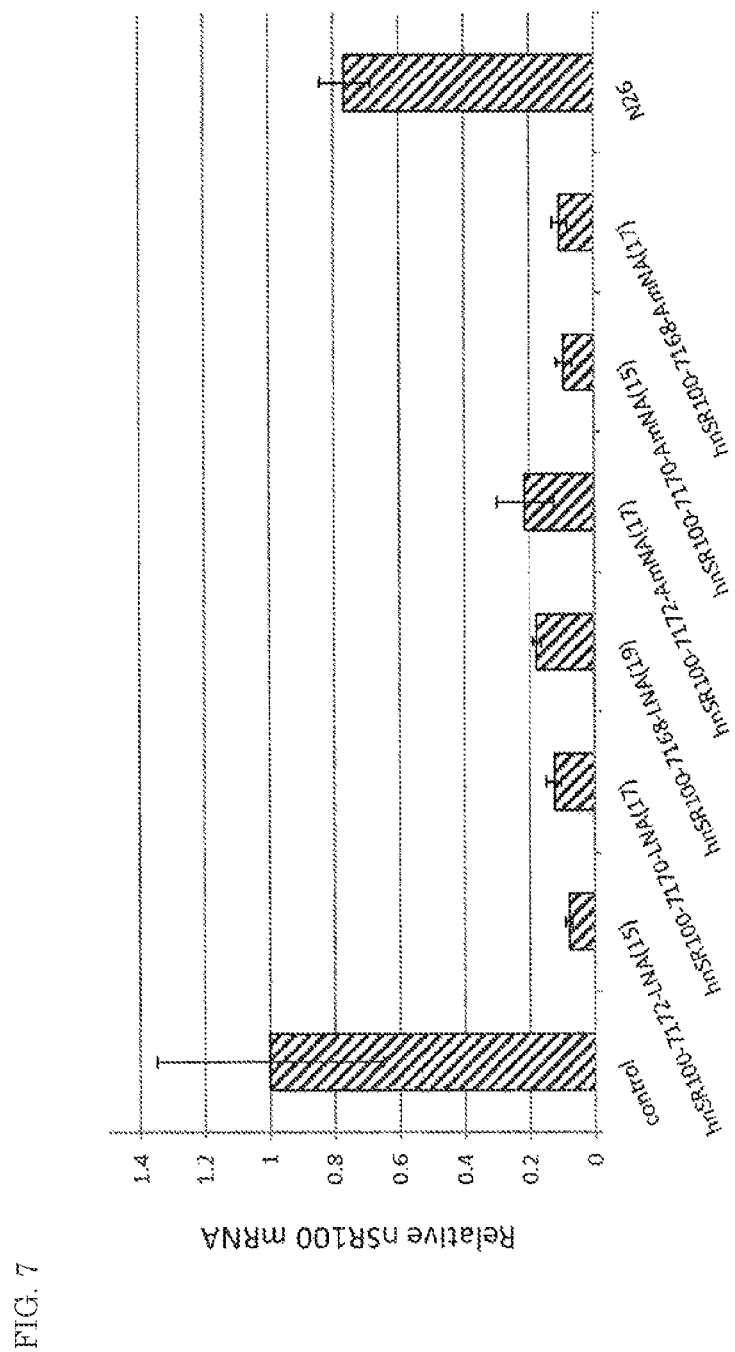
FIG. 7 is a graph illustrating nSR100 mRNA levels in human NCI-H82 cells to which hnSR100-7172-LNA(15), hnSR100-7170-LNA(17), hnSR100-7168-LNA(19), hnSR100-7172-AmNA(17), hnSR100-7170-AmNA(15), and hnSR100-7168-AmNA(17) have been added in vitro.

FIG. 7 shows the results. It was confirmed that all of hnSR100-7172-LNA(15), hnSR100-7170-LNA(17), hnSR100-7168-LNA(19), hnSR100-7172-AmNA(17), hnSR100-7170-AmNA(15), and hnSR100-7168-AmNA (17) also suppressed the nSR100 mRNA expression in the human NCI-H82 cells.

Example 5: Examination of Cell Growth Inhibiting Effect of Antisense Oligonucleotide In Vitro The NCI-82 cells were used as the human SCLC cells, and the mRNA level in the case where the antisense oligonucleotide of hnSR100L #21 was used was determined in the same manner as in 3-1 above. In addition, the human STC-1 cells were used as the human SCLC cells, and the mRNA level was evaluated as described in 4-3 above (N26 was used for comparison).

Furthermore, the cell growth capacity of the cells to which the antisense oligonucleotide of hnSR100L #21/hnSR100-7174-LNA(15) or N26 had been added or the cells to which the oligonucleotides had not been added was examined using a WST-1 reagent kit (available from Dojindo Laboratories) in accordance with the instruction included in the kit. The results of the cell growth capacity were indicated as a relative number with respect to the number of viable cells, which was taken as 1, in the cells to which the antisense oligonucleotides had not been added (control).

Figure 8:
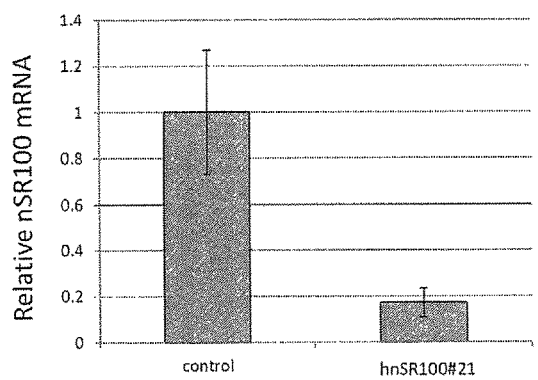
FIG. 8 shows graphs illustrating nSR100 mRNA levels ("(a)") and relative cell viability ("(b)") in human NCI-H82 cells ("A.") and human STC-1 cells ("B.") to which hnSR100L #21 has been added.
Figure 8:
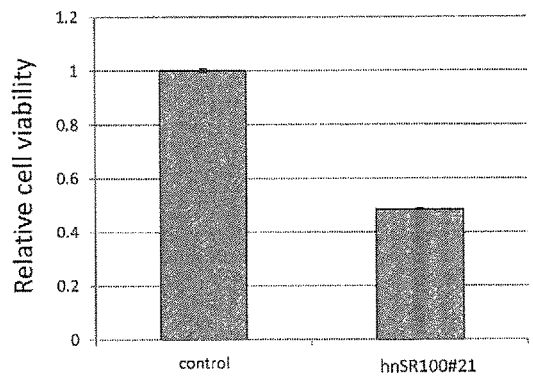
Figure 8:
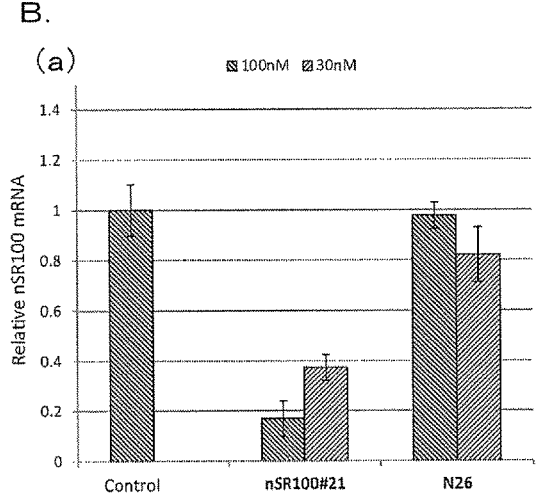
Figure 8:
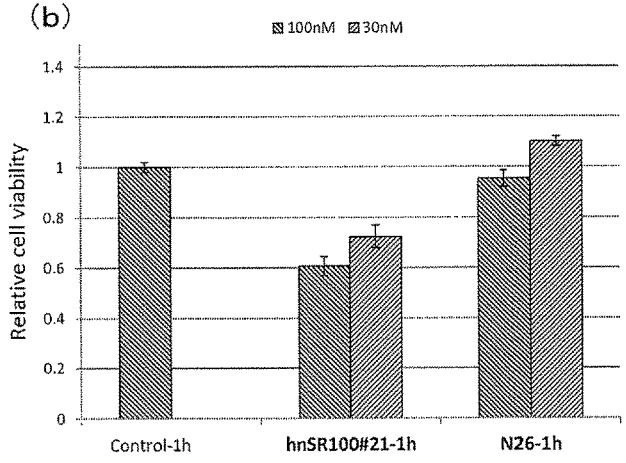

FIG. 8 shows the results (A: human NCI-H82 cells, and B: human STC-1 cell; and (a): nSR100 mRNA level, and (b) cell viability). It was observed that the hnR100 mRNA level and the cell viability decreased in the human NCI-H82 cells to which the antisense oligonucleotide of hnSR100L #21 had been added compared with the human NCI-H82 cells to which the oligonucleotides had not been added (control). It was confirmed that the hnR100 mRNA level and the cell viability decreased in the human STC-1 cells compared with the human STC-1 cells to which the oligonucleotides had not been added (control) and the human STC-1 cells to which N26, which was used for comparison, was added. It is confirmed from these results that, due to the addition of the antisense oligonucleotide of hnSR100L #21, the hnR100 mRNA expression is suppressed in the human SCLC cells, and in addition, the cell viability of the SCLC cells is reduced, or the cell growth of the SCLC cells is suppressed.

Example 6: Examination of Tumor Suppressing Effect in Antisense Oligonucleotide Administered Mouse 6-1. Preparation of Cells for Transplantation and Antisense Oligonucleotide for Administration In order to enable the observation of tumor formation using fluorescence images, firefly luciferase and green fluorescence protein (GFP) were introduced into human NCI-N417 cells using a retrovirus, the transduced cells ("hSCLC-LUC cells") were isolated, and adherent culture of these cells was performed on a culture plate coated with an extracellular matrix component (Millipore, ECL cell attachment matrix), at 37° C. for 48 hours in a humidified environment in the presence of 5% $CO_2$.

6-2. Tumor Formation by Intrathoracic Transplantation, and Intravenous Administration of Antisense Oligonucleotide hSCLC-LUC cells ($1 \times 10^6$ cells) were intrathoracically transplanted into a six-week-old BALB/c Slc-nu/nu athymic nude mouse (male) to form a tumor. Administration of an antisense oligonucleotide was started 7 days after the transplantation. The day on which the administration was started was taken as day 0, and the antisense oligonucleotide was intravenously administered to the mouse in an amount of 2 mg/kg on day 0, day 2, day 4, and day 6. The antisense oligonucleotides of hnSR100-7168-AmNA(17), hnSR100-7172-AmNA(17), and hnSR100-7174-AmNA(15) were used in this experiment. An L26 oligonucleotide containing an AmNA (base sequence: 5'-TGAacaaaataaTAc-3'; a base represented by an uppercase letter is an AmNA, a base represented by a lowercase letter is a DNA, and this oligonucleotide is an S-oligonucleotide; SEQ ID No. 167; this oligonucleotide corresponds to the base sequence of the N26 oligonucleotide, except that an AmNA is used as a modified nucleic acid) was used as a control oligonucleotide in the same manner. On each administration day, a tumor of the mouse was observed.

6-3. Tumor Formation by Intrathoracic Transplantation, and Airway Administration of Antisense Oligonucleotide hSCLC-LUC cells (1×10$^6$ cells) were intrathoracically transplanted into a six-week-old BALB/c Slc-nu/nu athymic nude mouse (male) to form a tumor. Administration of an antisense oligonucleotide was started 3 days after the transplantation. The day on which the administration was started was taken as day 0, and the antisense oligonucleotide was administered to the airway of the mouse in an amount of 50 mg/kg on day 0, day 2, day 4, and day 6. The antisense oligonucleotide of hnSR100L #21/hnSR100-7174-LNA(15) was used in this experiment. An L26 oligonucleotide containing an LNA (base sequence: 5'-TGAacaaaataaTAc-3'; a base represented by an uppercase letter is a 2',4'-BNA/LNA, a base represented by a lowercase letter is a DNA, and this oligonucleotide is an S-oligonucleotide; SEQ ID No. 100; this oligonucleotide corresponds to the N26 oligonucleotide) was used as a control oligonucleotide in the same manner. On day 0, day 7, and day 10 after the administration was started, a tumor of the mouse was observed.

6-4. Tumor Formation by Subcutaneous Transplantation into Back, and Intraabdominal Administration of Antisense Oligonucleotide hSCLC-LUC cells (5×10$^5$ cells) were subcutaneously transplanted into a six-week-old BALB/c Slc-nu/nu athymic nude mouse (female) to form a tumor. An antisense oligonucleotide was intrabdominally administered to the mouse 7 days after the transplantation. The antisense oligonucleotides of hnSR100L #1/hnSR100-712-LNA(15), hnSR100L #4/hnSR100-780-LNA(15), and hnSR100L #21/hnSR100-7174-LNA(15) were used in this experiment. An L26 oligonucleotide containing an LNA (base sequence: 5'-TGAacaaaataaTAc-3'; a base represented by an uppercase letter is a 2',4'-BNA/LNA, a base represented by a lowercase letter is a DNA, and this oligonucleotide is an S-oligonucleotide; SEQ ID No. 100; this oligonucleotide corresponds to the N26 oligonucleotide) was used as a control oligonucleotide in the same manner. A tumor of the mouse was observed 10 days after the administration of the antisense oligonucleotide.

6-5. Results

Figure 9:
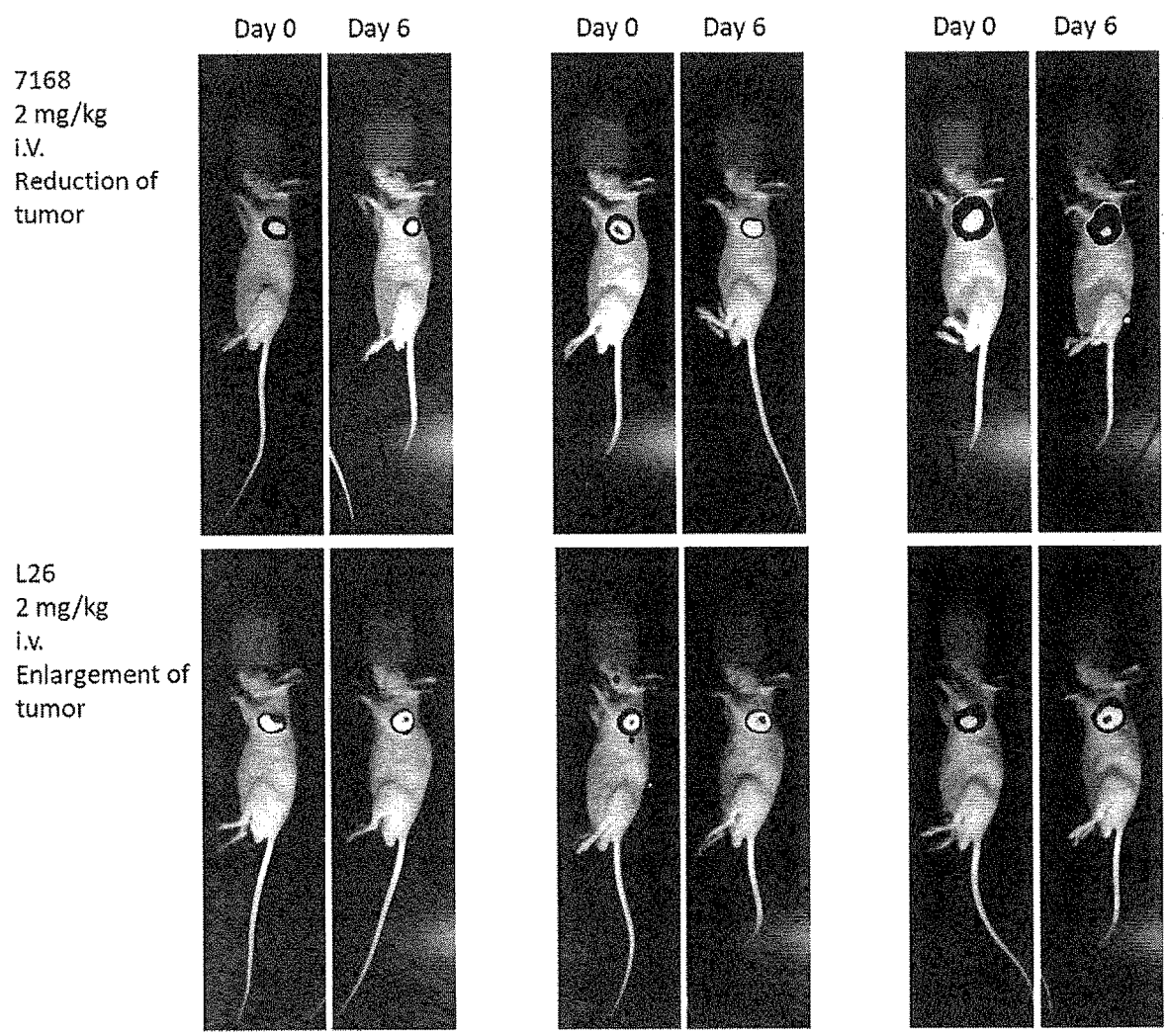
FIG. 9 shows fluorescence images illustrating changes in a tumor state due to intravenous administration of hnSR100-7168-AmNA(17) in mice (n=3) into which hSCLC-LUC cells have been intrathoracically transplanted.
Figure 10:
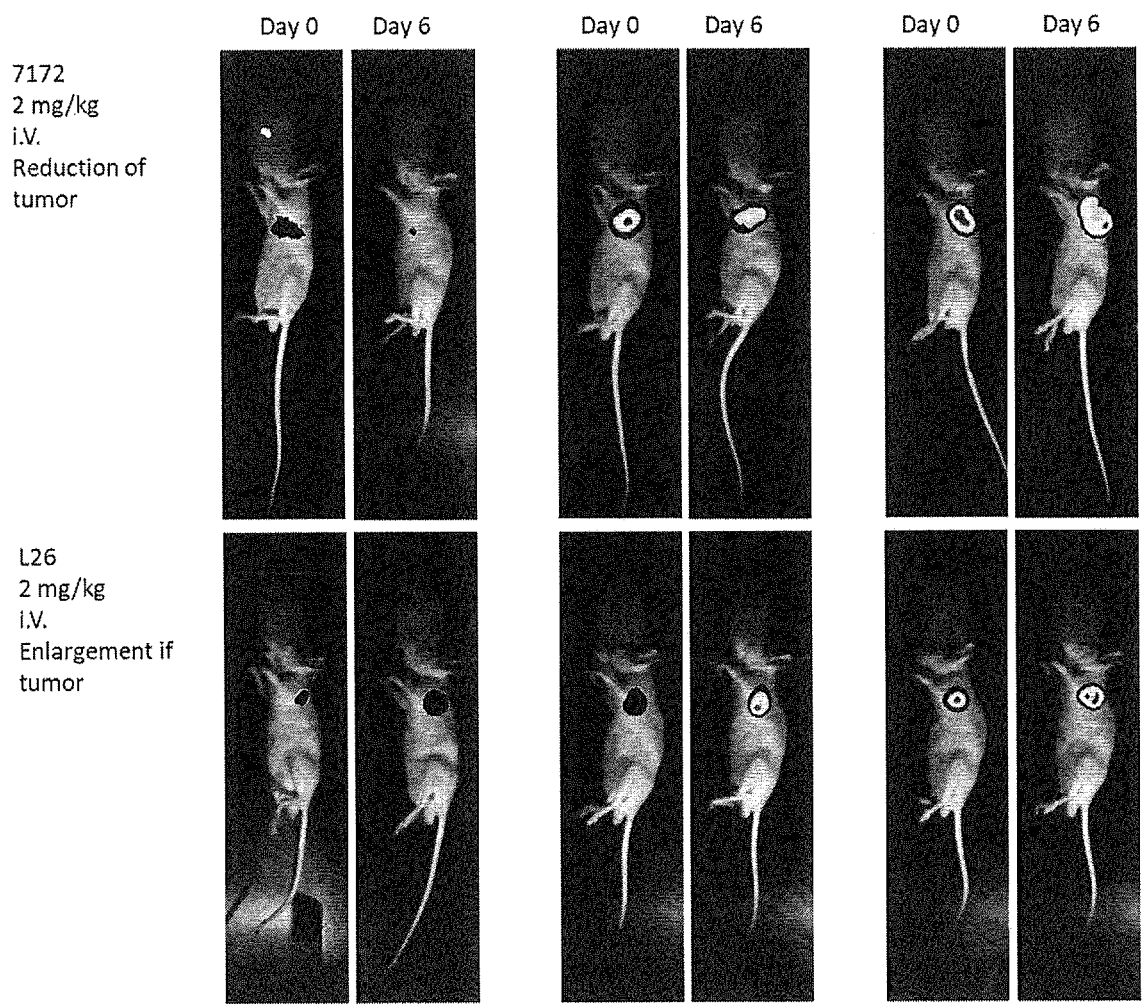
FIG. 10 shows fluorescence images illustrating changes in a tumor state due to intravenous administration of hnSR100-7172-AmNA(17) in mice (n=3) into which hSCLC-LUC cells have been intrathoracically transplanted.
Figure 11:
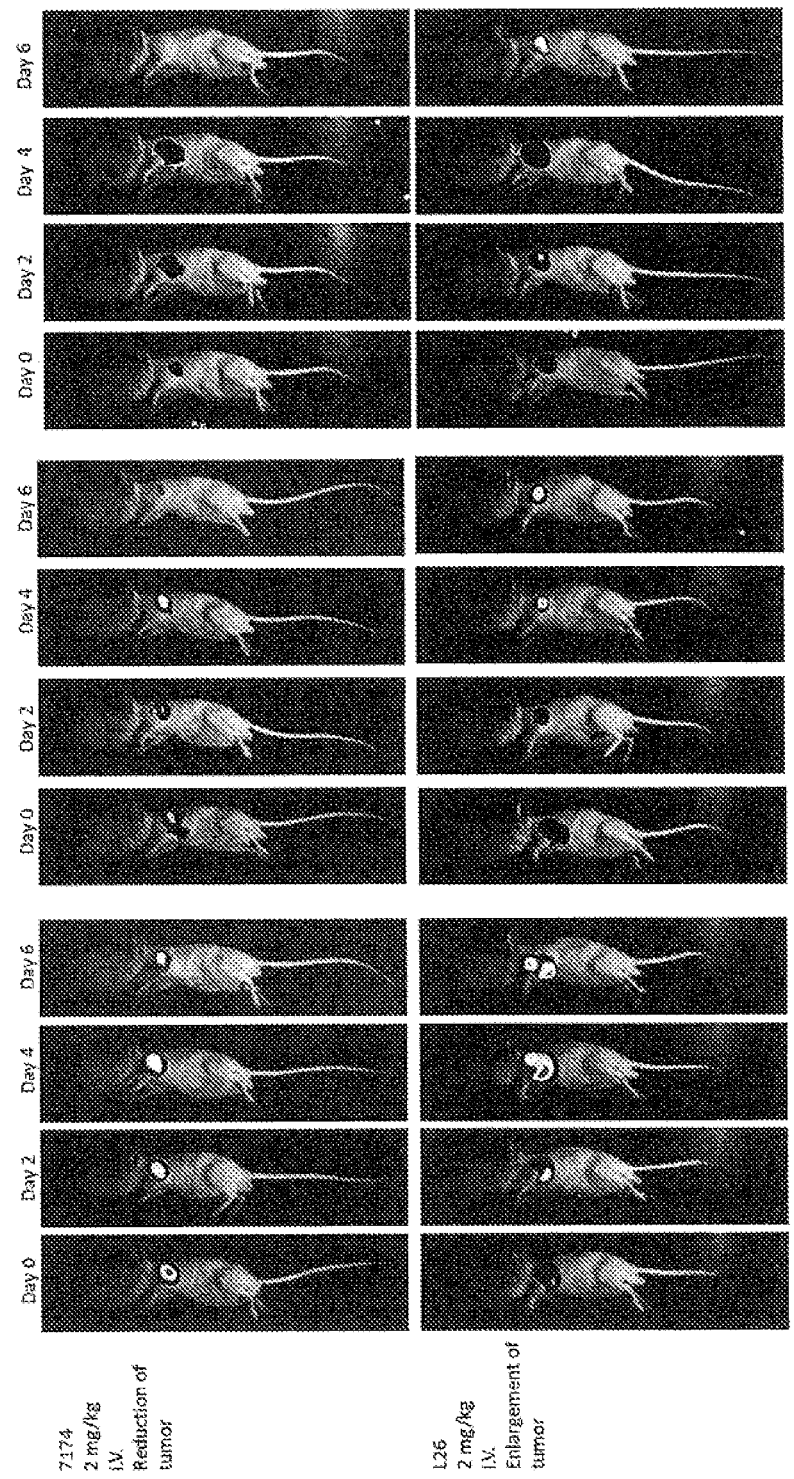
FIG. 11 shows fluorescence images illustrating changes in a tumor state due to intravenous administration of hnSR100-7174-AmNA(15) in mice (n=3) into which hSCLC-LUC cells have been intrathoracically transplanted.
Figure 12:
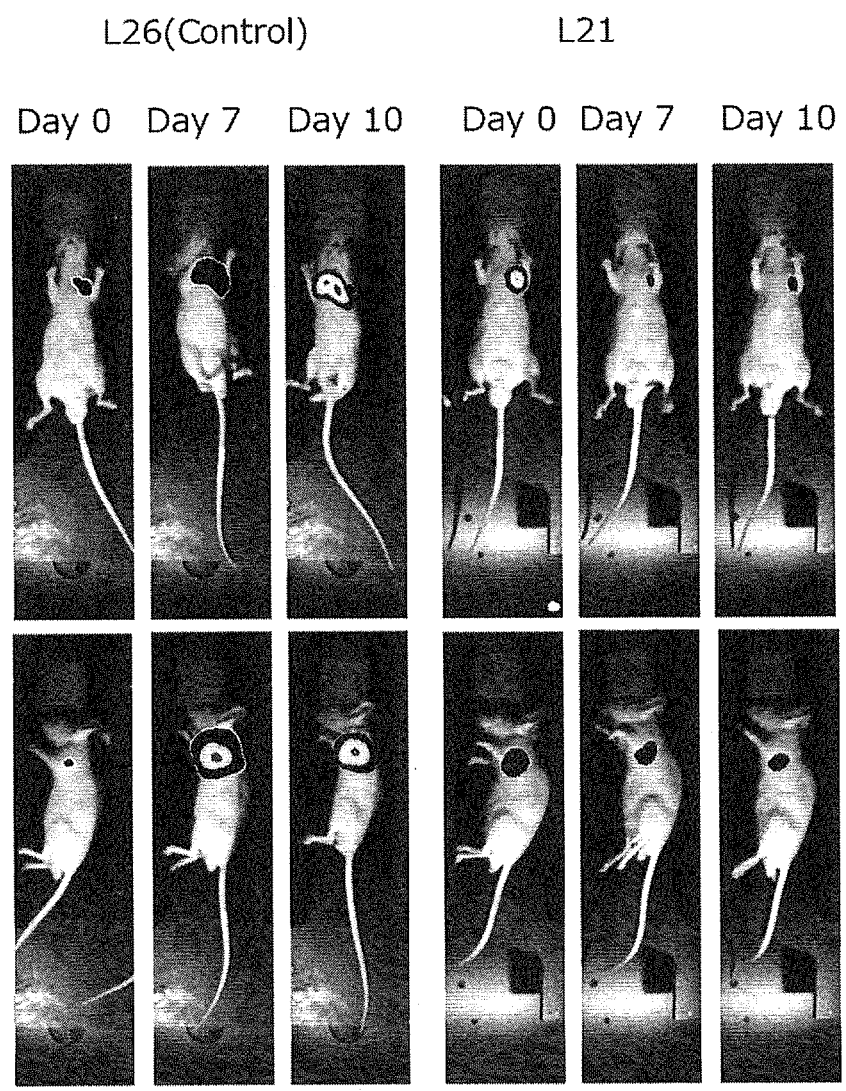
FIG. 12 shows fluorescence images illustrating changes in a tumor state due to airway administration of hnSR100L #21 in mice into which hSCLC-LUC cells have been intrathoracically transplanted.
Figure 13:
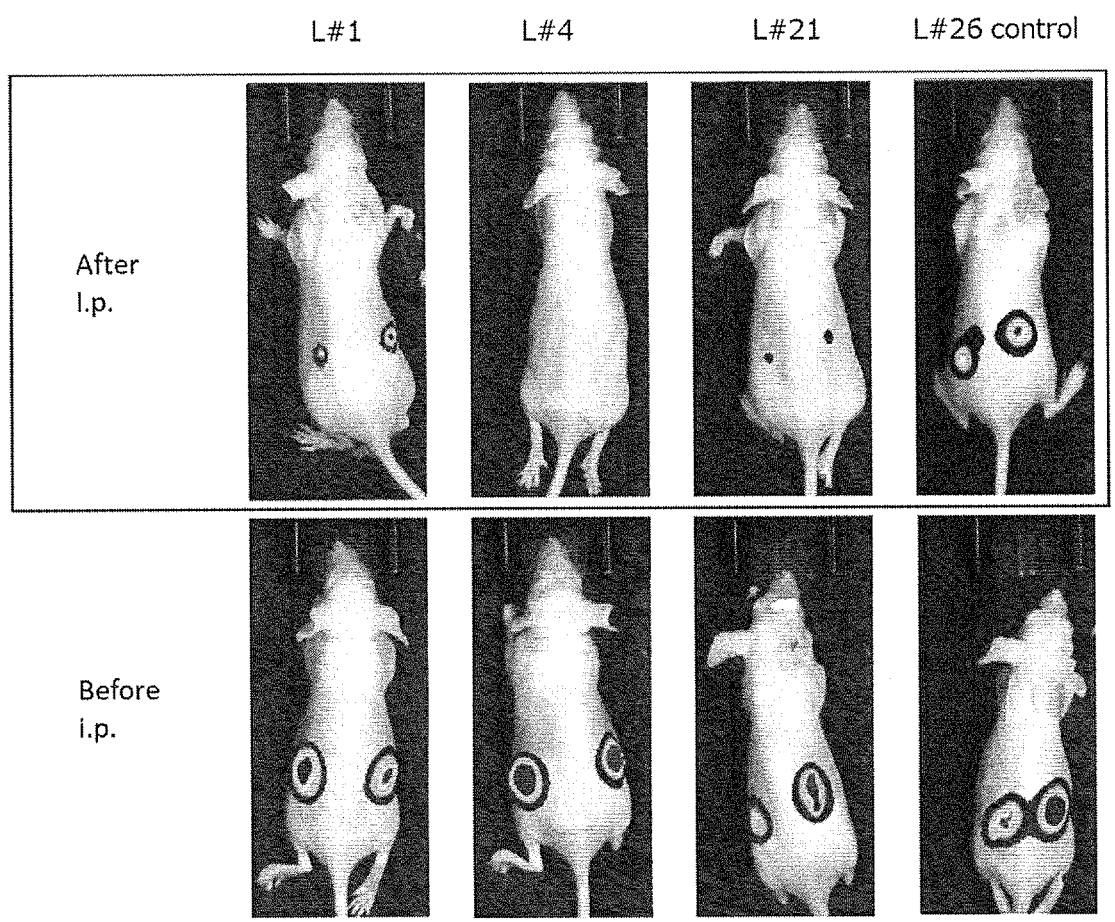
FIG. 13 shows fluorescence images illustrating changes in a tumor state due to intraabdominal administration of hnSR100L #1, hnSR100L #4, and hnSR100L #21 in mice into which hSCLC-LUC cells have been subcutaneously transplanted.

The results of 6-2 above are shown in FIG. 9 (hnSR100-7168-AmNA(17)), FIG. 10 (hnSR100-7172-AmNA(17)), and FIG. 11 (hnSR100-7174-AmNA(15)), the results of 6-3 above are shown in FIG. 12 (hnSR100L #21/hnSR100-7174-LNA(15)), and the results of 6-4 above are shown in FIG. 13 (hnSR100L #1/hnSR100-712-LNA(15), hnSR100L #4/hnSR100-780-LNA(15), and hnSR100L #21/hnSR100-7174-LNA(15)). All the diagrams are photographs indicating the tumor state in the mouse before or after the administration of the antisense oligonucleotide. In all of FIGS. 9 to 13, while the tumor portion shown in the fluorescence image was enlarged in size after the administration of the control oligonucleotide (L26) than before the administration, the tumor portion shown in the fluorescence image was reduced in size after the administration of the antisense oligonucleotide than before the administration. As described above, it was confirmed that the tumor suppressing effect was exhibited in the mouse to which the antisense oligonucleotide had been administered.

Example 7: Design and Synthesis of Antisense Oligonucleotide, and Analysis of Suppression of mRNA Expression In order to obtain more antisense oligonucleotides in addition to those in Example 2, antisense oligonucleotides targeting the mRNA of human nSR100 (hnSR100) (GenBank:NM_194286.3 (SEQ ID No. 1)) were designed. A 2',4'-BNA/LNA ("LNA") represented by Formula (a) above was used as a sugar-modified nucleoside.

Antisense oligonucleotides were designed and synthesized in the same manner as in Examples 1 and 2. All the antisense oligonucleotides were designed as a 3-9-2-1 gapmer in which three bases on the 5' end side (5' wing region) are sugar-modified nucleosides (LNAs), subsequent nine bases (gap region) are native nucleosides (DNAs), two bases close to the center in subsequent three bases on the 3' end side (3' wing region) are sugar-modified nucleosides, and one base at the 3' end is a native nucleoside. All the used oligonucleotides were S-oligonucleotides.

The suppression of the mRNA expression by the antisense oligonucleotide was analyzed using the STC-1 cells as the human SCLC cells in the same manner as in 3-1 above. A case where the oligonucleotides had not been added was taken as a control. For comparison, an N26 oligonucleotide (base sequence: 5'-TGAacaaaataaTAc-3'; a base represented by an uppercase letter is a 2',4'-BNA/LNA, a base represented by a lowercase letter is a DNA, and this oligonucleotide is an S-oligonucleotide; SEQ ID No. 100) was used.

Table 4 shows the antisense oligonucleotides that were prepared and used to examine the suppression of expression. Table 4 below shows the names of the antisense oligonucleotides ("Oligonucleotide Name") together with the 5' ends and the 3' ends of the target regions therefor (indicated as the base positions in SEQ ID No. 1).

TABLE 4

|                       | Target Sequence |        |
|-----------------------|-----------------|--------|
| Oligonucleotide Name  | 5' end          | 3' end |
| hnSR100-647-LNA(15)   | 647             | 661    |
| hnSR100-677-LNA(15)   | 677             | 691    |
| hnSR100-680-LNA(15)   | 680             | 694    |
| hnSR100-711-LNA(15)   | 711             | 725    |
| hnSR100-714-LNA(15)   | 714             | 728    |
| hnSR100-718-LNA(15)   | 718             | 732    |
| hnSR100-755-LNA(15)   | 755             | 769    |
| hnSR100-758-LNA(15)   | 758             | 772    |
| hnSR100-1061-LNA(15)  | 1061            | 1075   |
| hnSR100-1064-LNA(15)  | 1064            | 1078   |
| hnSR100-2380-LNA(15)  | 2380            | 2394   |
| hnSR100-3102-LNA(15)  | 3102            | 3116   |
| hnSR100-3524-LNA(15)  | 3524            | 3538   |
| hnSR100-3584-LNA(15)  | 3584            | 3598   |

TABLE 4-continued

| Oligonucleotide Name | Target Sequence | |
|---|---|---|
| | 5' end | 3' end |
| hnSR100-3587-LNA(15) | 3587 | 3601 |
| hnSR100-3841-LNA(15) | 3841 | 3855 |
| hnSR100-3850-LNA(15) | 3850 | 3864 |
| hnSR100-3854-LNA(15) | 3854 | 3868 |
| hnSR100-3857-LNA(15) | 3857 | 3871 |
| hnSR100-4184-LNA(15) | 4184 | 4198 |
| hnSR100-4187-LNA(15) | 4187 | 4201 |
| hnSR100-4300-LNA(15) | 4300 | 4314 |
| hnSR100-4303-LNA(15) | 4303 | 4317 |
| hnSR100-4306-LNA(15) | 4306 | 4320 |
| hnSR100-4309-LNA(15) | 4309 | 4323 |
| hnSR100-4312-LNA(15) | 4312 | 4326 |
| hnSR100-4317-LNA(15) | 4317 | 4331 |
| hnSR100-7047-LNA(15) | 7047 | 7061 |

The description of hnSR100-p-n(L) in Table 1, which represents an antisense oligonucleotide, also applies to hnSR100-p-n(L) in Table 4. "n" represents an LNA in Table 4. For example, in the case of hnSR100-680-LNA(15), position 680 of the base sequence of SEQ ID No. 1 corresponds to the 5' end of the target region, an LNA is contained, and the length is 15 mer.

Figure 14:
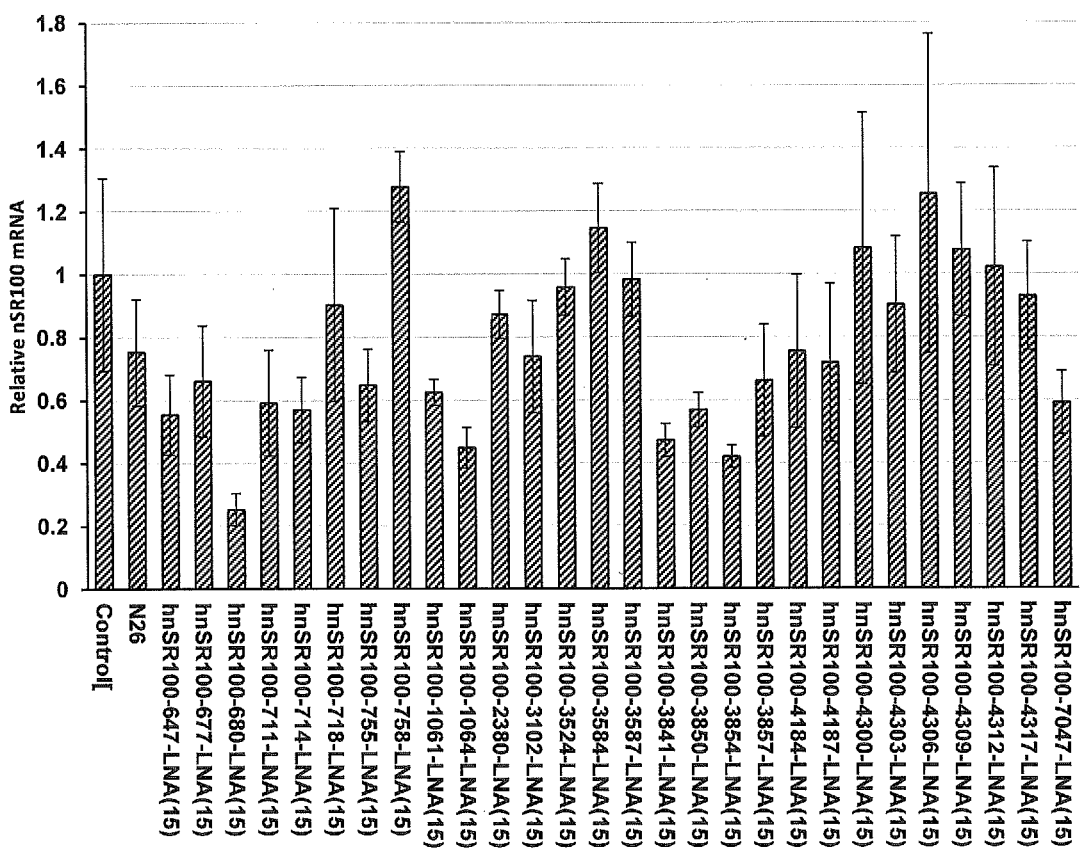
FIG. 14 is a graph illustrating hnSR100 mRNA levels in human SCLC cells (STC-1 cells) to which various antisense oligonucleotides have been added in vitro.
Figure 15:
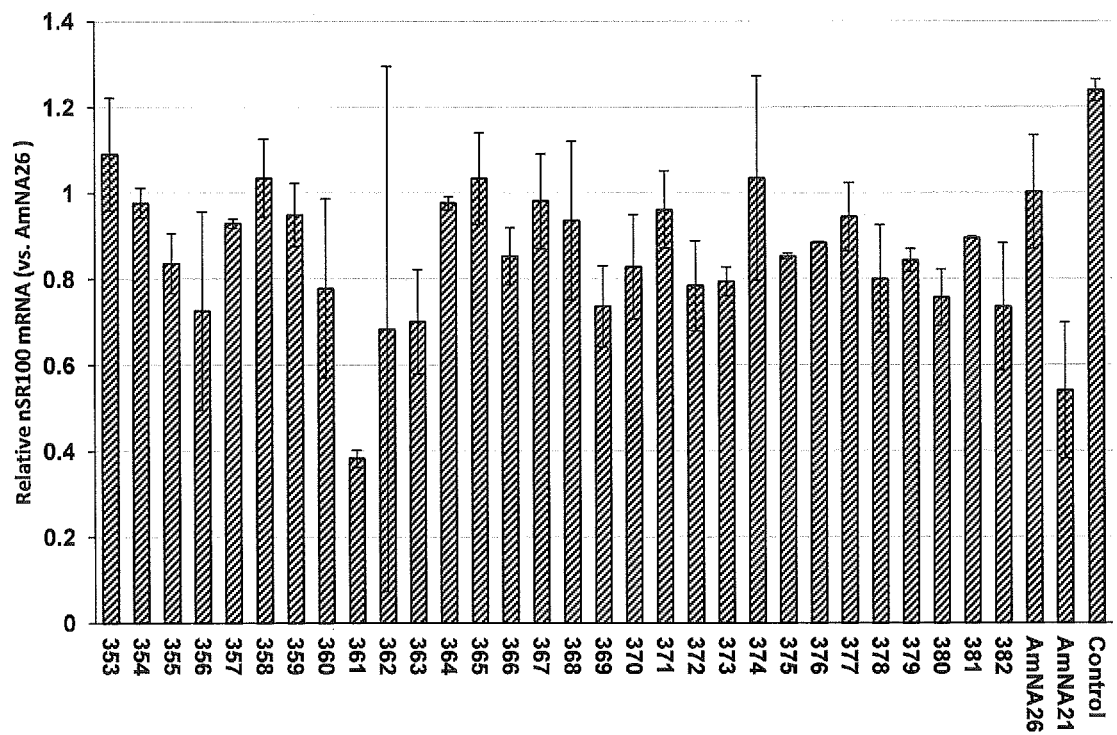
FIG. 15 is a graph illustrating hnSR100 mRNA levels in human SCLC cells (STC-1 cells) to which various antisense oligonucleotides have been added in vitro.
Figure 16:
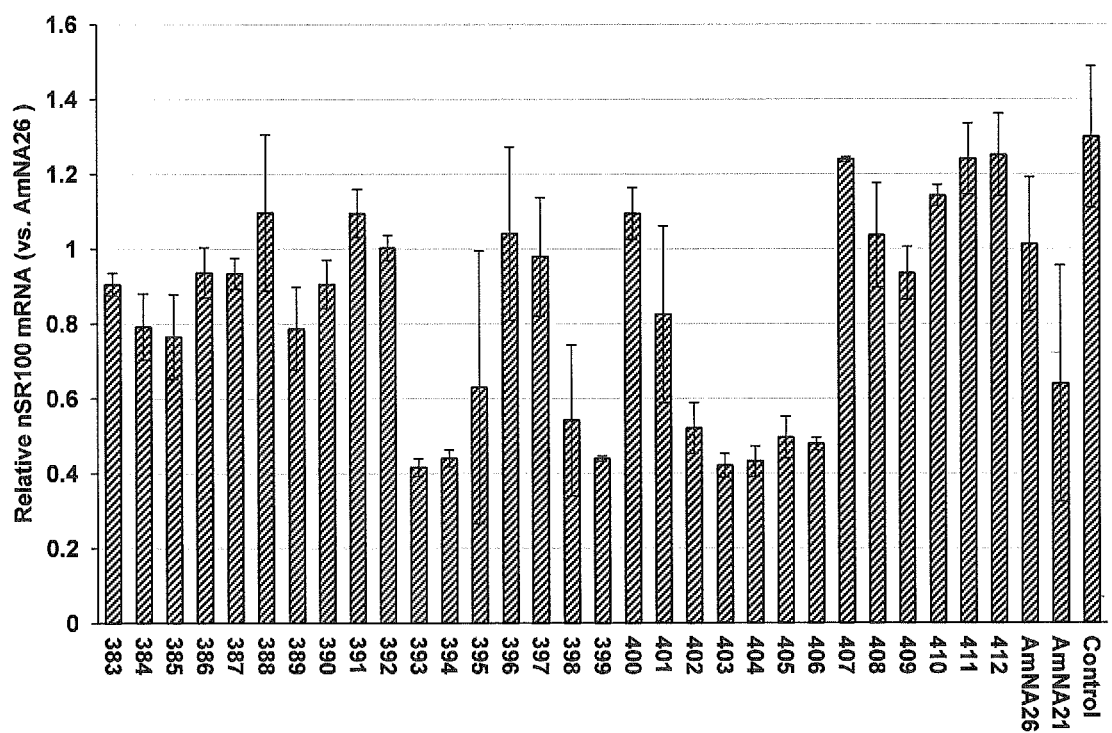
FIG. 16 is a graph illustrating hnSR100 mRNA levels in human SCLC cells (STC-1 cells) to which various antisense oligonucleotides have been added in vitro.
Figure 17:
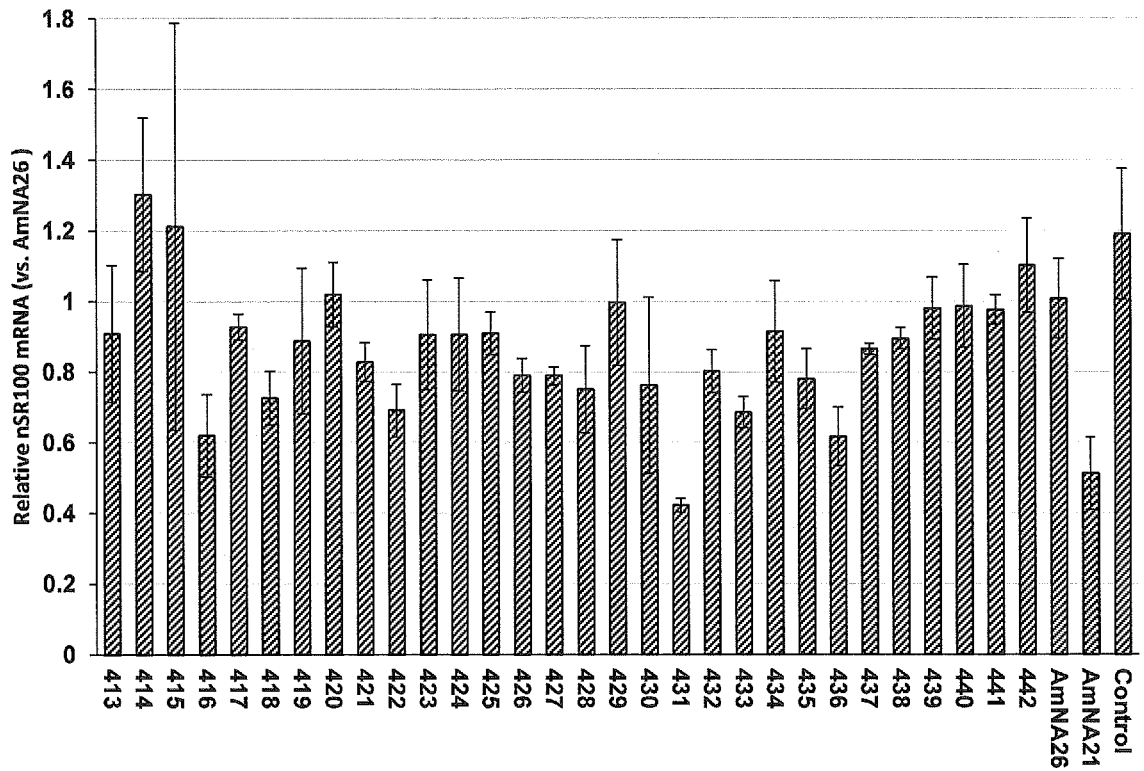
FIG. 17 is a graph illustrating hnSR100 mRNA levels in human SCLC cells (STC-1 cells) to which various antisense oligonucleotides have been added in vitro.
Figure 18:
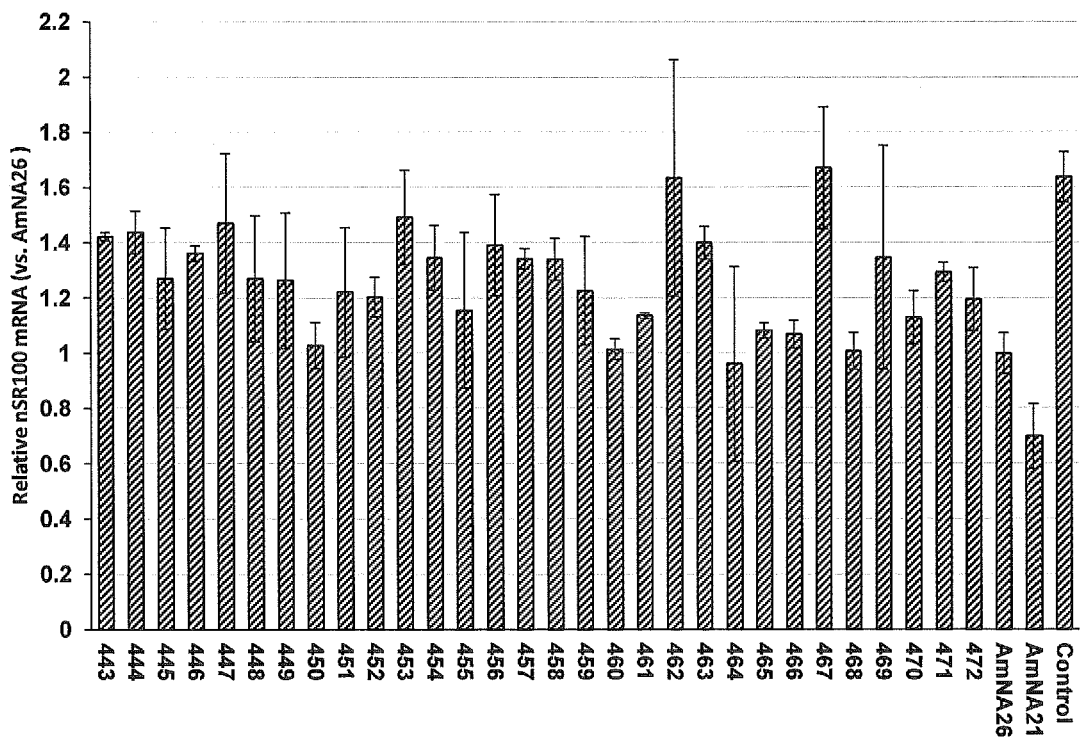
FIG. 18 is a graph illustrating hnSR100 mRNA levels in human SCLC cells (STC-1 cells) to which various antisense oligonucleotides have been added in vitro.
Figure 19:
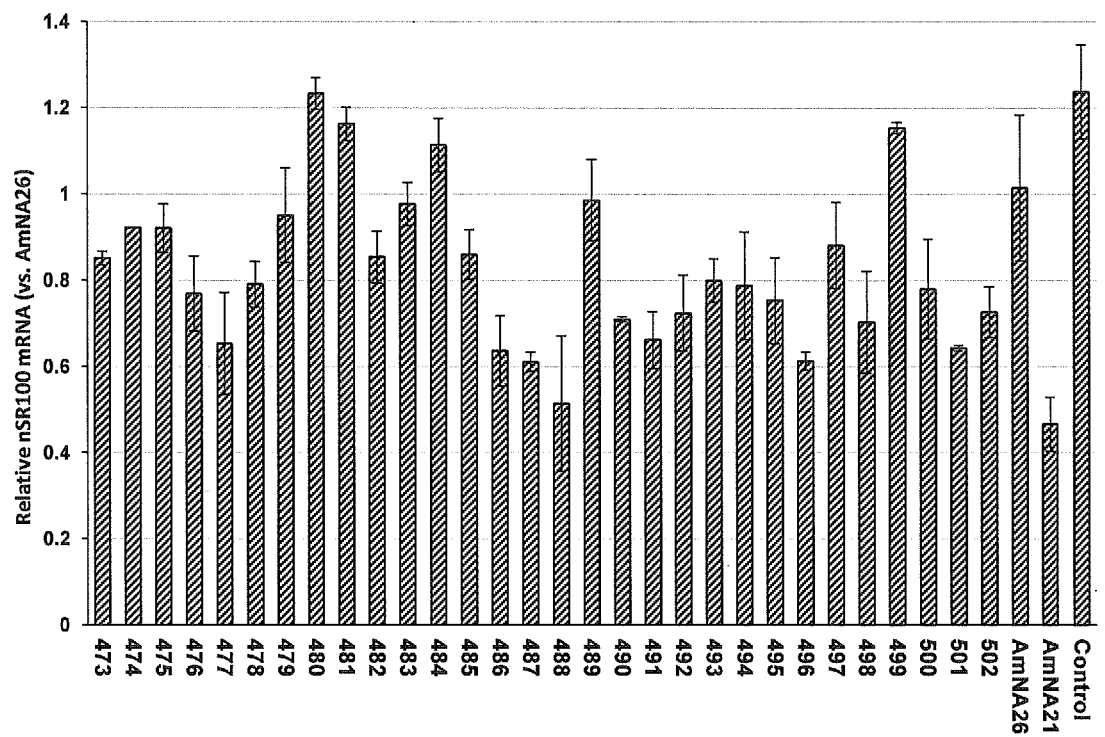
FIG. 19 is a graph illustrating hnSR100 mRNA levels in human SCLC cells (STC-1 cells) to which various antisense oligonucleotides have been added in vitro.
Figure 20:
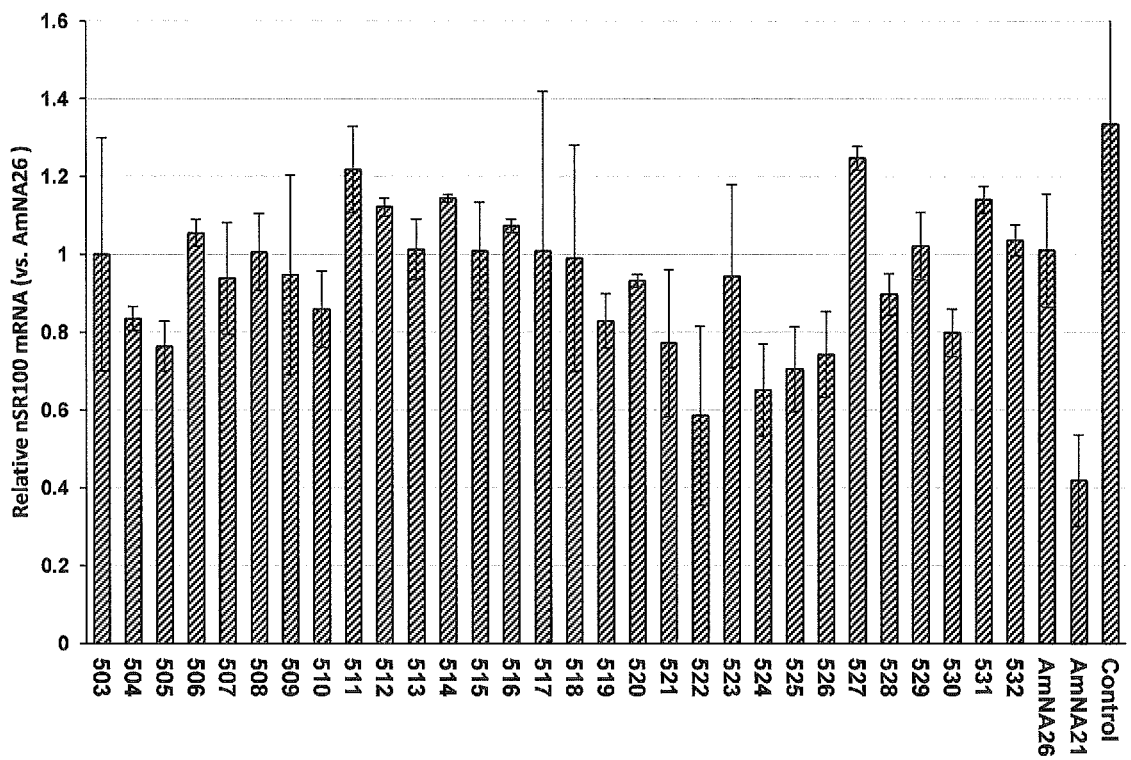
FIG. 20 is a graph illustrating hnSR100 mRNA levels in human SCLC cells (STC-1 cells) to which various antisense oligonucleotides have been added in vitro.
Figure 21:
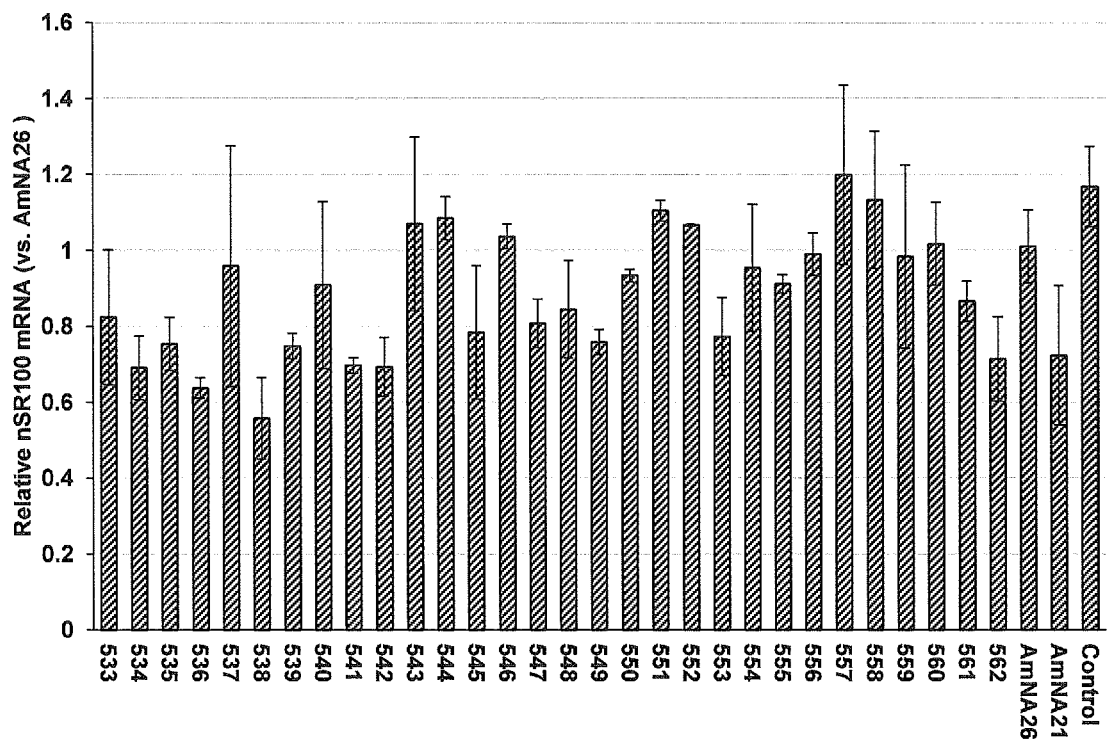
FIG. 21 is a graph illustrating hnSR100 mRNA levels in human SCLC cells (STC-1 cells) to which various antisense oligonucleotides have been added in vitro.
Figure 22:
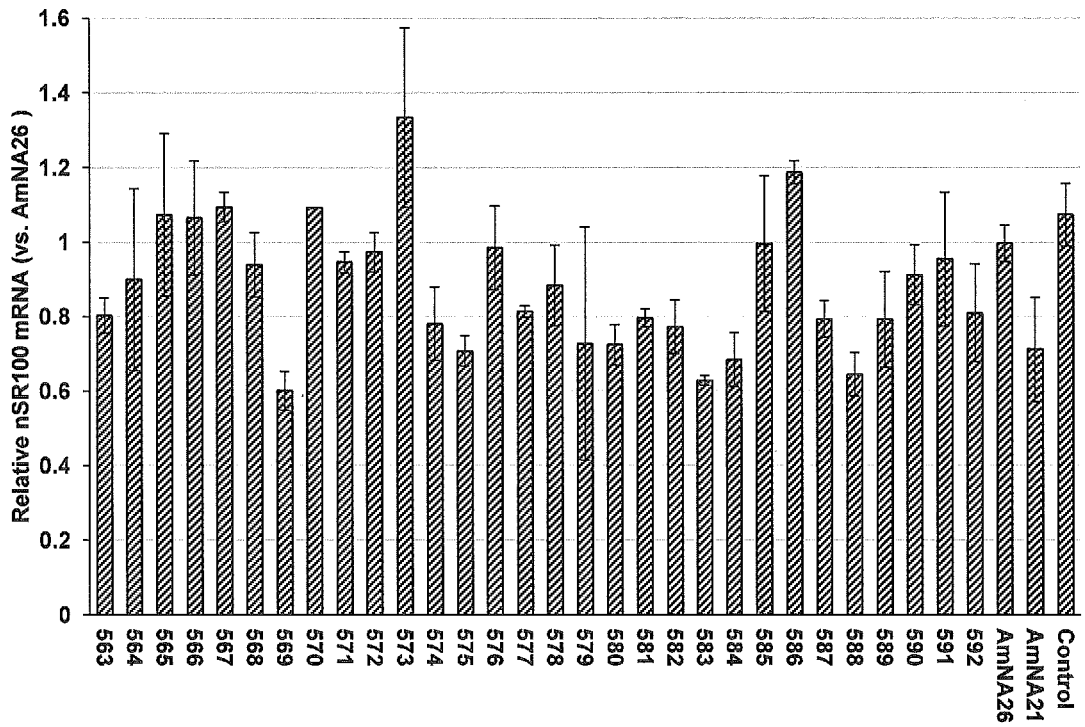
FIG. 22 is a graph illustrating hnSR100 mRNA levels in human SCLC cells (STC-1 cells) to which various antisense oligonucleotides have been added in vitro.
Figure 23:
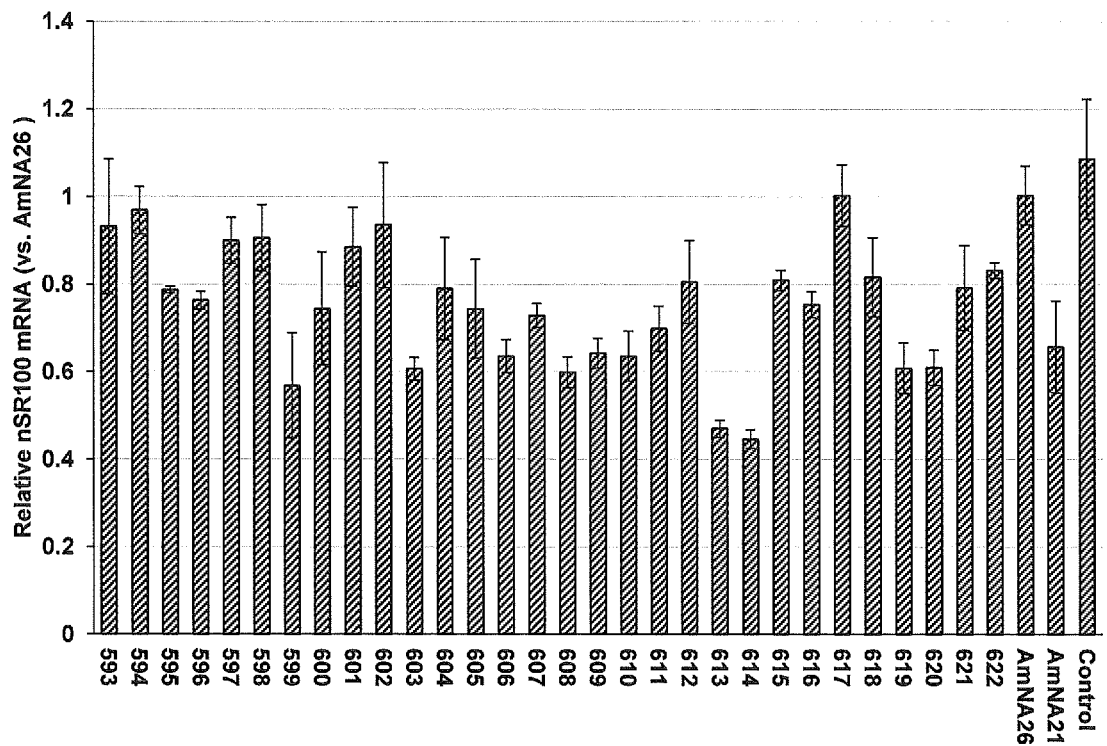
FIG. 23 is a graph illustrating hnSR100 mRNA levels in human SCLC cells (STC-1 cells) to which various antisense oligonucleotides have been added in vitro.
Figure 24:
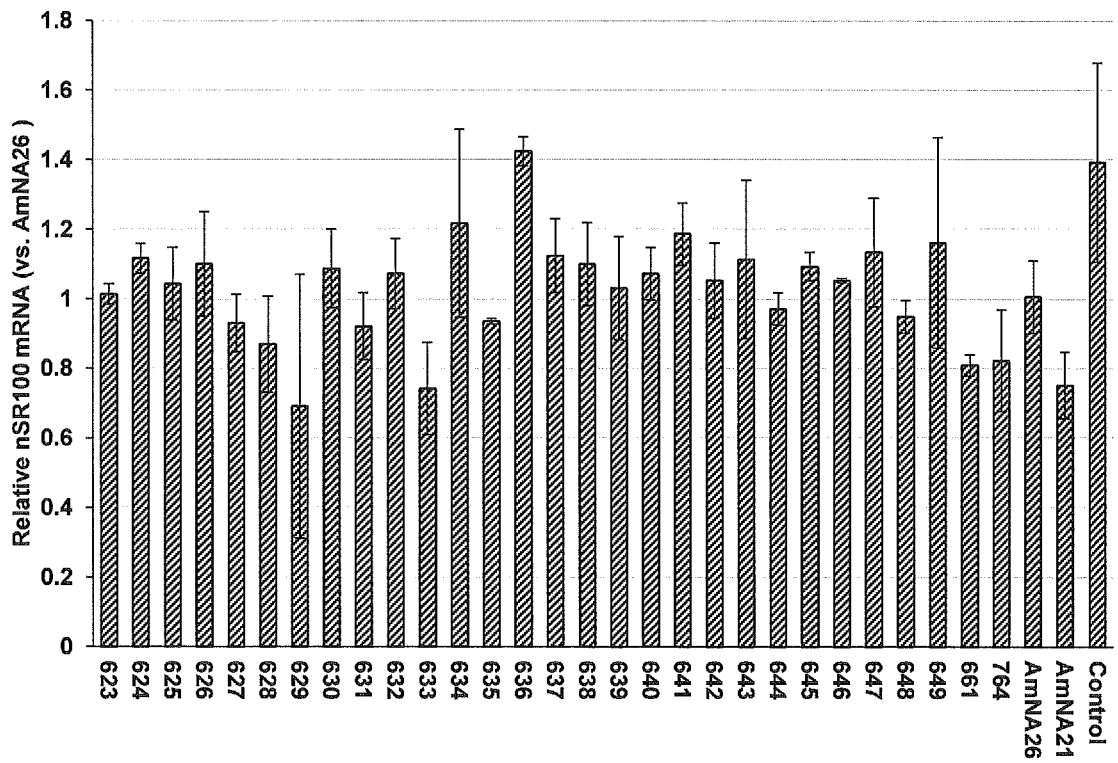
FIG. 24 is a graph illustrating hnSR100 mRNA levels in human SCLC cells (STC-1 cells) to which various antisense oligonucleotides have been added in vitro.

FIG. 14 shows the analysis results of the suppression of the mRNA expression. Table 5 below shows the antisense oligonucleotides that showed a particularly high ratio of suppression of the mRNA expression, together with the sequences (in the direction from 5' toward 3') thereof and the 5' ends and the 3' ends of the target regions thereof (indicated as the base positions in SEQ ID No. 1). The base sequences of the antisense oligonucleotides shown in Table 5 correspond to SEQ ID. Nos. 168 to 171 in the order from top to bottom.

Oligonucleotides having base sequences complementary to the candidate sequences selected as mentioned above were designed as antisense oligonucleotides. Each of the antisense oligonucleotides had a length of 15 mer, and was provided with artificial nucleic acid regions containing sugar-modified nucleosides at the 5' end and the 3' end and a native nucleic acid region containing native nucleosides (DNAs) in the central portion. More specifically, a 3-9-2-1 gapmer was designed in which three bases on the 5' end side (5' wing region) are sugar-modified nucleosides, subsequent nine bases (gap region) are native nucleosides (DNAs), two bases close to the center in subsequent three bases on the 3' end side (3' wing region) are sugar-modified nucleosides, and one base at the 3' end is a native nucleoside, or a 3-9-3 gapmer was designed in which three bases on the 3' end side are all sugar-modified nucleosides.

The following nucleic acids, namely an amide BNA (AmNA) represented by Formula (b), a spirocyclo BNA (scpBNA) represented by Formula (c), and a guanidino BNA (GuNA) represented by Formula (d), were used as sugar-modified nucleosides.

[Chemical Formula 35]

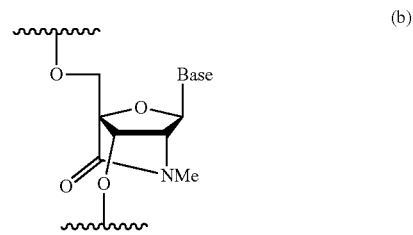

(b)

TABLE 5

| | | Target Seq. | | SEQ.ID. |
|---|---|---|---|---|
| Oligonucleotide Name | Antisense (5'→3') | 5'-end | 3'-end | No. |
| hnSR100-680-LNA(15) | T(L)^G(L)^G(L)^t^g^t^c^a^a^g^t^c^T(L)^T(L)^t | 680 | 694 | 168 |
| hnSR100-1064-LNA(15) | G(L)^5(L)^A(L)^g^a^g^g^g^t^c^t^t^G(L)^G(L)^a | 1064 | 1078 | 169 |
| hnSR100-3841-LNA(15) | G(L)^G(L)^A(L)^a^a^g^a^t^t^g^g^g^T(L)^A(L)^g | 3841 | 3855 | 170 |
| hnSR100-3854-LNA(15) | G(L)^G(L)^T(L)^t^g^a^t^a^g^g^a^t^G(L)^G(L)^g | 3854 | 3868 | 171 |

"5" represents 5-methylcytosine(5mC).
A(L), G(L), 5(L) and T(L) represent 2',4'-BNA/LNA-type bases.
a, g, c and t represent DNA-type bases.
"^" represents a phosphorothioated site.

Example 8: Design and Synthesis of Antisense Oligonucleotide, and Analysis of Suppression of mRNA Expression In order to obtain more antisense oligonucleotides in addition to those in Examples 2 and 7, antisense oligonucleotides targeting the mRNA of human nSR100 (hnSR100) (GenBank: NM_194286.3 (SEQ ID No. 1)) were designed.

In order to select target regions, the reverse sequence (GC) of CG was excluded since CG is toxic in an antisense strand. Next, 299 candidate sequences were selected in the same manner as in Example 2. However, unlike Example 2, the sequence of the mouse mRNA was not taken into consideration when the sequences were selected.

-continued

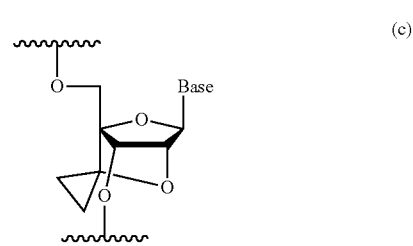

(c)

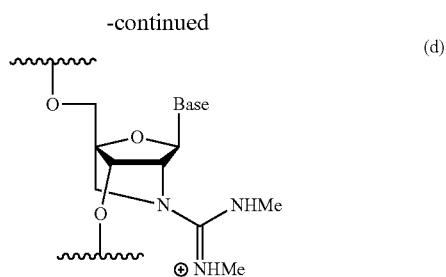

(d)

(where Base is a 5-methylcytosinyl group, thyminyl group, adeninyl group, or guaninyl group, and Me is a methyl.)

The amide BNA (AmNA) was synthesized with reference to the method disclosed in WO 2011/052436. The spirocyclo BNA (scpBNA) was synthesized with reference to the method disclosed in WO 2015/125783. The guanidino BNA (GuNA) was synthesized with reference to the method disclosed in WO 2014/046212.

A 15-mer oligonucleotide containing an amide BNA (AmNA), spirocyclo BNA (scpBNA), or guanidino BNA (GuNA) was synthesized using the same method as that in Example 1. An oligonucleotide containing an amide BNA (AmNA) was obtained in a state in which a hydroxy group at the 5' end was protected by a DMTr (dimethoxytrityl) group and the 3' end was held in a solid phase. Subsequently, a target product was removed from the solid phase support through base treatment, and then the solvent was distilled off. Cartridge purification was performed on the resultant crude product, and thus the target product was obtained. On the other hand, an oligonucleotide containing an amide BNA (AmNA) and one of a spirocyclo BNA (scpBNA) or a guanidino BNA (GuNA) was obtained in a state in which a hydroxy group at the 5' end was not protected by a DMTr (dimethoxytrityl) group and the 3' end was held in a solid phase. Subsequently, a target product was removed from the solid phase support through base treatment, and then the solvent was distilled off. The resultant crude product was purified using reversed phase HPLC, and thus the target product was obtained.

The purities and structures of the obtained oligonucleotides were confirmed using an LC-MS (manufactured by Waters).

Suppression of nSR100 mRNA expression by the antisense oligonucleotides prepared as described above in human SCLC cells in vitro was examined. The antisense oligonucleotides that were prepared and used to examine the suppression of expression were denoted by reference numerals as appropriate (the oligonucleotides containing an AmNA were denoted by reference numerals 353 to 649; the oligonucleotide containing an AmNA and a scpBNA was denoted by reference numeral 661, and the oligonucleotide containing an AmNA and a GuNA was denoted by reference numeral 764). A case where the oligonucleotides had not been added were used as a control. For comparison, an N26 oligonucleotide containing an AmNA (SEQ ID No. 167) (also referred to as an "AmNA26 oligonucleotide") was used. In addition, for comparison, hnSR100-7174-AmNA (15) (SEQ ID No. 152) (shown in Table 3; this oligonucleotide also contains an AmNA in the base sequence based on hnSR100L #21 and thus was also referred to as an "AmNA21 oligonucleotide") was also used.

The STC-1 cells (JCRB Cell Bank) were used as the human SCLC cells. A commercially available transfection reagent (Lipofectamine 3000: available from Thermo Fisher Scientific) was used to introduce each of the antisense oligonucleotides into the STC-1 cells, the qRT-PCR method was used to measure the mRNA expression level, and thus knockdown activity (suppression of mRNA expression) was examined. The following describes the procedure.

The STC-1 cells in a logarithmic growth phase were seeded in the wells (containing a Roswell Park Memorial Institute (RPMI)-1640 medium (high glucose) with 10% fetal bovine serum (FBS)) of a 24-well plate such that the number of cells was $1.0 \times 10^5$ cells per well. After 24 hours, each of the antisense oligonucleotides was added to the well to give a final concentration of 200 nM, and the resultant mixture was incubated for 24 hours.

After the incubation, the cells were collected, and a total RNA was extracted using an RNA extraction kit (Nucleo ZOL manufactured by MACHEREY-NAGEL). A reverse transcription reaction and a PCR amplification reaction using the total RNA as a template were performed using a nucleic acid amplification reaction reagent (QuantiFast Probe RT-PCR kit manufactured by Qiagen). The nucleic acid amplification reaction was performed using the following temperature cycles: 50° C. for 10 minutes→95° C. for 5 minutes→[(95° C. for 10 seconds→60° C. for 30 seconds)× 40 cycles]. In the real-time PCR, the mRNA level of the housekeeping gene human actin was simultaneously quantified, and the hnSR100 mRNA level relative to the actin mRNA level was evaluated. The mRNA level when each of the antisense oligonucleotides or the oligonucleotide was added is indicated as a relative value with respect to the mRNA level, which is taken as 1, in the cells to which the AmNA26 oligonucleotide was added.

The following shows the used primer sets.
Primer set for detecting hnSR100
 Set1-Fw: tgacaaagacttgacaccacc (SEQ ID No. 101)
 Set1-Rv: acctgcgtcgcttgtgttt (SEQ ID No. 102)
Primer set for detecting human actin
 TaqMan Gene Expression Assay
  Hs99999903_m1_4331182 (Thermo Fisher Scientific)

FIGS. 15 to 24 show the results. The antisense oligonucleotides that showed a particularly high ratio of suppression of the mRNA expression were listed in Tables 6 and 7 below and shown together with the sequences (in the direction from 5' toward 3') thereof, the 5' ends and the 3' ends of the target regions therefor (indicated as the base positions in SEQ ID No. 1), and the reference numbers thereof. The description of hnSR100-p-n(L) in Tables 1 to 3, which represents an antisense oligonucleotide, also applies to hnSR100-p-n(L) in Tables 6 and 7. When "n" is "AmNA", the sugar-modified nucleoside (artificial nucleic acid) in the oligonucleotide is an AmNA, when "n" is "AmNA, scpBNA", an AmNA and an scpBNA are used as the sugar-modified nucleosides (artificial nucleic acids) in the oligonucleotide, and when "n" is "AmNA, GuNA", an AmNA and a GuNA are used as the sugar-modified nucleosides (artificial nucleic acids) in the oligonucleotide. The 3' end of the oligonucleotide is a DNA when "n" is "AmNA" or "AmNA, GuNA", whereas the 3' end of the oligonucleotide is also a sugar-modified nucleoside (artificial nucleic acid) when "n" is "AmNA, scpBNA" The oligonucleotides in which "n" is "AmNA" listed in Tables 6 and 7 are top 46 antisense oligonucleotides in the 297 sequences tested in this example. The base sequences of the antisense oligonucleotides shown in Tables 6 and 7 correspond to SEQ ID. Nos. 172 to 219 in the order from top to bottom.

TABLE 6

| Oligonucleotide Name | Antisense (5'→3') | Target Seq. 5'-end | Target Seq. 3'-end | SEQ. ID. No. | Ref. No. |
|---|---|---|---|---|---|
| hnSR100-604-AmNA(15) | 5(Y)^A(Y)^A(Y)^ctgttggtg5(Y)^5(Y)^c | 604 | 618 | 172 | 361 |
| hnSR100-1566-AmNA(15) | T(Y)^G(Y)^5(Y)^tggcataggA(Y)^G(Y)^g | 1566 | 1580 | 173 | 393 |
| hnSR100-1582-AmNA(15) | T(Y)^G(Y)^A(Y)^ctggaggat5(Y)^G(Y)^g | 1582 | 1596 | 174 | 394 |
| hnSR100-1584-AmNA(15) | A(Y)^G(Y)^T(Y)^gactggaggA(Y)^T(Y)^c | 1584 | 1598 | 175 | 395 |
| hnSR100-1633-AmNA(15) | 5(Y)^G(Y)^G(Y)^ctttgggtgT(Y)^A(Y)^c | 1633 | 1647 | 176 | 398 |
| hnSR100-1645-AmNA(15) | G(Y)^A(Y)^A(Y)^gaggtggat5(Y)^G(Y)^g | 1645 | 1659 | 177 | 399 |
| hnSR100-1689-AmNA(15) | A(Y)^5(Y)^T(Y)^tggaggaatA(Y)^G(Y)^c | 1689 | 1703 | 178 | 402 |
| hnSR100-1690-AmNA(15) | G(Y)^A(Y)^5(Y)^ttggaggaaT(Y)^A(Y)^g | 1690 | 1704 | 179 | 403 |
| hnSR100-1697-AmNA(15) | 5(Y)^T(Y)^T(Y)^gccagacttG(Y)^G(Y)^a | 1697 | 1711 | 180 | 404 |
| hnSR100-1858-AmNA(15) | T(Y)^T(Y)^T(Y)^ctcataggcG(Y)^A(Y)^g | 1858 | 1872 | 181 | 405 |
| hnSR100-1863-AmNA(15) | G(Y)^G(Y)^5(Y)^gctttctcaT(Y)^A(Y)^g | 1863 | 1877 | 182 | 406 |
| hnSR100-2906-AmNA(15) | 5(Y)^A(Y)^T(Y)^gctgaggtaT(Y)^T(Y)^g | 2906 | 2920 | 183 | 431 |
| hnSR100-4810-AmNA(15) | A(Y)^5(Y)^A(Y)^agggatttcG(Y)^A(Y)^c | 4810 | 4824 | 184 | 488 |
| hnSR100-5907-AmNA(15) | T(Y)^G(Y)^G(Y)^tgatctgtcA(Y)^T(Y)^a | 5907 | 5921 | 185 | 534 |
| hnSR100-5908-AmNA(15) | 5(Y)^T(Y)^G(Y)^gtgatctgt5(Y)^A(Y)^t | 5908 | 5922 | 186 | 535 |
| hnSR100-5950-AmNA(15) | G(Y)^G(Y)^A(Y)^tgttggtttT(Y)^T(Y)^g | 5950 | 5964 | 187 | 536 |
| hnSR100-6015-AmNA(15) | A(Y)^G(Y)^5(Y)^gggaaggtcA(Y)^A(Y)^a | 6015 | 6029 | 188 | 538 |
| hnSR100-6239-AmNA(15) | T(Y)^5(Y)^G(Y)^tttttacttT(Y)^5(Y)^a | 6239 | 6253 | 189 | 541 |
| hnSR100-6240-AmNA(15) | T(Y)^T(Y)^5(Y)^gtttttactT(Y)^T(Y)^c | 6240 | 6254 | 190 | 542 |
| hnSR100-6302-AmNA(15) | A(Y)^A(Y)^T(Y)^aggggcttT(Y)^T(Y)^a | 6302 | 6316 | 191 | 549 |
| hnSR100-6448-AmNA(15) | A(Y)^A(Y)^A(Y)^tgaagtgatG(Y)^5(Y)^g | 6448 | 6462 | 192 | 553 |
| hnSR100-6755-AmNA(15) | 5(Y)^A(Y)^T(Y)^aagtttctcA(Y)^G(Y)^c | 6755 | 6769 | 193 | 562 |
| hnSR100-6870-AmNA(15) | A(Y)^5(Y)^A(Y)^gcaaccacaG(Y)^A(Y)^t | 6870 | 6884 | 194 | 569 |

TABLE 7

| Oligonucleotide Name | Antisense(5'→3') | Target Seq. 5'-ter. | Target Seq. 3'-ter. | SEQ. ID. No. | Ref. No. |
|---|---|---|---|---|---|
| hnSR100-7057-AmNA(15) | 5(Y)^5(Y)^A(Y)^attctcaatA(Y)^G(Y)^c | 7057 | 7071 | 195 | 574 |
| hnSR100-7060-AmNA(15) | G(Y)^G(Y)^A(Y)^ccaattctcA(Y)^A(Y)^t | 7060 | 7074 | 196 | 575 |
| hnSR100-7130-AmNA(15) | G(Y)^T(Y)^G(Y)^attctagca5(Y)^T(Y)^c | 7130 | 7144 | 197 | 579 |
| hnSR100-7131-AmNA(15) | G(Y)^G(Y)^T(Y)^gattctagcA(Y)^5(Y)^t | 7131 | 7145 | 198 | 580 |
| hnSR100-7133-AmNA(15) | T(Y)^T(Y)^G(Y)^gtgattctaG(Y)^5(Y)^a | 7133 | 7147 | 199 | 581 |
| hnSR100-7134-AmNA(15) | 5(Y)^T(Y)^T(Y)^ggtgattctA(Y)^G(Y)^c | 7134 | 7148 | 200 | 582 |
| hnSR100-7135-AmNA(15) | G(Y)^5(Y)^T(Y)^tggtgattcT(Y)^A(Y)^g | 7135 | 7149 | 201 | 583 |
| hnSR100-7136-AmNA(15) | T(Y)^G(Y)^5(Y)^ttggtgatt5(Y)^T(Y)^a | 7136 | 7150 | 202 | 584 |

TABLE 7-continued

| Oligonucleotide Name | Antisense(5'→3') | Target Seq. 5'-ter. | Target Seq. 3'-ter. | SEQ. ID. No. | Ref. No. |
|---|---|---|---|---|---|
| hnSR100-7203-AmNA(15) | 5(Y)^5(Y)^A(Y)^gtgttttagT(Y)^T(Y)^c | 7203 | 7217 | 203 | 588 |
| hnSR100-7365-AmNA(15) | A(Y)^A(Y)^G(Y)^atgaggcatA(Y)^G(Y)^c | 7365 | 7379 | 204 | 599 |
| hnSR100-7373-AmNA(15) | 5(Y)^T(Y)^5(Y)^gttagaagaT(Y)^G(Y)^a | 7373 | 7387 | 205 | 603 |
| hnSR100-7688-AmNA(15) | T(Y)^A(Y)^T(Y)^atgactgtgG(Y)^G(Y)^a | 7688 | 7702 | 206 | 606 |
| hnSR100-7733-AmNA(15) | 5(Y)^A(Y)^G(Y)^gatacaagaG(Y)^T(Y)^t | 7733 | 7747 | 207 | 607 |
| hnSR100-7734-AmNA(15) | 5(Y)^5(Y)^A(Y)^ggatacaagA(Y)^G(Y)^t | 7734 | 7748 | 208 | 608 |
| hnSR100-7769-AmNA(15) | G(Y)^A(Y)^G(Y)^agaagttcaA(Y)^A(Y)^c | 7769 | 7783 | 209 | 609 |
| hnSR100-7792-AmNA(15) | A(Y)^T(Y)^G(Y)^actttggac5(Y)^A(Y)^c | 7792 | 7806 | 210 | 610 |
| hnSR100-7794-AmNA(15) | T(Y)^G(Y)^A(Y)^tgactttggA(Y)^5(Y)^c | 7794 | 7808 | 211 | 611 |
| hnSR100-7827-AmNA(15) | 5(Y)^A(Y)^G(Y)^ggcaaggtaA(Y)^G(Y)^c | 7827 | 7841 | 212 | 613 |
| hnSR100-7829-AmNA(15) | A(Y)^G(Y)^5(Y)^agggcaaggT(Y)^A(Y)^a | 7829 | 7843 | 213 | 614 |
| hnSR100-7859-AmNA(15) | T(Y)^G(Y)^G(Y)^gcatgtcaa5(Y)^T(Y)^c | 7959 | 7973 | 214 | 619 |
| hnSR100-7860-AmNA(15) | T(Y)^T(Y)^G(Y)^ggcatgtcaA(Y)^5(Y)^t | 7960 | 7974 | 215 | 620 |
| hnSR100-8001-AmNA(15) | A(Y)^T(Y)^G(Y)^ttggacattG(Y)^A(Y)^g | 8001 | 8015 | 216 | 629 |
| hnSR100-8165-AmNA(15) | A(Y)^T(Y)^G(Y)^gccttggggT(Y)^G(Y)^c | 8165 | 8179 | 217 | 633 |
| hnSR100-7174-AmNA, scpBNA(15) | T(S)^T(S)^G(Y)^tgtgactgaA(Y)^G(Y)^5(S) | 7174 | 7188 | 218 | 661 |
| hnSR100-7174-AmNA, GuNA(15) | T(D)^T(D)^G(Y)^tgtgactgaA(Y)^G(Y)^c | 7174 | 7188 | 219 | 764 |

"5" represents a 5-methylcytosine (5 mC).
A(Y), G(Y), 5(Y), and T(Y) represent AmNA-type bases.
A(D), G(D), 5(D), and T(D) represent GuNA-type bases.
A(S), G(S), 5(S), and T(S) represent scpBNA-type bases.
a, g, c, and t represent DNA-type bases.
"^" represents a phosphorothioated site.

It was found from the results of the preceding examples and the results of this example that, in all of the case where an AmNA was contained, the case where a GuNA was contained, and the case where a scpBNA was contained, some antisense oligonucleotides reduced the mRNA level, that is, suppressed the mRNA expression, compared with the cases where the oligonucleotides had not been added to the cells ("control") and AmNA26 had been added to the cells.

INDUSTRIAL APPLICABILITY

The present invention is useful for manufacturing medicines for treatment of cancer.

The invention claimed is:

1. An oligonucleotide or a pharmacologically acceptable salt thereof, wherein the oligonucleotide is:
   hnSR100-7174-AmNA(15) (SEQ ID No. 152),
   hnSR100-7172-AmNA(17) (SEQ ID No. 153),
   hnSR100-7170-AmNA(19) (SEQ ID No. 154),
   hnSR100-7172-AmNA(15) (SEQ ID No. 155),
   hnSR100-7170-AmNA(17) (SEQ ID No. 156),
   hnSR100-7168-AmNA(19) (SEQ ID No. 157),
   hnSR100-7170-AmNA(15) (SEQ ID No. 158),
   hnSR100-7174-AmNA(17) (SEQ ID No. 162),
   hnSR100-7172-AmNA(19) (SEQ ID No. 163),
   hnSR100-7203-AmNA(15) (SEQ ID No. 203),
   hnSR100-7174-AmNA, scpBNA(15) (SEQ ID No. 218), or
   hnSR100-7174-AmNA, GuNA(15) (SEQ ID No. 219).

2. The oligonucleotide or the pharmacologically acceptable salt thereof according to claim 1, wherein the oligonucleotide is:
   hnSR100-7172-AmNA(17) (SEQ ID No. 153),
   hnSR100-7170-AmNA(17) (SEQ ID No. 156), or
   hnSR100-7174-AmNA(17) (SEQ ID No. 162).

3. An oligonucleotide or a pharmacologically acceptable salt thereof, wherein the oligonucleotide is:
   hnSR100L #21/hnSR100-7174-LNA(15) (SEQ ID No. 96),
   hnSR100L #22/hnSR100-7177-LNA(15) (SEQ ID No. 97),
   hnSR100-7172-LNA(15) (SEQ ID No. 125),
   hnSR100-7170-LNA(15) (SEQ ID No. 128),
   hnSR100-7176-LNA(15) (SEQ ID No. 131),
   hnSR100-7178-LNA(15) (SEQ ID No. 134),
   hnSR100-7174-AmNA(15) (SEQ ID No. 152),
   hnSR100-7172-AmNA(15) (SEQ ID No. 155),
   hnSR100-7170-AmNA(15) (SEQ ID No. 158),
   hnSR100-7203-AmNA(15) (SEQ ID No. 203),
   hnSR100-7174-AmNA, scpBNA(15) (SEQ ID No. 218), or
   hnSR100-7174-AmNA, GuNA(15) (SEQ ID No. 219).

4. An oligonucleotide or a pharmacologically acceptable salt thereof, wherein the oligonucleotide is:
   hnSR100-7170-LNA(19) (SEQ ID No. 124),
   hnSR100-7168-LNA(19) (SEQ ID No. 127),
   hnSR100-7166-LNA(19) (SEQ ID No. 130),
   hnSR100-7172-LNA(19) (SEQ ID No. 133),
   hnSR100-7170-AmNA(19) (SEQ ID No. 154),
   hnSR100-7168-AmNA(19) (SEQ ID No. 157), or
   hnSR100-7172-AmNA(19) (SEQ ID No. 163).

* * * * *